(12) United States Patent
Morrison et al.

(10) Patent No.: US 11,622,974 B2
(45) Date of Patent: Apr. 11, 2023

(54) PREBIOTIC COMPOSITION AND ITS USE

(71) Applicant: CP KELCO U.S., INC., Atlanta, GA (US)

(72) Inventors: Neil A. Morrison, San Diego, CA (US); Hailong Yu, San Diego, CA (US); John P. Abdou, San Diego, CA (US); Narayana Murthy Manjunatha, San Diego, CA (US); Todd A. Talashek, San Diego, CA (US)

(73) Assignee: C.P. Kelco U.S., Inc., Atlanta, GA (US)

( * ) Notice: Subject to any disclaimer, the term of this patent is extended or adjusted under 35 U.S.C. 154(b) by 92 days.

(21) Appl. No.: 16/743,806

(22) Filed: Jan. 15, 2020

(65) Prior Publication Data

US 2020/0230167 A1 Jul. 23, 2020

Related U.S. Application Data

(60) Provisional application No. 62/794,452, filed on Jan. 18, 2019, provisional application No. 62/869,248, filed on Jul. 1, 2019.

(51) Int. Cl.
*A61K 31/715* (2006.01)
*A61P 1/14* (2006.01)
*A61K 9/00* (2006.01)
*C08B 37/00* (2006.01)

(52) U.S. Cl.
CPC .......... *A61K 31/715* (2013.01); *A61K 9/0053* (2013.01); *A61P 1/14* (2018.01); *C08B 37/006* (2013.01)

(58) Field of Classification Search
CPC ....... A61K 31/715; A61K 9/0053; A61P 1/14; C08B 37/006
USPC .......................................................... 514/54
See application file for complete search history.

(56) References Cited

U.S. PATENT DOCUMENTS

| 4,326,053 | A | 4/1982 | Kang et al. |
| 4,342,866 | A | 8/1982 | Kang et al. |
| 4,401,760 | A | 8/1983 | Peik et al. |
| 5,175,277 | A | 12/1992 | Rakitsky et al. |
| 5,175,278 | A | 12/1992 | Peik et al. |
| 5,342,626 | A | 8/1994 | Winston, Jr. et al. |
| 6,242,035 | B1 | 6/2001 | Clark et al. |
| 6,602,996 | B1 | 8/2003 | Sworn et al. |
| 6,663,911 | B2 | 12/2003 | Valli et al. |
| 8,313,789 | B2 | 11/2012 | Hotchkiss et al. |
| 8,513,408 | B2 | 8/2013 | Yuan et al. |
| 9,028,861 | B2 | 5/2015 | Cheuk et al. |
| 2005/0118326 | A1* | 6/2005 | Anfinsen ............... A23L 7/135 426/658 |
| 2008/0008814 | A1 | 1/2008 | Jackson et al. |
| 2010/0092440 | A1 | 4/2010 | Strozzi et al. |
| 2013/0189748 | A1 | 7/2013 | Harding et al. |
| 2016/0263170 | A1 | 9/2016 | Turner |
| 2016/0295887 | A1 | 10/2016 | Morrison et al. |

FOREIGN PATENT DOCUMENTS

| CN | 109294950 A | 2/2019 |
| EP | 2589302 A1 | 5/2013 |
| MD | 992 Y | 1/2016 |
| WO | 2004/002240 A2 | 1/2004 |
| WO | 2004002240 A2 | 1/2004 |
| WO | 2006/032005 A2 | 3/2006 |
| WO | 2007/050656 A2 | 5/2007 |
| WO | 2007/095425 A1 | 8/2007 |
| WO | 2008/065492 A2 | 6/2009 |
| WO | 2011/060123 A1 | 5/2011 |
| WO | 2019/090181 A1 | 5/2019 |

OTHER PUBLICATIONS

Tetsuguchi et al. (J Nutr Sci Vitaminol, 1997, 43, 515-527).*
Munukka et al. (The ISME Journal (2017) 11, 1667-1679).*
Koga et al. (Pediatric Research, vol. 80 | No. 6 | Dec. 2016, 844-852).*
Kennedy et al. (Microbiobgy (1 994), 140,3007-301 3).*
Partial International Search Report & Written Opinion Issued in PCT Patent Application No. PCT/US2020/013742, dated Jun. 4, 2020; 21 Pages.
Ming-Ju Chen, et al' Optimal thermotolerance of Bifidobacterium bifidum in gellan-alginate microparticles:, Biotechnology and Bioengineering, vol. 98, No. 2, Jan. 1, 2007, pp. 411-419.
KELCOGEL® gellan gum, 5th Ed. (2008).
KELTROL® / KELZAN® xanthan gum, 8th Ed. (2008).
Anderson et al., The dietary effects of gellan gum in humans, Food Addit. Contam. (1988) 5(3): 237-249 ("Anderson (1988)").
Diltz et al., Location of O-acetyl groups in S-657 using the reductive cleavage method, Carbohydr. Res. (2001) 331(3): 265-270 ("Diltz (2001)").
Edwards et al., Caecal and faecal shortchain fatty acids and stool output in rats fed on diets containing nonstarch polysaccharides, Brit. J. Nutr. (1995) 73: 773-781 ("Edwards (1995)").
Fallourd et al., Ingredient Selection for Stabilisation and Texture Optimisation of Functional Beverages and the Inclusion of Dietary Fibre, Functional and Specialty Beverage Technology (2009) Pt. 1, Sect. 1, 3-38, at 20 ("Fallourd (2009)").
Guimaraes et al., Manufacturing a prebiotic whey beverage exploring the influence of degree of inulin polymerization, Food Hydrocolloids (2018) 77: 787-795 ("Guimaraes (2018)").
Jansson, et al., Structural Studies of a Polysaccharide (S-194) Elaborated by Alcaligenes ATCC 31961, Carbohydr. Res. (1986) 156: 157-163 ("Jansson (1986)").
Karlton-Senaye et al., Impact of gums on the growth of probiotics, Agro Food Ind. Hi Tech. (2013) 24(4): 10-14 ("Karlton-Senaye (2013)").
Li et al, Screening and enzymatic activity of high-efficiency gellan lyase producing bacteria Pseudoalteromonas nodoensis PE1, Bioengineered (2019) 10(1): 240-249 ("Li (2019)").
Martinez et al., Resistant Starches Types 2 and 4 Have Differential Effects on the Composition of the Fecal Microbiota in Human Subjects, PLOS One (2010) 5(11): e15-46, ("Martinez (2010)").

(Continued)

*Primary Examiner* — Shaojia A Jiang
*Assistant Examiner* — Michael C Henry
(74) *Attorney, Agent, or Firm* — Merchant & Gould P.C.; Daniel R. Evans

(57) ABSTRACT

Disclosed herein is an ingestible composition comprising a sphingan and its use as a prebiotic.

20 Claims, 32 Drawing Sheets

(56) References Cited

OTHER PUBLICATIONS

Molly et al., Development of a S-step multi-chamber reactor as a simulation of the human intestinal microbial ecosystem, Appl. Microbiol. Biotech. (1993) 39(2): 254-258 ("Molly (1993)").

Narushima et al., Characterization of the 17 strains of regulatory T cell-inducing human-derived Clostridia, Gut Microbes (2014) 5(3): 333-339 ("Narushima (2014)").

Noor et al., Ulcerative colitis and irritable bowel patients exhibit distinct abnormalities of the gut microbiota, BMC Gastroenterol. (2010) 10: 134 ("Noor (2010)").

Patel et al., Food and Health Applications of Exopolysaccharides produced by Lactic acid Bacteria, Adv. Dairy Res. (2013) 1(2): 1-7 ("Patel (2013)").

Stankowski et al., Location of the O-Acetyl Group in Welan by the Reductive-Cleavage Method, Carbohydr. Res. (1992) 224: 337-341 ("Stankowski (1992)").

Sworn G., Gellan Gum, Chapter 9 (pp. 204-227) in Handbook of Hydrocolloids (2nd. Ed.), (2009) Woodhead Publishing Series in Food Science, Technology and Nutrition ("Sworn (2009)").

Tetsuguchi et al, Effects of Curdlan and Gellan Gum on the Surface Structure of Intestinal Mucosa in Rats, J. Nutr. Sci. Vitaminol. (1997) 43(5): 515-527 ("Tetsuguchi (1997").

Van de Wiele et al., The Simulator of the Human Intestinal Microbial Ecosystem (SHIME®), Chapt. 27 (pp. 305-318) in the Impact of Food Bioactives on Health (Verhoeckx et al. Eds.) 2013: Springer, New York ("Van de Wiele (2013)").

Van den Abbeele et al., Butyrate-producing Clostridium cluster XIVa species specifically colonize mucins in an in vitro gut model, ISME J. (2013) 6(4):335-340 ("Van den Abbeele (2013)").

Van den Abbeele et al., Incorporating a mucosal environment in a dynamic gut model results in a more representative colonization by lactobacilli, Environ. Microbiol. (2011) 13(10): 2667-2680 ("Van den Abbeele (2011)").

Zitomersky et al., Characterization of Adherent Bacteroidales from Intestinal Biopsies of Children and Young Adults with Inflammatory Bowel Disease, PLoS One (2013) 8(6): e63686, ("Zitomersky (2013)").

Supplemental International Search Report & Written Opinion Issued in PCT Patent Application No. PCT/US2020/013742, dated Oct. 2, 2020; 24 Pages.

NithyaBalaSundar et al., "Characterization of microbial polysaccharides and prebiotic enrichment of wheat bread with pullulan," Food Science and Technology (2020) 122: 1-7 (available online Jan. 2, 2020).

Hashimoto et al., "Microbial System for Polysaccharide Depolymerization: Enzymatic Route for Gellan Depolymerization by Bacillussp. GL1," Archives of Biochemistry and Biophysics (1997) 339(1): 17-23.

Gonclaves et al., "Structural analysis of gellans produced by Sphingomonas elodea strains by electrospray tandem mass spectrometry," Carbohydrate Polymers (2009) 77(1): 10-19.

Freitas et al., "Advances in bacterial exopolysaccharides: from production to biotechnological applications," Trends in Biotechnology (2011) 29(8): 388-398.

Douglas et al., "Composites of gellan gum hydrogel enzymatically mineralized with calcium-zinc phosphate for bone regeneration with antibacterial activity," J. Regen. Med. Tissue Eng. (2017) 102: 129-138.

Redouan et al., "Evaluation of antioxidant capacity of ulvan-like polymer obtained by regioselective oxidation of gellan exopolysaccharide," Food Chem. (2011) 127: 976-983.

Chandrasekaran et al, Roles of potassim ions, acetyl and L-glyceryl groups in native gellan double helix: an X-ray study, Carbohydrate Research (1992) 224: 1-17.

Meyer et al. Biotechnological Production of Oligosaccharides—Applications in the Food Industry. (2015); doi://10.5772/60934.

Kao et al., The influence of prebiotics on neurobiology and behavior, International Review of Neurobiology 131, 21-48; doi://10.1016/bs.irn.2016.08.007.

* cited by examiner

|  |  | Donor A | | | | | Donor B | | | | | Donor C | | | | |
|---|---|---|---|---|---|---|---|---|---|---|---|---|---|---|---|---|
|  |  | C1 | C2 | TR1 | TR2 | TR3 | C1 | C2 | TR1 | TR2 | TR3 | C1 | C2 | TR1 | TR2 | TR3 |
| Lumen | PC | 4.3 | 5.1 | 3.7 | 3.8 | 3.9 | 4.9 | 4.9 | 3.7 | 4.4 | 3.9 | 3.7 | 5.8 | 5.3 | 7.3 | 4.4 |
|  | DC | 13.4 | 13.5 | 12.5 | 15.5 | 14.9 | 10.0 | 5.8 | 10.9 | 8.0 | 8.8 | 13.1 | 12.0 | 14.0 | 12.3 | 13.6 |
| Mucus | PC | 3.8 |  | 11.2 | 5.3 | 6.6 | 4.4 | 2.9 | 3.5 | 4.8 | 5.2 | 3.3 | 3.4 | 9.9 | 5.4 | 11.8 |
|  | DC | 11.2 | 6.3 | 13.6 | 11.7 | 8.9 | 5.4 | 6.7 | 6.4 | 12.5 | 7.7 | 7.6 | 9.0 | 15.5 | 10.7 | 12.3 |

FIG. 8

|  | Donor A ||||| Donor B ||||| Donor C |||||
| --- | --- | --- | --- | --- | --- | --- | --- | --- | --- | --- | --- | --- | --- | --- | --- |
| PC Lumen | C1 | C2 | TR1 | TR2 | TR3 | C1 | C2 | TR1 | TR2 | TR3 | C1 | C2 | TR1 | TR2 | TR3 |
| Verrucomicrobia | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Synergistetes | 0.0 | 0.0 | 0.0 | 0.0 | 0.0 | 0.0 | 0.0 | 0.0 | 0.0 | 0.0 | 0.0 | 0.0 | 0.1 | 0.0 | 0.3 |
| Proteobacteria | 1.3 | 7.5 | 6.0 | 5.8 | 8.0 | 1.0 | 8.8 | 12.2 | 15.6 | 8.9 | 3.9 | 11.4 | 10.1 | 20.4 | 15.2 |
| Lentisphaerae | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Firmicutes | 41.9 | 41.0 | 21.7 | 18.5 | 23.0 | 40.1 | 40.7 | 33.6 | 21.2 | 27.7 | 53.7 | 43.8 | 46.1 | 34.4 | 20.4 |
| Bacteroidetes | 32.7 | 10.6 | 14.6 | 7.9 | 4.0 | 39.7 | 6.9 | 0.3 | 3.2 | 2.2 | 6.1 | 6.5 | 1.7 | 0.5 | 1.1 |
| Actinobacteria | 24.1 | 40.9 | 57.7 | 67.8 | 64.9 | 19.2 | 43.5 | 53.9 | 60.0 | 61.1 | 36.3 | 38.3 | 42.0 | 44.7 | 63.1 |
| DC Lumen | C1 | C2 | TR1 | TR2 | TR3 | C1 | C2 | TR1 | TR2 | TR3 | C1 | C2 | TR1 | TR2 | TR3 |
| Verrucomicrobia | 1.2 | 0.8 | 1.0 | 1.5 | 1.3 | 0.1 | 0.1 | 0.1 | 0.0 | 0.0 | 0.1 | 0.0 | 0.0 | 0.0 | 0.0 |
| Synergistetes | 7.6 | 6.2 | 20.7 | 15.9 | 12.4 | 13.0 | 16.7 | 20.5 | 13.7 | 17.4 | 6.7 | 7.8 | 16.1 | 11.8 | 18.8 |
| Proteobacteria | 2.4 | 2.3 | 2.0 | 1.9 | 3.7 | 1.6 | 3.2 | 1.0 | 1.6 | 2.3 | 1.7 | 4.6 | 4.4 | 3.2 | 5.5 |
| Lentisphaerae | 0.0 | 0.0 | 0.0 | 0.6 | 0.1 | 0.0 | 0.0 | 0.0 | 0.1 | 0.0 | 0.0 | 0.0 | 0.1 | 0.2 | 0.0 |
| Firmicutes | 40.1 | 37.6 | 29.4 | 29.3 | 30.3 | 38.9 | 28.2 | 33.8 | 32.7 | 30.9 | 44.9 | 38.8 | 32.0 | 40.8 | 33.1 |
| Bacteroidetes | 46.9 | 51.7 | 39.4 | 38.4 | 36.8 | 43.6 | 50.1 | 33.0 | 43.5 | 36.4 | 43.1 | 46.2 | 36.7 | 32.1 | 29.9 |
| Actinobacteria | 1.6 | 1.2 | 7.4 | 11.5 | 15.3 | 2.7 | 1.7 | 11.4 | 8.2 | 12.9 | 3.4 | 2.4 | 10.6 | 11.9 | 12.7 |
| PC Mucus | C1 | C2 | TR1 | TR2 | TR3 | C1 | C2 | TR1 | TR2 | TR3 | C1 | C2 | TR1 | TR2 | TR3 |
| Verrucomicrobia | 0.0 |  | 0.0 | 0.0 | 0.0 | 0.0 | 0.0 | 0.0 | 0.0 | 0.0 | 0.0 | 0.0 | 0.0 | 0.1 | 0.0 |
| Synergistetes | 0.0 |  | 0.0 | 0.0 | 0.4 | 0.0 | 0.0 | 0.0 | 0.1 | 0.0 | 0.0 | 0.0 | 0.4 | 38.5 | 3.2 |
| Proteobacteria | 1.2 |  | 15.4 | 4.9 | 15.8 | 1.3 | 0.2 | 2.1 | 7.6 | 6.2 | 2.1 | 0.8 | 23.4 | 1.8 | 7.8 |
| Lentisphaerae | 0.0 |  | 0.0 | 0.0 | 0.0 | 0.0 | 0.0 | 0.0 | 0.0 | 0.0 | 0.0 | 0.0 | 0.0 | 0.3 | 0.0 |
| Firmicutes | 54.6 |  | 40.8 | 32.8 | 39.7 | 53.5 | 24.5 | 32.4 | 29.2 | 44.1 | 46.5 | 35.4 | 37.4 | 41.9 | 50.6 |
| Bacteroidetes | 13.4 |  | 27.3 | 11.2 | 9.0 | 9.7 | 21.1 | 10.1 | 6.1 | 2.7 | 1.8 | 14.1 | 11.1 | 11.5 | 4.8 |
| Actinobacteria | 30.8 |  | 16.5 | 51.1 | 35.1 | 35.4 | 54.2 | 55.5 | 56.9 | 46.9 | 49.6 | 49.7 | 27.7 | 5.6 | 33.6 |
| DC Mucus | C1 | C2 | TR1 | TR2 | TR3 | C1 | C2 | TR1 | TR2 | TR3 | C1 | C2 | TR1 | TR2 | TR3 |
| Verrucomicrobia | 1.8 | 0.2 | 0.0 | 0.7 | 0.2 | 0.1 | 0.0 | 0.0 | 0.0 | 0.0 | 0.1 | 0.0 | 0.0 | 0.0 | 0.0 |
| Synergistetes | 23.9 | 37.4 | 18.8 | 21.3 | 27.7 | 38.5 | 35.7 | 36.6 | 21.4 | 26.7 | 27.8 | 27.6 | 17.1 | 24.9 | 17.7 |
| Proteobacteria | 8.0 | 1.9 | 5.5 | 15.5 | 6.5 | 1.8 | 4.4 | 2.1 | 3.1 | 3.2 | 5.1 | 11.7 | 12.5 | 2.9 | 7.7 |
| Lentisphaerae | 0.0 | 0.0 | 0.0 | 0.8 | 4.5 | 0.3 | 0.2 | 0.2 | 0.1 | 0.1 | 0.9 | 0.2 | 0.2 | 1.0 | 1.1 |
| Firmicutes | 46.6 | 34.4 | 33.1 | 31.5 | 37.5 | 41.9 | 36.8 | 45.6 | 46.8 | 54.8 | 41.3 | 37.2 | 52.8 | 43.1 | 56.7 |
| Bacteroidetes | 14.0 | 23.7 | 29.9 | 18.2 | 14.3 | 11.5 | 21.4 | 12.8 | 15.3 | 10.8 | 11.2 | 18.6 | 11.5 | 15.6 | 10.2 |
| Actinobacteria | 5.7 | 2.3 | 12.7 | 12.0 | 9.3 | 5.6 | 1.3 | 2.5 | 13.0 | 4.2 | 13.3 | 4.6 | 5.8 | 12.4 | 6.5 |

FIG. 9

| Phylum | Family | PC - Lumen | | | | | | | | | | | | | | | | | |
|---|---|---|---|---|---|---|---|---|---|---|---|---|---|---|---|---|---|---|
| | | Donor A | | | | | Donor B | | | | | Donor C | | | | | |
| | | C1 | C2 | TR1 | TR2 | TR3 | C1 | C2 | TR1 | TR2 | TR3 | C1 | C2 | TR1 | TR2 | TR3 |
| Actinobacteria | Bifidobacteriaceae | 22.6% | 22.3% | 46.4% | 32.4% | 43.9% | 17.5% | 25.2% | 46.9% | 40.4% | 42.9% | 34.0% | 26.6% | 27.3% | 21.0% | 41.1% |
| | Coriobacteriaceae | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% |
| | Microbacteriaceae | 0.0% | 0.0% | 0.0% | 0.0% | 0.0% | 0.0% | 0.0% | 0.0% | 0.2% | 0.3% | 0.0% | 0.2% | 0.0% | 0.0% | 0.1% |
| | Micrococcaceae | 1.5% | 18.6% | 11.3% | 23.4% | 22.0% | 1.7% | 18.3% | 7.0% | 19.3% | 17.8% | 2.3% | 11.7% | 14.6% | 23.3% | 21.1% |
| Bacteroidetes | Bacteroidaceae | 32.7% | 10.6% | 14.6% | 7.9% | 4.0% | 19.7% | 6.9% | 0.3% | 3.2% | 2.1% | 6.1% | 6.4% | 1.7% | 0.4% | 1.1% |
| | Bacteroidales_S24-7 group | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% |
| | Porphyromonadaceae | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% |
| | Prevotellaceae | 0.0% | 0.0% | 0.0% | 0.0% | 0.0% | 0.0% | 0.0% | 0.0% | 0.0% | 0.0% | 0.0% | 0.1% | 0.0% | 0.0% | 0.0% |
| | Rikenellaceae | 0.0% | 0.0% | 0.0% | 0.0% | 0.0% | 0.0% | 0.0% | 0.0% | 0.0% | 0.0% | 0.0% | 0.1% | 0.0% | 0.0% | 0.0% |
| Firmicutes | Acidaminococcaceae | 0.0% | 0.0% | 0.0% | 0.0% | 0.0% | 0.0% | 0.0% | 0.0% | 0.0% | 0.0% | 0.2% | 0.1% | 0.7% | 9.9% | 1.0% |
| | Christensenellaceae | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% |
| | Clostridiaceae_1 | 0.1% | 0.0% | 0.3% | 0.2% | 0.2% | 0.0% | 0.1% | 0.4% | 0.4% | 0.3% | 0.0% | 0.0% | 0.0% | 0.0% | 0.0% |
| | Enterococcaceae | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% |
| | Erysipelotrichaceae | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% |
| | Eubacteriaceae | 0.0% | 0.0% | 0.0% | 0.0% | 0.0% | 0.0% | 0.0% | 0.1% | 0.3% | 0.6% | 0.9% | 0.6% | 0.2% | 0.1% | 1.0% |
| | Family_XIII | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% |
| | Lachnospiraceae | 5.4% | 0.8% | 1.0% | 0.6% | 1.2% | 5.6% | 0.1% | 32.9% | 20.5% | 26.9% | 20.3% | 43.1% | 45.1% | 24.3% | 18.4% |
| | Ruminococcaceae | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% |
| | Veillonellaceae | 33.4% | 40.1% | 20.4% | 17.7% | 21.7% | 34.4% | 40.5% | 32.9% | 20.5% | 26.9% | 20.3% | 43.1% | 45.1% | 24.3% | 18.4% |
| Lentisphaerae | Victivallaceae | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% |
| Proteobacteria | Alcaligenaceae | 0.0% | 0.4% | 0.1% | 0.0% | 0.3% | 0.1% | 1.0% | 0.7% | 0.7% | 0.6% | 0.3% | 1.4% | 0.6% | 1.8% | 0.8% |
| | Desulfovibrionaceae | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% |
| | Enterobacteriaceae | 1.1% | 1.2% | 4.5% | 2.5% | 3.0% | 0.1% | 0.5% | 2.0% | 2.2% | 1.8% | 0.6% | 0.9% | 2.4% | 3.6% | 1.2% |
| | Pseudomonadaceae | 0.1% | 5.8% | 1.2% | 2.4% | 2.3% | 0.3% | 5.9% | 5.5% | 10.0% | 3.7% | 2.7% | 8.0% | 6.3% | 10.4% | 5.7% |
| | Rhodospirillaceae | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% |
| | Xanthomonadaceae | 0.1% | 0.1% | 0.2% | 0.8% | 2.3% | 0.5% | 1.4% | 1.0% | 1.9% | 2.8% | 0.2% | 1.1% | 0.8% | 4.6% | 7.5% |
| Synergistetes | Synergistaceae | 0.0% | 0.0% | 0.0% | 0.0% | 0.0% | 0.0% | 0.0% | 0.0% | 0.0% | 0.0% | 0.0% | 0.0% | 0.1% | 0.0% | 0.7% |
| Verrucomicrobia | Verrucomicrobiaceae | 0.0% | 0.0% | 0.0% | 0.0% | 0.0% | 0.0% | 0.0% | 0.0% | 0.0% | 0.0% | 0.0% | 0.0% | 0.0% | 0.0% | 0.0% |

FIG. 10

| Phylum | Family | DC - Lumen ||||||||||||||||
| | | Donor A |||||| Donor B |||||| Donor C ||||||
| | | C1 | C2 | TR1 | TR2 | TR3 | C1 | C2 | TR1 | TR2 | TR3 | C1 | C2 | TR1 | TR2 | TR3 |
|---|---|---|---|---|---|---|---|---|---|---|---|---|---|---|---|---|
| Actinobacteria | Bifidobacteriaceae | 1.5% | 0.5% | 5.9% | 6.4% | 11.6% | 2.5% | 1.3% | 10.5% | 5.4% | 11.1% | 3.3% | 2.0% | 7.1% | 7.7% | 8.9% |
| | Coriobacteriaceae | 0.1% | 0.1% | 0.0% | 0.1% | 0.1% | 0.1% | 0.1% | 0.2% | 0.1% | 0.1% | 0.1% | 0.0% | 0.1% | 0.0% | 0.0% |
| | Microbacteriaceae | 0.0% | 0.0% | 0.0% | 0.0% | 0.0% | 0.0% | 0.0% | 0.0% | 0.0% | 0.1% | 0.0% | 0.0% | 0.0% | 0.0% | 0.2% |
| | Micrococcaceae | 0.1% | 0.5% | 1.5% | 5.0% | 3.6% | 0.0% | 0.3% | 0.7% | 2.6% | 1.6% | 0.1% | 0.5% | 3.4% | 4.1% | 3.5% |
| Bacteroidetes | Bacteroidaceae | 33.8% | 30.0% | 29.7% | 33.4% | 26.3% | 36.5% | 35.1% | 27.8% | 39.2% | 29.3% | 32.7% | 36.5% | 29.3% | 27.7% | 23.2% |
| | Bacteroidales_S24-7_group | 0.0% | 0.0% | 0.0% | 0.0% | 0.0% | 0.0% | 0.2% | 0.1% | 0.0% | 0.0% | 0.0% | 1.8% | 0.1% | 0.1% | 0.0% |
| | Porphyromonadaceae | 12.6% | 4.8% | 9.4% | 4.7% | 9.4% | 6.9% | 4.3% | 4.2% | 3.7% | 6.5% | 8.9% | 5.0% | 3.8% | 3.1% | 6.1% |
| | Prevotellaceae | 0.0% | 0.0% | 0.0% | 0.0% | 0.0% | 0.0% | 0.1% | 0.3% | 0.2% | 0.1% | 0.1% | 0.4% | 0.7% | 0.9% | 0.2% |
| | Rikenellaceae | 0.6% | 1.0% | 0.4% | 1.1% | 1.1% | 0.2% | 0.4% | 0.6% | 0.2% | 0.5% | 1.4% | 2.9% | 1.7% | 0.4% | 0.3% |
| Firmicutes | Acidaminococcaceae | 1.3% | 1.1% | 1.8% | 1.1% | 3.9% | 1.0% | 1.0% | 1.8% | 1.1% | 2.4% | 1.5% | 1.6% | 1.9% | 0.9% | 3.7% |
| | Christensenellaceae | 0.0% | 0.0% | 0.0% | 0.0% | 0.0% | 0.0% | 0.0% | 0.0% | 0.0% | 0.0% | 0.0% | 0.1% | 0.0% | 0.0% | 0.0% |
| | Clostridiaceae_1 | 0.0% | 0.0% | 0.0% | 0.0% | 0.0% | 0.0% | 0.0% | 0.1% | 0.1% | 0.0% | 0.1% | 0.1% | 0.1% | 0.1% | 0.0% |
| | Enterococcaceae | 0.0% | 0.0% | 0.0% | 0.1% | 0.0% | 0.1% | 0.0% | 0.1% | 0.0% | 0.0% | 0.0% | 0.0% | 0.0% | 0.1% | 0.3% |
| | Erysipelotrichaceae | 0.0% | 0.0% | 0.0% | 0.1% | 0.4% | 0.0% | 0.0% | 0.1% | 0.1% | 0.1% | 0.1% | 0.1% | 0.1% | 0.1% | 0.0% |
| | Eubacteriaceae | 0.0% | 0.0% | 0.1% | 0.1% | 0.0% | 0.0% | 0.0% | 0.0% | 0.0% | 0.1% | 0.1% | 0.2% | 0.0% | 0.2% | 0.4% |
| | Family_XIII | 0.0% | 0.0% | 0.0% | 0.0% | 0.0% | 0.0% | 0.0% | 0.0% | 0.0% | 0.0% | 0.0% | 0.0% | 0.0% | 0.0% | 0.1% |
| | Lachnospiraceae | 29.3% | 30.0% | 21.3% | 22.5% | 19.7% | 32.3% | 19.2% | 23.5% | 22.4% | 23.3% | 36.1% | 30.6% | 25.0% | 33.3% | 24.8% |
| | Ruminococcaceae | 1.6% | 2.1% | 2.7% | 3.3% | 0.9% | 1.0% | 1.8% | 6.8% | 1.8% | 0.9% | 0.4% | 0.3% | 0.6% | 1.8% | 0.6% |
| | Veillonellaceae | 4.1% | 4.3% | 3.5% | 1.7% | 8.3% | 4.2% | 6.0% | 1.6% | 1.8% | 4.0% | 0.7% | 6.1% | 4.2% | 1.4% | 4.1% |
| Lentisphaerae | Victivallaceae | 0.0% | 0.0% | 0.0% | 0.0% | 0.1% | 0.0% | 0.0% | 0.1% | 0.1% | 0.0% | 0.0% | 0.0% | 0.1% | 0.2% | 0.0% |
| Proteobacteria | Alcaligenaceae | 0.5% | 0.2% | 0.3% | 0.5% | 0.7% | 0.6% | 0.2% | 0.1% | 0.1% | 0.2% | 0.2% | 0.4% | 0.4% | 0.3% | 0.6% |
| | Desulfovibrionaceae | 0.3% | 0.3% | 0.3% | 0.2% | 0.7% | 0.0% | 0.1% | 0.3% | 0.1% | 0.1% | 0.2% | 0.2% | 0.2% | 0.1% | 0.5% |
| | Enterobacteriaceae | 0.0% | 0.0% | 0.0% | 0.1% | 0.2% | 0.0% | 0.2% | 0.3% | 0.1% | 0.1% | 0.2% | 0.1% | 0.1% | 0.3% | 4.7% |
| | Pseudomonadaceae | 1.5% | 1.8% | 1.3% | 0.9% | 2.1% | 0.8% | 0.9% | 0.4% | 1.0% | 1.2% | 1.2% | 4.4% | 3.0% | 2.2% | 4.3% |
| | Rhodospirillaceae | 0.0% | 0.0% | 0.0% | 0.0% | 0.0% | 0.0% | 2.0% | 0.2% | 0.0% | 0.0% | 0.0% | 0.2% | 0.5% | 0.1% | 0.0% |
| | Xanthomonadaceae | 0.0% | 0.0% | 0.0% | 0.2% | 0.0% | 0.1% | 0.1% | 0.1% | 0.1% | 0.2% | 0.0% | 0.2% | 0.1% | 0.3% | 0.6% |
| Synergistetes | Synergistaceae | 7.6% | 6.2% | 20.1% | 15.9% | 12.4% | 13.0% | 16.7% | 19.3% | 13.7% | 17.4% | 6.7% | 7.8% | 16.1% | 11.8% | 18.1% |
| Verrucomicrobia | Verrucomicrobiaceae | 1.2% | 0.8% | 1.0% | 1.3% | 1.3% | 0.1% | 0.1% | 0.1% | 0.0% | 0.0% | 0.1% | 0.0% | 0.0% | 0.0% | 0.0% |

FIG. 11

| Phylum | Family | PC - Mucus | | | | | | | | | | | | | | | | | | |
|---|---|---|---|---|---|---|---|---|---|---|---|---|---|---|---|---|---|---|---|
| | | Donor A | | | | | | Donor B | | | | | | Donor C | | | | | |
| | | C1 | C2 | TR1 | TR2 | TR3 | | C1 | C2 | TR1 | TR2 | TR3 | | C1 | C2 | TR1 | TR2 | TR3 | |
| Actinobacteria | Bifidobacteriaceae | 30.4% | | 13.5% | 37.3% | 29.6% | | 34.8% | 53.3% | 49.9% | 39.9% | 38.5% | | 48.8% | 49.4% | 23.0% | 4.7% | 26.6% | |
| | Coriobacteriaceae | 0.0% | | 0.0% | 0.0% | 0.3% | | 0.0% | 0.0% | 0.0% | 0.0% | 0.1% | | 0.1% | 0.0% | 0.0% | 0.9% | 1.1% | |
| | Microbacteriaceae | 0.0% | | 0.0% | 0.0% | 0.0% | | 0.0% | 0.0% | 0.0% | 0.0% | 0.3% | | 0.0% | 0.0% | 0.0% | 0.0% | 0.0% | |
| | Micrococcaceae | 0.4% | | 3.0% | 13.3% | 5.2% | | 0.6% | 0.4% | 5.5% | 10.0% | 7.9% | | 0.7% | 0.3% | 4.7% | 0.1% | 5.2% | |
| Bacteroidetes | Bacteroidaceae | 13.4% | | 9.7% | 11.2% | 8.9% | | 9.5% | 21.1% | 9.9% | 6.0% | 2.6% | | 1.7% | 14.0% | 10.8% | 6.5% | 3.6% | |
| | Bacteroidales_S24-7 group | 0.0% | | 0.0% | 0.0% | 0.0% | | 0.0% | 0.0% | 0.0% | 0.0% | 0.0% | | 0.0% | 0.0% | 0.0% | 0.2% | 0.0% | |
| | Porphyromonadaceae | 0.0% | | 0.0% | 0.0% | 0.0% | | 0.0% | 0.0% | 0.0% | 0.0% | 0.1% | | 0.0% | 0.0% | 0.1% | 1.0% | 1.2% | |
| | Prevotellaceae | 0.0% | | 0.0% | 0.0% | 0.0% | | 0.0% | 0.0% | 0.0% | 0.0% | 0.0% | | 0.0% | 0.0% | 0.0% | 0.0% | 0.0% | |
| | Rikenellaceae | 0.0% | | 0.0% | 0.0% | 0.0% | | 0.0% | 0.0% | 0.0% | 0.0% | 0.0% | | 0.0% | 0.0% | 0.0% | 0.0% | 0.0% | |
| Firmicutes | Acidaminococcaceae | 0.0% | | 0.0% | 0.0% | 0.0% | | 0.0% | 0.0% | 0.0% | 0.0% | 0.0% | | 0.0% | 0.0% | 0.0% | 0.8% | 1.3% | |
| | Christensenellaceae | 0.0% | | 0.0% | 0.0% | 0.0% | | 0.0% | 0.0% | 0.0% | 0.0% | 0.0% | | 0.0% | 0.0% | 0.0% | 0.0% | 0.0% | |
| | Clostridiaceae 1 | 0.0% | | 3.5% | 0.0% | 1.5% | | 0.0% | 0.0% | 1.3% | 0.2% | 0.2% | | 0.2% | 0.0% | 0.1% | 1.0% | 3.3% | |
| | Enterococcaceae | 0.1% | | 3.4% | 0.7% | 2.7% | | 0.0% | 0.0% | 0.1% | 0.4% | 0.3% | | 0.0% | 0.0% | 1.3% | 0.1% | 2.1% | |
| | Erysipelotrichaceae | 0.0% | | 0.0% | 0.0% | 0.0% | | 0.0% | 0.0% | 0.0% | 0.0% | 0.0% | | 0.0% | 0.0% | 0.0% | 1.1% | 0.0% | |
| | Eubacteriaceae | 0.0% | | 0.0% | 0.0% | 0.0% | | 0.0% | 0.0% | 0.0% | 0.0% | 0.0% | | 0.2% | 0.0% | 0.0% | 0.0% | 0.0% | |
| | Family XIII | 0.0% | | 0.0% | 0.0% | 0.0% | | 0.0% | 0.0% | 0.0% | 0.0% | 0.0% | | 0.0% | 0.0% | 0.0% | 0.0% | 0.0% | |
| | Lachnospiraceae | 20.9% | | 20.2% | 16.0% | 25.8% | | 20.7% | 3.9% | 0.5% | 4.0% | 18.0% | | 4.6% | 1.3% | 6.2% | 35.9% | 24.5% | |
| | Ruminococcaceae | 0.0% | | 0.0% | 0.0% | 0.0% | | 0.0% | 0.0% | 0.0% | 0.0% | 0.0% | | 0.0% | 0.0% | 0.0% | 3.3% | 0.1% | |
| | Veillonellaceae | 16.3% | | 13.6% | 16.1% | 9.5% | | 32.8% | 20.6% | 30.5% | 24.6% | 25.5% | | 41.6% | 34.1% | 29.8% | 1.3% | 18.5% | |
| Lentisphaerae | Victivallaceae | 0.0% | | 0.0% | 0.0% | 0.0% | | 0.0% | 0.0% | 0.0% | 0.0% | 0.0% | | 0.0% | 0.0% | 0.0% | 0.2% | 0.0% | |
| Proteobacteria | Alcaligenaceae | 0.0% | | 0.0% | 0.1% | 0.2% | | 0.6% | 0.0% | 0.6% | 0.6% | 0.1% | | 0.3% | 0.6% | 0.9% | 0.2% | 0.2% | |
| | Desulfovibrionaceae | 0.0% | | 0.0% | 0.1% | 0.3% | | 0.0% | 0.1% | 0.0% | 0.0% | 0.0% | | 0.0% | 0.0% | 0.0% | 1.3% | 0.1% | |
| | Enterobacteriaceae | 1.0% | | 5.0% | 2.7% | 9.8% | | 0.1% | 0.0% | 0.3% | 3.1% | 3.4% | | 0.5% | 0.0% | 11.9% | 0.6% | 6.1% | |
| | Pseudomonadaceae | 0.2% | | 0.2% | 1.4% | 5.5% | | 0.1% | 0.0% | 0.8% | 2.7% | 1.5% | | 1.0% | 0.2% | 3.8% | 0.3% | 0.7% | |
| | Rhodospirillaceae | 0.0% | | 0.0% | 0.0% | 0.0% | | 0.0% | 0.0% | 0.0% | 0.0% | 0.0% | | 0.0% | 0.0% | 0.0% | 0.0% | 0.0% | |
| | Xanthomonadaceae | 0.0% | | 0.1% | 0.4% | 0.0% | | 0.0% | 0.0% | 0.1% | 0.0% | 1.1% | | 0.0% | 0.0% | 2.2% | 0.1% | 0.5% | |
| Synergistetes | Synergistaceae | 0.0% | | 0.0% | 0.0% | 0.0% | | 0.0% | 0.0% | 0.0% | 0.1% | 0.0% | | 0.0% | 0.0% | 0.4% | 3.5% | 3.2% | |
| Verrucomicrobia | Verrucomicrobiaceae | 0.0% | | 0.0% | 0.0% | 0.0% | | 0.0% | 0.0% | 0.0% | 0.0% | 0.0% | | 0.0% | 0.0% | 0.0% | 0.1% | 0.0% | |

FIG. 12

| Phylum | Family | DC - Mucus |||||||||||||||||||
|---|---|---|---|---|---|---|---|---|---|---|---|---|---|---|---|---|---|---|---|
| | | Donor A |||||| Donor B |||||| Donor C ||||||
| | | C1 | C2 | TR1 | TR2 | TR3 | C1 | C2 | TR1 | TR2 | TR3 | C1 | C2 | TR1 | TR2 | TR3 |
| Actinobacteria | Bifidobacteriaceae | 3.3% | 1.8% | 9.8% | 8.6% | 7.8% | 4.7% | 1.0% | 1.4% | 10.1% | 2.0% | 10.1% | 3.6% | 4.6% | 10.3% | 4.5% |
| | Coriobacteriaceae | 2.3% | 0.4% | 0.0% | 0.2% | 0.2% | 0.8% | 0.2% | 0.9% | 0.4% | 1.1% | 2.2% | 0.8% | 0.8% | 0.2% | 0.7% |
| | Microbacteriaceae | 0.0% | 0.0% | 0.2% | 0.0% | 0.0% | 0.0% | 0.0% | 0.0% | 0.0% | 0.1% | 0.0% | 0.0% | 0.0% | 0.0% | 0.1% |
| | Micrococcaceae | 0.1% | 0.1% | 3.5% | 3.2% | 1.3% | 0.1% | 0.1% | 0.2% | 2.5% | 1.0% | 0.1% | 0.1% | 0.4% | 1.9% | 1.2% |
| Bacteroidetes | Bacteroidaceae | 11.4% | 20.2% | 13.3% | 16.5% | 11.7% | 6.5% | 12.7% | 7.2% | 12.3% | 5.3% | 7.3% | 13.4% | 7.5% | 12.7% | 4.3% |
| | Bacteroidales_S24-7_group | 0.0% | 0.0% | 0.0% | 0.0% | 0.0% | 0.2% | 0.2% | 0.3% | 0.3% | 0.4% | 0.1% | 0.1% | 0.0% | 0.2% | 0.3% |
| | Porphyromonadaceae | 1.9% | 2.1% | 6.1% | 1.1% | 1.9% | 4.0% | 10.6% | 4.2% | 2.1% | 4.4% | 2.5% | 3.4% | 2.9% | 1.8% | 4.7% |
| | Prevotellaceae | 0.0% | 0.0% | 0.2% | 0.0% | 0.0% | 0.0% | 0.0% | 0.0% | 0.3% | 0.0% | 0.0% | 0.0% | 0.0% | 0.2% | 0.0% |
| | Rikenellaceae | 0.8% | 1.4% | 0.3% | 0.7% | 0.7% | 0.8% | 0.7% | 0.9% | 0.3% | 0.6% | 1.3% | 1.6% | 1.1% | 0.6% | 0.8% |
| | Acidaminococcaceae | 1.1% | 1.5% | 2.2% | 0.9% | 0.7% | 0.8% | 1.6% | 1.7% | 1.6% | 1.6% | 1.1% | 0.7% | 1.3% | 1.5% | 1.6% |
| | Christensenellaceae | 0.1% | 0.0% | 0.0% | 0.1% | 0.1% | 0.0% | 0.0% | 0.0% | 0.0% | 0.5% | 0.1% | 0.0% | 0.0% | 0.0% | 0.2% |
| | Clostridiaceae 1 | 4.0% | 1.2% | 0.0% | 6.1% | 4.3% | 1.0% | 2.0% | 3.5% | 0.6% | 5.2% | 1.1% | 2.6% | 10.1% | 0.8% | 5.6% |
| | Enterococcaceae | 0.6% | 0.0% | 0.3% | 0.8% | 3.9% | 0.1% | 1.1% | 0.1% | 0.2% | 0.5% | 0.1% | 0.2% | 4.7% | 3.8% | 4.0% |
| Firmicutes | Erysipelotrichaceae | 0.5% | 0.3% | 0.0% | 0.2% | 0.1% | 0.1% | 0.3% | 0.3% | 0.2% | 0.1% | 0.1% | 0.1% | 0.2% | 0.0% | 0.1% |
| | Eubacteriaceae | 0.0% | 0.0% | 0.4% | 1.1% | 2.1% | 0.0% | 0.0% | 0.3% | 0.0% | 0.8% | 0.2% | 0.8% | 1.2% | 1.6% | 2.7% |
| | Family XIII | 0.1% | 0.2% | 0.1% | 0.1% | 0.1% | 0.2% | 0.2% | 0.2% | 0.1% | 0.1% | 0.3% | 0.3% | 0.3% | 0.1% | 0.2% |
| | Lachnospiraceae | 36.1% | 25.8% | 24.8% | 18.3% | 13.6% | 35.9% | 28.0% | 34.2% | 28.6% | 30.1% | 34.1% | 29.4% | 32.0% | 29.5% | 30.4% |
| | Ruminococcaceae | 2.8% | 4.4% | 0.6% | 3.0% | 2.4% | 2.3% | 2.4% | 4.4% | 1.5% | 5.9% | 1.9% | 1.7% | 2.3% | 2.6% | 2.3% |
| | Veillonellaceae | 1.1% | 0.7% | 4.1% | 0.8% | 0.2% | 1.3% | 1.3% | 1.4% | 4.1% | 0.2% | 2.1% | 1.3% | 0.5% | 1.1% | 0.5% |
| Lentisphaerae | Victivallaceae | 0.0% | 0.0% | 0.0% | 0.8% | 4.5% | 0.3% | 0.2% | 0.2% | 0.1% | 0.1% | 0.9% | 0.2% | 0.2% | 1.0% | 1.1% |
| | Alcaligenaceae | 0.4% | 0.4% | 0.6% | 0.2% | 0.5% | 0.2% | 0.2% | 0.2% | 0.2% | 0.5% | 0.6% | 0.4% | 0.2% | 0.3% | 0.3% |
| Proteobacteria | Desulfovibrionaceae | 0.9% | 0.9% | 0.5% | 0.2% | 0.4% | 0.7% | 1.6% | 1.1% | 0.5% | 0.6% | 0.7% | 1.0% | 0.4% | 0.2% | 0.4% |
| | Enterobacteriaceae | 1.9% | 0.5% | 0.7% | 1.4% | 3.0% | 0.6% | 2.2% | 0.3% | 0.8% | 0.3% | 3.2% | 3.3% | 3.5% | 1.2% | 0.7% |
| | Pseudomonadaceae | 4.1% | 0.2% | 3.3% | 1.3% | 2.7% | 0.3% | 0.1% | 0.0% | 1.2% | 1.5% | 0.4% | 2.0% | 3.7% | 0.8% | 6.0% |
| | Rhodospirillaceae | 0.0% | 0.0% | 0.0% | 0.0% | 0.0% | 0.0% | 0.4% | 1.4% | 0.3% | 0.0% | 0.1% | 0.1% | 0.2% | 0.3% | 0.1% |
| | Xanthomonadaceae | 0.0% | 0.0% | 0.0% | 0.0% | 0.0% | 0.1% | 0.0% | 0.0% | 0.0% | 0.0% | 0.1% | 0.0% | 0.0% | 0.0% | 0.1% |
| Synergistetes | Synergistaceae | 23.9% | 37.4% | 18.8% | 21.3% | 27.7% | 35.3% | 35.7% | 36.0% | 21.4% | 26.7% | 27.8% | 27.6% | 17.1% | 24.9% | 17.7% |
| Verrucomicrobia | Verrucomicrobiaceae | 1.8% | 0.2% | 0.0% | 0.6% | 0.1% | 0.1% | 0.0% | 0.0% | 0.0% | 0.0% | 0.1% | 0.0% | 0.0% | 0.0% | 0.0% |

FIG. 13

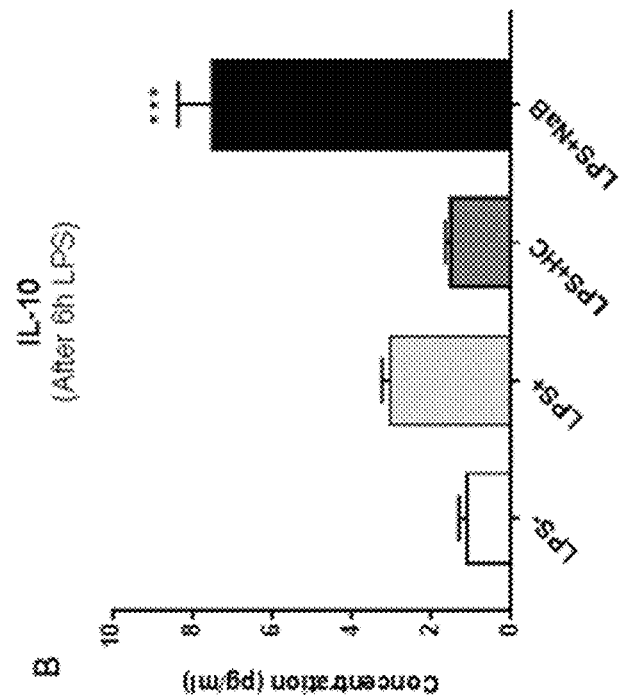
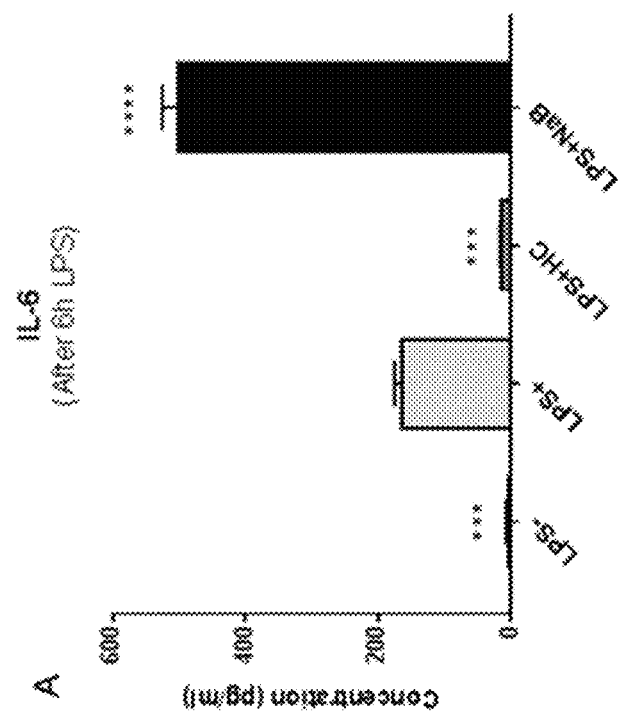
FIG. 19

PREBIOTIC COMPOSITION AND ITS USE

RELATED APPLICATIONS

The present application claims priority to U.S. Provisional Application No. 62/794,452, filed on Jan. 18, 2019, and U.S. Provisional Application No. 62/869,248, filed on Jul. 1, 2019.

FIELD OF THE INVENTION

Disclosed herein is an ingestible composition comprising a sphingan and its use as a prebiotic.

BACKGROUND

The human gastrointestinal tract is a highly complex microbial ecosystem which has been shown to be remarkably stable. (Zoetendal (1998).) Many different approaches have been used to modulate the gut flora in a way that is beneficial to host health. (See, e.g., Bielecka (2002) and Steer (2000).) These different approaches include the addition of living microorganisms to food (probiotics), the addition of food ingredients or dietary fiber to stimulate selectively beneficial bacteria within the host (prebiotics), and a combination of both probiotics and prebiotics (synbiotics).

Prebiotics are non-digestible substrates that are selectively used by the host micro-organisms conferring a health benefit. (Gibson (2017).) Prebiotic effects in the gut can be evaluated based on the growth of health promoting bacteria such as lactobacilli and bifidobacteria, the decrease in intestinal pathogens, and the increase or decrease in production of health-related bacterial metabolites. The prebiotic/bifidogenic nature of selected prebiotics (such as, inulin, fructo-oligosaccharides, galacto-oligosaccharides, lactulose, and an arabino-oligosaccharide) has been suggested and/or confirmed in previous studies. (See e.g., Guimaraes (2018), Karltohn-Senaye (2013), Patel (2013), Saavedra (2002), Tuohy (2001), Tuohy (2002), U.S. Pat. No. 8,313,789B2, US20100092440A1, and WO2004002240A2.)

Generally, sphingans are polysaccharides comprised of the following substituted or unsubstituted tetrameric saccharide depicted generally as [(→3)Glc($\beta$1→4)GlcA($\beta$1→4)Glc ($\beta$1→4)Rha($\alpha$1→)]n. Known sphingans include, for example, gellan (S-60), welan (S-130), rhamsan (S-194), and diutan (S-657).

Gellan (gellan gum or S-60) is produced by strains of the species *Sphingomonas elodea* (formerly *Pseudomonas elodea*), for example, strain ATCC 31461. (See. e.g., Morrison (2016), Sworn (2009), and U.S. Pat. No. 4,326,053A.) Common forms of gellan gum include, high acyl (aka native), unclarified (e.g., KELCOGEL® LT100 gellan), low acyl, unclarified (e.g., KELCOGEL® LT gellan), and low acyl, clarified (e.g., KELCOGEL® and KELCOGEL® F gellan gums). (Sworn (2009).) A number of specialty grades are also available, for example, high acyl, PHB-free, clarified (e.g., KELGOGEL® HT gellan) and low acyl, clarified (double-precipitated) (e.g., GELRITE™ MK gellan). The native, or high acyl, form of gellan includes two acyl substituents (acetate at $O^6$ and glycerate at $O^2$) on the (1→3)Glc-unit, and on average, there is one glycerate per tetramer and one acetate per two tetramers. (Kuo (1986).) In low acyl gellan, the glycerate and acetate are absent. Gellan gums can also be produced with an intermediate glycerate and acetate content. A commercial product with a reduced glycerate and acetate content is KELCOGEL® DGA gellan.

Gellan gum generally functions as a gelling or suspending agent in certain ingestible products and is present at levels that range from 0.02 to 0.5% w/v. (See, e.g., Fallourd (2009), Morrison (2016), Sworn (2009), U.S. Pat. No. 6,602,996B1, U.S. Pat. No. 6,663,911B2, U.S. Pat. No. 5,342,626A, US8513408B2, and US20080008814A1.) Prior to its approval as a food additive, studies evaluated the safety of gellan gum when administered to rats and humans. (See, e.g., Anderson (1988) and Edwards (1995); see also Anderson (1990).) For instance, Edwards (1995) describes feeding Wistar rats for 28-days a diet that included 50 g/kg/d of gellan gum. (As a point of reference, 50 g/kg in rats corresponds to a human equivalent amount of about 8 g/kg. (See, e.g., FDA Guidance (2005).) Interestingly, Edwards (1995) concluded that gellan gum had no consistent effect on cecal or fecal short-chain fatty acids (SCFAs, such as acetate, propionate, and butyrate). Further, Anderson (1988) describes a study where human volunteers ingested an amount of gellan gum according to a fixed dosing schedule of 175 mg/kg/d for 7-days, followed by 200 mg/kg/d for an additional 16-days. (For a human weight range of 60-kg to 75-kg, 175 mg/kg corresponds to a range of 10.5 to 13-g, while 200 mg/kg corresponds to a range of 12-g to 15-g.) Based on the results presented therein, Anderson (1988) concluded that ingestion of gellan gum caused no adverse dietary nor physiological effects. Further, Anderson (1988) concluded that gellan gum exhibited a fecal bulking effect. Consistent with the fecal bulking effect observed by Anderson (1988), a subsequent study showed that gellan gum reduces diarrhea in cats. (U.S. Pat. No. 9,028,861B2.) With reference to Tetsuguchi (1997), Li (2019) mentions without explanation or proof that a gellan oligosaccharide reportedly has intestinal prebiotic effects, even though Tetsuguchi (1997) plainly did not evaluate intestinal prebiotic effects of a gellan oligosaccharide. To date, no studies have demonstrated definitively whether gellan gum or an oligosaccharide derived from gellan gum functions as a prebiotic agent.

Welan (welan gum or S-130) is produced by *Sphingomonas* sp. (e.g., ATCC 31555). (U.S. Pat. Nos. 4,342,866A and 5,175,277A.) Approximately two-thirds of the welan (1→4) Glc-units are substituted at $O^3$ by a $\alpha$-L-rhamnopyranosyl group (i.e., Rha($\alpha$1→)), while the remainder of the welan (1→4)Glc-units are substituted by an $\alpha$-L-mannopyranosyl group (i.e., Man($\alpha$1→)). (Stankowski (1992).) Additionally, welan's (1→3)Glc-unit may be substituted at $O^2$ by an acetyl. (Stankowski (1992).)

Rhamsan (rhamsan gum or S-194) is produced by *Sphingomonas* sp. (e.g., ATCC 31961). (U.S. Pat. No. 4,401,760A.) Rhamsan is substituted at the $O^6$ position of the (1→3)Glc-unit by D-Glc($\beta$1→6)-D-Glc($\alpha$1→+). (Jansson (1986).) Rhamsan contains one O-acetyl group per repeating unit, distributed over secondary positions. (Jansson (1986).)

Diutan (diutan gum or S-657) is produced by *Sphingomonas* sp. (e.g., ATCC 53159). (U.S. Pat. No. 5,175,278A and US20130189748A1.) Diutan's (1→4)Glc-unit is substituted at $O^3$ by a Rha($\alpha$1→4)-Rha($\alpha$1→), at $O^6$ by an acetyl, and to a variable degree at the $O^2$ and/or $O^6$ positions of the (1→3)Glc-unit by an acetyl. (Diltz (2001).)

SUMMARY

Disclosed herein is an ingestible composition comprising a sphingan and its use as a prebiotic.

Abbreviations

The text that follows includes numerous abbreviated terms. Abbreviations for selected terms disclosed herein are identified below.

A: Donor A (female, 28 y)
Ac: Acetate
B: Donor B (female, 41 y)
b-SCFA: branched short-chain fatty acids (e.g., isobutyrate, isovalerate, and isocaproate)
C: Donor C (female, 34 y)
C1: Control Period 1
C2: Control Period 2
CON(ave): Average value concentration for control periods 1 and 2
CD: Crohn's disease
DC: Distal Colon Reactor
DP: Degree of polymerization
Glc: D-glucopyranosyl
GlcA: D-glucopyranosyluronic acid
Glyc: L-Glycerate
GPRs: G-protein coupled receptor
HA: High Acyl
HA/LA: High Acyl or Low Acyl
IBDs: inflammatory bowel diseases
IBS: irritable bowel syndrome
IFN: Interferon
IL: Interleukin
LA: Low Acyl
LCSs: Long-chain sphingans
LPS: Lipopolysaccharide
MAMPs: microbial associated molecular patterns
Man: L-mannopyranosyl
mM: milli-molar (i.e., milli-moles per liter)
MN: Number Average Molecular Weight
MW: Weight Average Molecular Weight
NaB: Sodium Butyrate
OTU: Operational Taxonomic Unit
PHB: Polyhydroxybutyrate
PC: Proximal Colon
PRRs: pattern recognition receptors
Rha: L-rhamnopyranosyl
ROS: Reactive Oxygen Species
SCFA: Short-chain fatty acids (e.g., acetate, propionate, and butyrate)
SHIME: Simulator of the Human Intestinal Microbial Ecosystem
SOS: Sphingan Oligosaccharide
SPS: Sphingan Polysaccharide
TEER: TransEpithelial Electrical Resistance
Tetramer: [Glc($\beta$1$\rightarrow$4)GlcA($\beta$1$\rightarrow$4)Glc($\beta$1$\rightarrow$4)Rha], Glc,GlcA,Glc,Rha or Glc2,GlcA,Rha
Octamer: [Glc($\beta$1$\rightarrow$4)GlcA($\beta$1$\rightarrow$4)Glc($\beta$1$\rightarrow$4)Rha]$_2$ Glc,GlcA,Glc,Rha,Glc,GlcA,Glc,Rha or Glc4,GlcA2,Rha2
SEC: Size Exclusion Chromatogram
TGF: Transforming Growth Factor
TLR: toll-like receptor
TNF: Tumor Necrosis Factor
TR1: Treatment Period 1
TR2: Treatment Period 2
TR3: Treatment Period 3
TRT(ave): Average concentration value for treatment periods 1, 2, and 3
UC: ulcerative colitis

BRIEF DESCRIPTION OF THE DRAWINGS

FIG. 8. Reciprocal Simpson Diversity Index in the lumen and mucus of the proximal (PC) or distal colon (DC) of the SHIME on different time points during the control (C1 and C2) and treatment (TR1, TR2 and TR3) period with gellan gum for three different human donors (n=1). The intensity of the shading indicates the absolute diversity index, normalized for each of the three different donors (i.e., within each row).

FIG. 9. Abundance (%) of the dominant phyla in either the lumen or the mucus of the proximal (PC) or distal colon (DC) reactors of the SHIME on different time points during the control (C1 and C2) and treatment (TR1, TR2 and TR3) period with gellan gum for three different human donors (n=1). N.B. One sample was a clear outlier and, therefore, removed from this analysis of control samples, i.e., mucosal sample in the PC of Donor A during the second control week (C2).

FIG. 10. Abundance (%) of different families belonging to specific phyla, in the lumen of the proximal colon (PC) reactors of the SHIME on different time points during the control (C1 and C2) and treatment (TR1, TR2 and TR3) period with gellan gum for three different human donors (n=1). The intensity of the shading indicates the absolute abundance, normalized for each of the different families (i.e., within each row). The intensity of the shading indicates the absolute abundance, normalized for each of the different families (i.e., within each row).

FIG. 11. Abundance (%) of different families belonging to specific phyla, in the lumen of the distal colon (DC) reactors of the SHIME on different time points during the control (C1 and C2) and treatment (TR1, TR2 and TR3) period with gellan gum for three different human donors (n=1). The intensity of the shading indicates the absolute abundance, normalized for each of the different families (i.e., within each row).

FIG. 12. Abundance (%) of different families belonging to specific phyla, in the mucus of the proximal colon (PC) reactors of the SHIME on different time points during the control (C1 and C2) and treatment (TR1, TR2 and TR3) period with gellan gum for three different human donors (n=1). The intensity of the shading indicates the absolute abundance, normalized for each of the different families (i.e., within each row). As a remark, one sample was a clear outlier and therefore removed from this analysis of control samples, i.e., mucosal sample in the PC of Donor A during the second control week (C2).

FIG. 13. Abundance (%) of different families belonging to specific phyla, in the mucus of the distal colon (DC) reactors of the SHIME on different time points during the control (C1 and C2) and treatment (TR1, TR2 and TR3) period with gellan gum for three different human donors (n=1). The intensity of the shading indicates the absolute abundance, normalized for each of the different families (i.e., within each row).

FIG. 19. Basolateral secretion of IL-6 (A) and IL-10 (B) in the control tests LPS−, LPS+, LPS+HC and LPS+NaB. Cytokines were measured after 6 h of LPS treatment of the Caco-2/THP1-Blue™ co-cultures at the basolateral side after pretreatment for 24 h with NaB or complete medium at the apical side. Data are plotted as mean±SEM. (*) represents statistical significant differences compared to LPS+. (*)=$p<0.001$; (**)=$p<0.0001$. LPS−: cells treated with complete medium (no LPS); LPS+: LPS-treated cells; HC: hydrocortisone; NaB: sodium butyrate.

DEFINITIONS

Figure 1A:
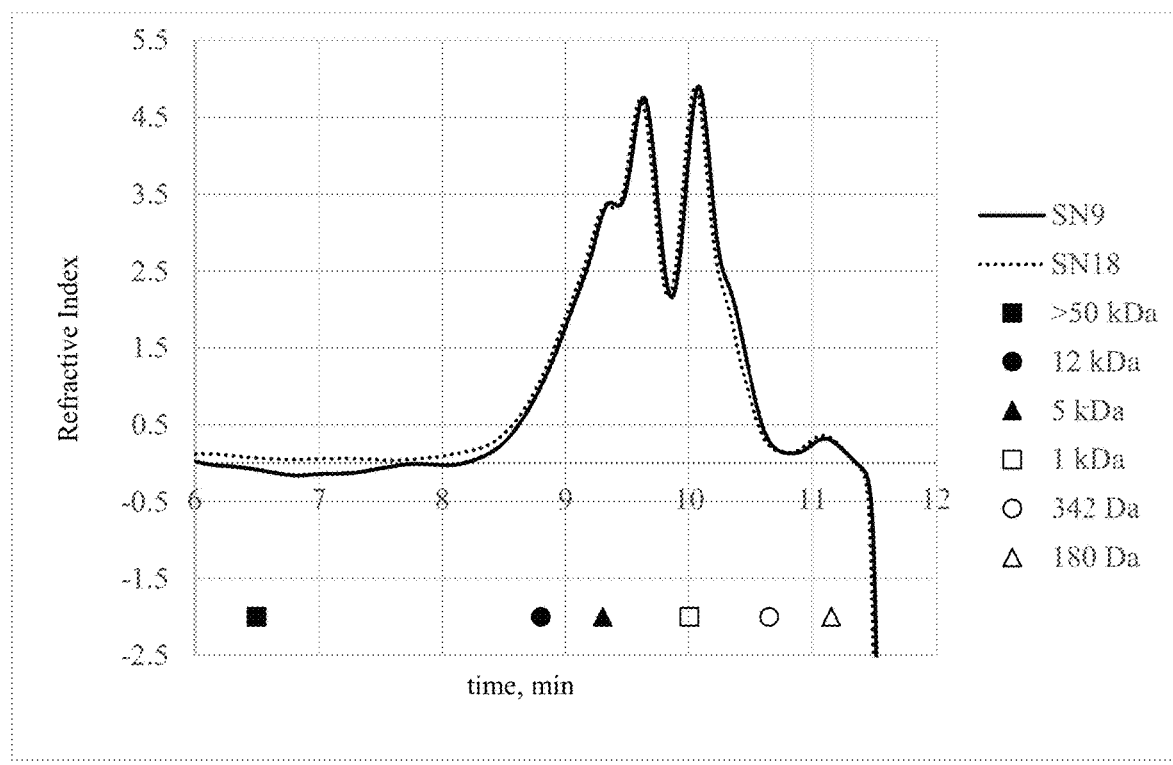
FIG. 1a. Size exclusion chromatogram for acid (SN9, solid line) and enzyme-treated (SN18, dashed line) sphingan poly- and oligosaccharides derived from a high acyl gellan showing Pullulan molecular weight standard elution times (viz., >50 kDa (6.5 min, filled square (■)), 12 kDa (8.8 min, filled circle (●)), 5 kDa (9.3 min, filled triangle (▲)), 1 kDa (10 min, empty square (□)), 342 Da (10.65 min, empty circle (○)), and 180 Da (11.15 min, empty triangle (Δ))).

The term "sphingan," as used herein, refers to a high acyl sphingan, an intermediate acyl sphingan, a low acyl sphingan, a high acyl sphingan polysaccharide, an intermediate acyl sphingan polysaccharide, a low acyl sphingan polysaccharide, a high acyl sphingan oligosaccharide, an intermediate acyl sphingan oligosaccharide, a low acyl sphingan oligosaccharide, or a combination thereof.

The term "high acyl" (or "HA"), as used herein, refers to a sphingan comprising an acyl group (e.g., acetyl and glyceryl). A high acyl sphingan includes, for example, HA gellan, HA welan, HA rhamsan, HA diutan, etc.

The term "intermediate acyl" (or "IA"), as used herein, refers to a sphingan where the acyl content is less than a high acyl sphingan, but greater than the acyl content of a low acyl sphingan. An intermediate acyl sphingan includes, for example, IA gellan, IA welan, IA rhamsan, IA diutan, etc.

The term "low acyl" (or "LA"), as used herein, refers to a sphingan where the acyl group(s) has/have been essentially removed. A low acyl sphingan includes, for example, LA gellan, LA welan, LA rhamsan, LA diutan, etc.

A native sphingan may include, for example, gellan (S-60), welan (S-130), rhamsan (S-194), diutan (S-657), S-88, S-198, and S-7 comprised of a substituted or unsubstituted tetrameric saccharide ("tetramer") depicted generally as [(→3)Glc(β1→4)GlcA(β1→4)Glc(1→4)Rha (α1→)]n, where Glc and GlcA are D-sugars, while Rha is an L-sugar, and where applicable Man is an L-sugar. The chemical structures of selected sphingans are depicted below showing the abbreviated terms for the individual monosaccharides (e.g., (1→3)Glc, (1→4)GlcA, (1→4)Glc, and (1→4)Rha)).

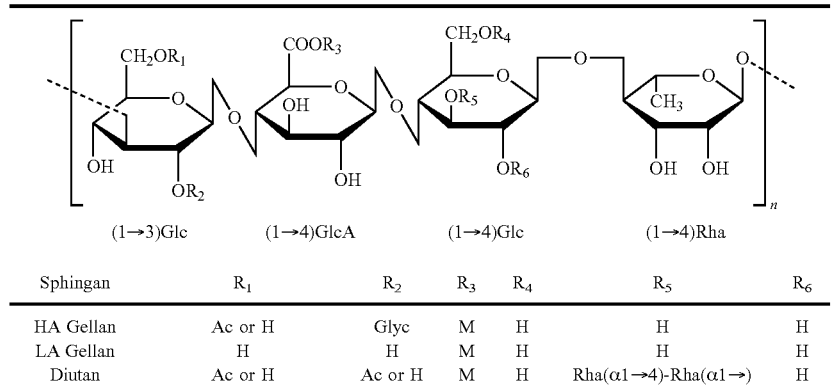

| Sphingan | $R_1$ | $R_2$ | $R_3$ | $R_4$ | $R_5$ | $R_6$ |
|---|---|---|---|---|---|---|
| HA Gellan | Ac or H | | Glyc | M | H | H | H |
| LA Gellan | H | | H | M | H | H | H |
| Diutan | Ac or H | | Ac or H | M | H | Rha(α1→4)-Rha(α1→) | H |

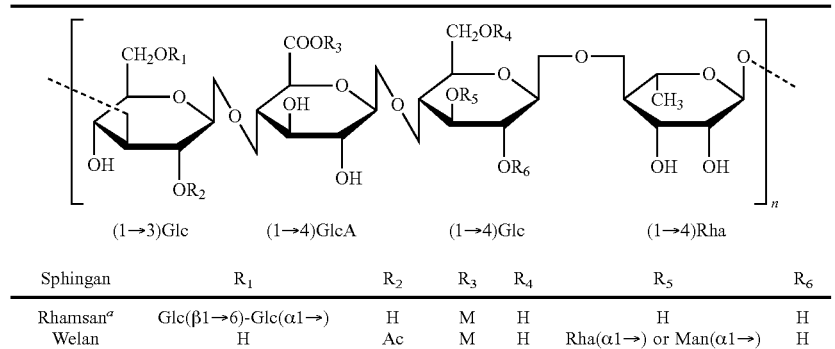

| Sphingan | R₁ | R₂ | R₃ | R₄ | R₅ | R₆ |
|---|---|---|---|---|---|---|
| Rhamsan[a] | Glc(β1→6)-Glc(α1→) | H | M | H | H | H |
| Welan | H | Ac | M | H | Rha(α1→) or Man(α1→) | H |

[a]Rhamsan contains approximately one O-acetyl group per tetramer, distributed over secondary positions.

The term "M," as used herein, refers to a physiologically acceptable cation including, for example, a proton ($H^+$), sodium ($Na^+$), potassium ($K^+$), calcium ($Ca^{2+}$), magnesium ($Mg^{2+}$), or a combination thereof.

The value of "n" refers to a whole or fractional number and refers to the number of tetrameric units that may be substituted or unsubstituted. It is understood that certain native sphingans have a value of n that may be correlated with the molecular weight of the native sphingan (e.g., native gellan gum having MW≈2.5×10⁶ and MN≈2.2×10⁶). (U.S. Pat. No. 6,242,035B1).

The expression "degree of polymerization" or DP, as used herein, refers to the number of monosaccharide units in the polysaccharide or oligosaccharide chain. For instance, with reference to the chemical structure depicted above, where n is four, the DP is sixteen.

The expression "sphingan polysaccharide" (or "SPS"), as used herein, refers to a high/low acyl sphingan having a DP greater than 30 and a DP less than that found in a native sphingan. It is understood that a SPS obtained from a high/intermediate/low acyl sphingan may comprise a plurality of polysaccharides with different DPs.

The expression "sphingan oligosaccharide" (or "SOS"), as used herein, refers to a high/low acyl sphingan having a DP greater than or equal to two and less than or equal to thirty (i.e., 2≤DP≤30). It is understood that a SOS obtained from a high/intermediate/low acyl sphingan (or HA/IA/LA sphingan) may comprise a plurality of oligosaccharides.

DETAILED DESCRIPTION

Embodiments disclosed herein relate generally to an ingestible composition, an ingestible composition and its use, methods of using an ingestible composition, a process for preparing a sphingan oligosaccharide, and a sphingan oligosaccharide prepared by said process for preparing a sphingan oligosaccharide.

A first embodiment is directed to an ingestible composition comprising a prebiotic effective amount of a sphingan.

A prebiotic effective amount of a sphingan may comprise from about 1 g to about 10 g and all values in between, such as, for example, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, or about 9.9.

In an aspect of the first embodiment, the amount of the sphingan is selected from about 1 g to about 10 g, about 1 g to about 9 g, about 1 g to about 8 g, about 1 g to about 7 g, about 1 g to about 6 g, about 1 g to about 5 g, about 1 g to about 4 g, about 1 g to about 3 g, or about 2 g.

Compositions of the first embodiment may comprise a HA/IA/LA sphingan, such as, HA gellan, IA gellan, LA gellan, HA welan, IA welan, LA welan, HA rhamsan, IA rhamsan, LA rhamsan, HA diutan, IA diutan, LA diutan, S-88, S-198, S-7, or a combination thereof.

Compositions of the first embodiment may comprise a HA/IA/LA sphingan polysaccharide.

As explained in greater detail herein, a HA/IA/LA sphingan polysaccharide may be obtained from a HA/LA sphingan using, for example, a process that comprises high-pressure homogenization as described in, for example, the tenth embodiment. Exemplary HA/IA/LA sphingan polysaccharides include, but are not limited to: a high acyl gellan polysaccharide obtained from a high acyl gellan (e.g., KELCOGEL® LT100 gellan and KELGOGEL® HT gellan), an intermediate acyl gellan polysaccharide obtained from an intermediate acyl gellan (e.g., KELCOGEL® DGA), a low acyl gellan polysaccharide obtained from a low acyl gellan (e.g., KELCOGEL® LT gellan, KELCOGEL® gellan, KELCOGEL® F gellan, and GELRITE™ MK gellan), a high/intermediate/low acyl welan polysaccharide obtained from a high/intermediate/low acyl welan, a high/intermediate/low acyl diutan polysaccharide obtained from a high/intermediate/low acyl diutan, and a high/intermediate/low acyl rhamsan polysaccharide obtained from a high/intermediate/low acyl rhamsan.

Compositions of the first embodiment may comprise a HA/IA/LA sphingan oligosaccharide derived either from a native HA/IA/LA sphingan or a HA/IA/LA sphingan polysaccharide. In one aspect, the compositions of the first embodiment may comprise a HA/IA/LA sphingan oligosaccharide derived either from a native HA/IA/LA sphingan or a HA/IA/LA sphingan polysaccharide having a molecular weight, as determined by size exclusion chromatography of about 0.3 kDa to 12 kDa. In another aspect, the compositions of the first embodiment may comprise a HA/IA/LA sphingan oligosaccharide derived either from a native HA/IA/LA sphingan or a HA/IA/LA sphingan polysaccharide having a molecular weight, as determined by size exclusion chromatography of about 1 kDa.

As explained in greater detail herein, a HA/IA/LA sphingan oligosaccharide may be obtained from a native HA/IA/LA sphingan or a HA/IA/LA sphingan polysaccharide, for example, a process that comprises hydrolyzing a glycosidic bond of the native HA/IA/LA sphingan or the HA/IA/LA sphingan polysaccharide and subjecting the hydrolyzed composition to ultrafiltration, size-exclusion chromatography, precipitation, centrifugation, or a combination thereof, as described in, for example, the tenth embodiment. Exemplary HA/IA/LA sphingan oligosaccharides include, but are not limited to:

(i) a composition comprising (or consisting of) Glc,GlcA, Glc,GlcA,Glyc, Glc,GlcA,Rha, Glc,GlcA,Rha,Glyc, Glc,GlcA,Rha,–H2O, Glc,Rha, Glc,Rha+28, Glc2, GlcA, Glc2,GlcA,Rha, Glc2,GlcA,Rha,+28, Glc2, GlcA,Rha,Ac, Glc2,GlcA,Rha,Glyc, Glc2,GlcA,Rha, Glyc,+28, Glc2,GlcA,Rha,Glyc.-H2O, Glc2,GlcA, Rha,–H2O, Glc2,GlcA,Rha2,Glyc, Glc2,GlcA2,Rha, Glc2,GlcA2,Rha2,Ac2,Glyc2,–H2O, Glc2,Rha, Glc3, GlcA,Rha, Glc3,GlcA,Rha2, Glc3,GlcA,Rha2, Glc3, GlcA,Rha2, Glc3,GlcA,Rha2,Glyc, Glc3,GlcA2,Rha, Glc3,GlcA2,Rha,Glyc, Glc3,GlcA2,Rha2,Glyc, Glc3, GlcA3,Rha2, Glc3,GlcA3,Rha2, Glc4,GlcA,Rha2,+43, Glc4,GlcA,Rha2,Ac, Glyc, Glc4,GlcA2,Rha, Glc4, GlcA2,Rha,Ac,Glyc,–H2O, Glc4,GlcA2,Rha,Ac, Glyc2, Glc4,GlcA2,Rha2,Ac,Glyc, Glc4,GlcA2,Rha2, Glyc, Glc4,GlcA3,Rha2, Glc4,GlcA2,Rha3,Ac, Glc4, GlcA3,Rha2/Glc4,GlcA2,Rha2,Glyc2, Glc5,GlcA2, Rha2, Glc5,GlcA2,Rha2, Glc5,GlcA2,Rha2,Ac, Glc5, GlcA4,Rha2, Glc6,GlcA3,Rha3, Glc(Ac/Glyc)x, GlcAx,Glcx,Rhax (where x is 4 to about 25), Glcx, GlcAx,Glcx,Rhax (where x is 4 to about 25), or a combination thereof;

(ii) a composition comprising (or consisting of) a tetramer (Glc,GlcA,Glc,Rha), a tetramer (Glc,GlcA,Glc,Rha) with acetate and/or glycerate, an octamer (Glc,GlcA, Glc,Rha,Glc,GlcA,Glc,Rha), an octamer (Glc,GlcA, Glc,Rha,Glc,GlcA,Glc,Rha) with acetate and/or glycerate, Glc,GlcA,Glc, Rha,Glc,GlcA, Glc,Rha, or a combination thereof;

(iii) a composition comprising (or consisting of) a tetramer (Glc,GlcA,Glc,Rha), an octamer (Glc,GlcA, Glc,Rha,Glc,GlcA,Glc,Rha), a pentamer (Glc,GlcA, Glc,Rha,Glc), GlcA,Glc,Rha, Glc,GlcA,Glc, Glc, GlcA, or a combination thereof;

(iv) a composition comprising (or consisting of) Glc(Glc-Glc),GlcA, Glc(Glc-Glc), GlcA,Glc, Glc,Glc, or a combination thereof;

(v) a composition comprising (or consisting of) a tetramer (Glc,GlcA,Glc,Rha), GlcA,Glc,(Rha-Rha), Glc,(Rha-Rha),Rha, GlcA,Glc,Rha, Glc,GlcA,Glc, Rha,Glc, GlcA,Glc;

(vi) a composition comprising (or consisting of) Glc, GlcA, Glc,GlcA,Glyc, Glc,GlcA,Rha, Glc,GlcA,Rha, Glyc, Glc,Rha, Glc,Rha+28, Glc2,GlcA, Glc2,GlcA, Rha, Glc2,GlcA,Rha,+28, Glc2,GlcA,Rha,Ac, Glc2, GlcA,Rha,Glyc, Glc2,GlcA,Rha,Glyc,+28, Glc3,GlcA, Rha, Glc3,GlcA,Rha2, Glc3,GlcA,Rha2, Glc3,GlcA, Rha2, Glc3,GlcA,Rha2,Glyc, Glc3,GlcA2,Rha,Glyc, Glc3,GlcA2,Rha2,Glyc, Glc3,GlcA3,Rha2, Glc4, GlcA,Rha2,Ac, Glyc, Glc4,GlcA2,Rha2,Ac,Glyc, Glc4,GlcA2,Rha2,Glyc, Glc4,GlcA2,Rha3,Ac, Glc4, GlcA3,Rha2/Glc4,GlcA2,Rha2,Glyc2, Glc5,GlcA2, Rha2, Glc5,GlcA2,Rha2,Ac, Glc(Ac/Glyc)x,GlcAx, Glcx,Rhax (where x is 4 to about 25), or a combination thereof;

(vii) a composition comprising (or consisting of) Glc, GlcA, Glc,GlcA,Rha, Glc,Rha, Glc,Rha+28, Glc2, GlcA,Rha, Glc2,GlcA,Rha,+28, Glc2,GlcA2,Rha, Glc3,GlcA,Rha, Glc3,GlcA,Rha2, Glc3,GlcA2,Rha, Glc3,GlcA3,Rha2, Glc3,GlcA3,Rha2, Glc4,GlcA, Rha2,+43, Glc4,GlcA2,Rha, Glc4,GlcA3,Rha2, Glc5, GlcA2,Rha2, Glc5,GlcA2,Rha2, Glc5,GlcA4,Rha2, Glc6,GlcA3,Rha3, Glcx,GlcAx,Glcx,Rhax (where x is 4 to about 25), or a combination thereof;

(viii) a composition comprising (or consisting of) Glc, GlcA,Rha,–H2O, Glc,Rha, Glc2,GlcA,Rha,–H2O, Glc2,Rha, or a combination thereof;

(ix) a composition comprising (or consisting of) Glc, GlcA, Glc,GlcA,Glyc, Glc,GlcA,Rhaa, Glc,GlcA,Rha, Glyc, Glc,Rha, Glc,Rha+28, Glc2,GlcA, Glc2,GlcA, Rha, Glc2,GlcA,Rha,+28, Glc2,GlcA,Rha,Ac, Glc2, GlcA,Rha,Glyc, Glc2,GlcA,Rha,Glyc,+28, Glc2,GlcA, Rha,Glyc.-H2O, Glc2,GlcA,Rha2,Glyc, Glc2,GlcA2, Rha2,Ac2,Glyc2,–H2O, Glc3,GlcA,Rha, Glc3,GlcA, Rha2, Glc3,GlcA,Rha2,Glyc, Glc3,GlcA2,Rha,Glyc, Glc3,GlcA2,Rha2,Glyc, Glc3,GlcA3,Rha2, Glc4, GlcA,Rha2,+43, Glc4,GlcA,Rha2,Ac, Glyc, Glc4, GlcA2,Rha,Ac,Glyc,–H2O, Glc4,GlcA2,Rha,Ac, Glyc2, Glc4,GlcA2,Rha2,Ac,Glyc, Glc4,GlcA2,Rha2, Glyc, Glc4,GlcA3,Rha2, Glc4,GlcA2,Rha3,Ac, Glc4, GlcA3,Rha2/Glc4,GlcA2,Rha2,Glyc2, Glc5,GlcA2, Rha2, Glc5,GlcA2,Rha2,Ac, Glc(Ac/Glyc)x,GlcAx, Glcx,Rhax (where x is 4 to about 25), or a combination thereof;

(x) a composition comprising (or consisting of) any one of the Sample Nos. 1-18; or (xi) a composition comprising (or consisting of) any one of Sample Nos. 9, 10, 17, and 18.

As stated above, certain sphingans may be substituted by an acyl, a monosaccharide, or a disaccharide side-chain (e.g., the (1→4)Glc of diutan is substituted at $O^3$ by a Rha($\alpha$1→4)-Rha($\alpha$1→) side-chain). A substituted oligosaccharide having a saccharide side-chain is identified by a parenthetical, e.g., GlcA,Glc,(Rha-Rha) and Glc,(Rha-Rha), Rha.

And a reference to a HA/IA/LA sphingan oligosaccharide is understood to mean any one of the exemplary HA/IA/LA sphingan oligosaccharide or a combination thereof.

The compositions may be in the form of liquids, semi-solids or solids. The compositions may be in the form of a cereal, a snack bar, or other ingestible form. The compositions may be fruit-based, such as a juice or a smoothie, or dairy-based such as milk, ice cream, or yoghurts. Compositions can be suitably in the form of beverages. The term "beverage" encompasses a ready to drink liquid form as well as a concentrate and a powder formulation for dissolution. A ready to drink beverage may be still or carbonated.

The compositions may be unsweetened or sweetened with sugar or intense sweeteners such as sucralose, ammonium glycyrrhizinate, acesulfame-K, aspartame, saccharin, a saccharin salt (e.g., sodium, potassium, calcium, etc.), sodium cyclamate, stevia, other non-sugar sweeteners, and a mixture thereof. Compositions may also contain other conventional additives such as flavorings, colorings, stabilizers, etc.

Compositions may be stored as a powdered form in a sealed container or package that may comprise instructions for use.

Alternatively, the compositions may be formulated as a tablet or a capsule product, which may comprise, in addition to a sphingan, other acceptable excipients, such as, a binding agent, a filler, a lubricant, a disintegrant, a glidant, a flow agent, an anti-caking agent, a sorbent, a preservative, a wetting agent, a sweetener, a flavor agent, a coating agent, etc. The tablets may be coated according to methods well known in the art. Examples of excipients include, but are not limited to, an alkaline earth carbonate (e.g., magnesium carbonate, calcium carbonate, etc.); a crosslinked polymer (e.g., crosslinked polyvinylpyrrolidone (crospovidone) and crosslinked sodium carboxymethyl cellulose (croscarmellose sodium)); a fatty acid; a fumed silica; a lubricant (e.g., stearic acid, stearin, magnesium stearate); a pH adjusting agent (e.g., an acid (e.g., hydrochloric acid) and a base (e.g., sodium hydroxide)); a plant fiber (e.g., corn protein zein); a polysaccharide and its derivatives (e.g., a starch, a cellulose, or a modified cellulose, such as microcrystalline cellulose and cellulose ethers such as hydroxypropyl cellulose and hydroxypropyl methylcellulose); a protein (e.g., gelatin); a saccharide and its derivatives (e.g., a disaccharide, e.g., sucrose, lactose, etc.); a shellac; a silicon dioxide; a sodium starch glycolate; a sugar alcohol (e.g., isomalt, xylitol, sorbitol, and maltitol); a synthetic polymer (e.g., polyvinylpyrrolidone and polyethylene glycol); a talc; and a wax.

The compositions may also comprise a probiotic and an additional prebiotic.

Examples of probiotics include, but are not limited to, *Lactobacillus rhamnosus* GG, *Bifidobacterium infantis*, *Lactobacillus acidophilus*, *Bifidobacterium lactis* HN019, *Bifidobacterium longum* (including Strain 35624), *Lactobacillus salivarius*, *Bifodobacterium bifidum*, *Lactobacillus plantarum*, *Lactobacillus paracasei*, *Bifidobacterium breve*, *Lactobacillus gasseri* KS-13, *Bacillus coagulans* (GBI-30, 6086), *Bacillus subtilis* DE 111, each of which may be used alone or a combination thereof.

Examples of an additional prebiotic include, but are not limited to, inulin, a fructooligosaccharide, a galactooligosaccharide, a guar gum, a tara gum, a xanthan gum, a xanthanic polysaccharide, a xanthanic oligosaccharide, a konjac gum, a karaya gum, an arabinogalactan, lactulose, psyllium, a pectin, a pectinic polysaccharide, a pectinic oligosaccharide, tragacanth, acacia, carrageenan, and the like.

Results disclosed herein show that a sphingan (A) promotes beneficial bacterial growth in the colon of a human; (B) decreases propionate and/or increases butyrate levels in the colon of a human; (C) improves intestinal barrier integrity in the colon of a human; and/or (D) reduces levels of TNF-α and/or IL-8 in the colon of a human. Accordingly, embodiments disclosed herein relate to an ingestible composition for:

(A) promoting beneficial bacterial growth in the colon of a mammal, said composition comprising a beneficial bacterial growth effective amount of a sphingan and an ingestible medium (second embodiment);

(B) decreasing propionate and/or increasing butyrate levels in the colon of a mammal, said composition comprising an effective amount of a sphingan and an ingestible medium (third embodiment);

(C) improving intestinal barrier integrity in the colon of a mammal, said composition comprising an intestinal barrier integrity effective amount of a sphingan and an ingestible medium (fourth embodiment); or (D) reducing levels of TNF-α and/or IL-8 in the colon of a mammal, said composition comprising a TNF-α and/or IL-8 reducing effective amount of a sphingan and an ingestible medium (fifth embodiment).

As related to any one of the second, third, fourth, and fifth embodiments the contemplated amount of a sphingan (i.e., (i) a beneficial bacterial growth effective amount of a sphingan (second embodiment), (ii) an effective amount of a sphingan (third embodiment), (iii) an intestinal barrier integrity effective amount of a sphingan (fourth embodiment), and (iv) a TNF-α and/or IL-8 reducing effective amount of a sphingan (fifth embodiment)) may comprise about 1 g to about 10 g of a sphingan, and all values in between, such as, for example, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, and about 9.9 g.

In an aspect of any one of the second, third, fourth, and fifth embodiments the mammal is, for example, a human, a dog, a cat, a rat, a mouse, a hamster, a guinea pig, a cow, a bison, a pig, a sheep, a horse, a goat, a deer, a llama, an alpaca, and the like.

In an aspect of any one of the second, third, fourth, and fifth embodiments, the amount of the sphingan is selected from about 1 g to about 10 g, about 1 g to about 9 g, about 1 g to about 8 g, about 1 g to about 7 g, about 1 g to about 6 g, about 1 g to about 5 g, about 1 g to about 4 g, about 1 g to about 3 g, or about 2 g.

And, in an aspect of any one of the second, third, fourth, and fifth embodiments, the amount of the sphingan is sufficient to achieve an effective sphingan concentration in the colon, where said sphingan colon concentration ranges from about 1 mg/mL to about 10 mg/mL and all values in between, for example, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, or 9.5 mg/mL.

Compositions of any one of the second, third, fourth, and fifth embodiments may comprise any one of a native HA/IA/LA sphingan, a HA/IA/LA sphingan polysaccharide, a HA/IA/LA sphingan oligosaccharide, or combination thereof, and optionally further comprising a probiotic or an additional prebiotic, as described in the first embodiment.

Additionally, embodiments disclosed herein relate either to a method for or a use for the manufacture of a medicament or dietary supplement:

(A) promoting beneficial bacterial growth in the colon of a mammal, said method comprising ingesting on an effective schedule a beneficial bacterial growth effective amount of a sphingan and an ingestible medium (sixth embodiment);

(B) decreasing propionate and/or increasing butyrate levels in the colon of a mammal, said method comprising: ingesting on an effective schedule a composition comprising an effective amount of a sphingan and an ingestible medium (seventh embodiment);

(C) improving intestinal barrier integrity in the colon of a mammal, said method comprising: ingesting on an effective schedule a composition comprising an intestinal barrier integrity effective amount of a sphingan and an ingestible medium (eighth embodiment);

(D) reducing levels of TNF-α and/or IL-8 in the colon of a mammal, said method comprising: ingesting on an effective schedule a composition comprising a TNF-α and/or IL-8 reducing effective amount of a sphingan and an ingestible medium (ninth embodiment);

(E) use of a composition of any one of first, second, third, fourth, and fifth embodiments alone, or in combination with a probiotic or an additional prebiotic, as described herein, for the manufacture of a composition for (i) promoting beneficial bacterial growth in the colon of a mammal (tenth embodiment), (ii) decreasing propionate and/or increasing butyrate levels in the colon of a mammal (eleventh embodiment), (iii) improving intestinal barrier integrity in the colon of a mammal (twelfth embodiment), or (iv) reducing levels of TNF-α and/or IL-8 in the colon of a mammal (thirteenth embodiment); or (F) In an aspect of any one of the sixth, seventh, eighth, ninth, tenth, eleventh, twelfth, and thirteenth embodiments the mammal is, for example, a human, a dog, a cat, a rat, a mouse, a hamster, a guinea pig, a cow, a bison, a pig, a sheep, a horse, a goat, a deer, a llama, an alpaca, and the like.

For these and other embodiments described and claimed herein, an effective schedule for ingestion may include, for example, (i) daily ingestion, such as, once, twice, three-time a day, etc.; (ii) weekly ingestion, such as every day for seven days, every other day for seven days, etc.; (iii) monthly ingestion, such as daily ingestion for a desirable period of time followed by resting period, continued by daily ingestion for a desirable period of time.

As related to any one of the sixth, seventh, eighth, ninth, tenth, eleventh, twelfth, and thirteenth embodiments, the contemplated amount of a sphingan (i.e., (i) a beneficial bacterial growth effective amount of a sphingan (sixth embodiment), (ii) an effective amount of a sphingan (seventh embodiment), (iii) an intestinal barrier integrity effective amount of a sphingan (eighth embodiment), and (iv) a TNF-α and/or IL-8 reducing effective amount of a sphingan (ninth embodiment)) may comprise about 1 g to about 10 g of a sphingan, and all values in between, such as, for example, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, and about 9.9 g.

In an aspect of any one of the sixth, seventh, eighth, ninth, tenth, eleventh, twelfth, and thirteenth embodiments, the amount of the sphingan is selected from about 1 g to about 10 g, about 1 g to about 9 g, about 1 g to about 8 g, about 1 g to about 7 g, about 1 g to about 6 g, about 1 g to about 5 g, about 1 g to about 4 g, about 1 g to about 3 g, or about 2 g.

And, in an aspect of any one of the sixth, seventh, eighth, ninth, tenth, eleventh, twelfth, and thirteenth embodiments, the amount of the sphingan is sufficient to achieve an effective sphingan concentration in the colon, as described herein.

In the alternative, and as related to any one of the sixth, seventh, eighth, and ninth embodiments, the mammal is a human and the contemplated amount of a sphingan (i.e., (i) a beneficial bacterial growth effective amount of a sphingan (sixth embodiment), (ii) an effective amount of a sphingan (seventh embodiment), (iii) an intestinal barrier integrity effective amount of a sphingan (eighth embodiment), and (iv) a TNF-α and/or IL-8 reducing effective amount of a sphingan (ninth embodiment)) may comprise from about 10 mg/kg to about 150 mg/kg of the human body weight of the human ingesting the composition. Additionally, it is contemplated that the amount of sphingan comprises all values in between, such as, for example, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, about 105 mg/kg, about 110 mg/kg, about 115 mg/kg, about 120 mg/kg, about 125 mg/kg, about 130 mg/kg, about 135 mg/kg, about 140 mg/kg, or about 145 mg/kg.

In an aspect of any one of the sixth, seventh, eighth, and ninth embodiments, the mammal is a human and the amount of the sphingan is selected from about 10 mg/kg to about 150 mg/kg, about 10 mg/kg to about 140 mg/kg, about 10 mg/kg to about 130 mg/kg, about 10 mg/kg to about 120 mg/kg, about 10 mg/kg to about 110 mg/kg, about 10 mg/kg to about 100 mg/kg, about 10 mg/kg to about 90 mg/kg, about 10 mg/kg to about 80 mg/kg, about 10 mg/kg to about 70 mg/kg, about 10 mg/kg to about 60 mg/kg, 10 mg/kg to about 50 mg/kg, about 10 mg/kg to about 40 mg/kg, or about 20 mg/kg to about 30 mg/kg of the human ingesting the composition.

Compositions of any one of the sixth, seventh, eighth, and ninth embodiments may comprise any one of a native HA/LA sphingan, a HA/LA sphingan polysaccharide, a HA/LA sphingan oligosaccharide, or combination thereof, and optionally further comprising a probiotic or an additional prebiotic, as described in the first embodiment.

Results disclosed herein show that a sphingan (e.g., a gellan gum) increased Bifidobacteriaceae levels in the proximal and distal portions of a colonic model of a human. At the Operational Taxonomic Unit ("OTU") level, the main changes were found to be attributed to an increase in Bifidobacteriaceae OTU 2 (related to *Bifidobacterium adolescentis*). Therefore, in an aspect of the second, the sixth embodiment, or the tenth embodiment the bacteria is Bifidobacteriaceae. Further, in another aspect of the second, sixth embodiment, or the tenth embodiment, the bacteria is Bifidobacteriaceae OTU 2. The increased Bifidobacteriaceae levels in the lumen of the proximal colon range from about 20%/0 to about 180% during treatment compared to untreated control, while the increased Bifidobacteriaceae levels in the lumen of the distal colon range from about 330% to about 590% during treatment compared to untreated control. In yet another aspect of the second, the sixth embodiment, or the tenth embodiment, the Bifidobacteriaceae levels increase in the lumen of the proximal colon range from about 20% to about 180% during treatment compared to untreated control. And, in a further aspect of the second, the sixth embodiment, or the tenth embodiment the Bifidobacteriaceae levels increase in the lumen of the distal colon range from about 330% to about 590% during treatment compared to untreated control.

Additionally, results disclosed herein shows that a sphingan oligosaccharide at a concentration of about 4 mg/mL increased bacteria (e.g., *Blautia, Parabacteroides, Faecalibacterium, Clostridium* XVIII) levels in vitro based on fecal samples of healthy adults. The *Blautia* levels in vitro increased up to at least about 5-fold compared to untreated control. The *Parabacteroides* levels in vitro increased from about 2-fold to about 40-fold compared to untreated control. The *Faecalibacterium* levels in vitro increased from about 10-fold to about 190-fold compared to untreated control. The *Clostridium* XVIII levels in vitro increased from about 12-fold to about 60-fold compared to untreated control.

Further, results disclosed herein shows that a sphingan oligosaccharide at a concentration of about 4 mg/mL increased bacteria (e.g., *Parabacteroides, Faecalibacterium, Clostridium* XVIII) levels in vitro based on the fecal samples of patients having an inflammatory bowel disease. The *Blautia* levels in vitro increased up to at least about 8-fold compared to untreated control. The *Faecalibacterium* levels in vitro increased up to at least about 8-fold compared to untreated control. The *Clostridium* XVIII levels in vitro increased from about 20-fold to about 100-fold compared to untreated control.

Results disclosed herein show that an ingested sphingan (e.g., gellan gum) decreased propionate levels in both the proximal and distal portions of a colonic model of a human and that ingested gellan gum increased butyrate levels in both the proximal and distal portions of a colonic model. Therefore, in an aspect of the third embodiment, the seventh embodiment, or the eleventh embodiment, where the mammal is a human, decreased propionate levels in the proximal colon range from about 8% to about 21% during treatment compared to control. In an aspect of the third embodiment, the seventh embodiment, or the eleventh embodiment, where the mammal is a human, decreased propionate levels in the distal colon range from about 8% to about 11% during treatment compared to control. In an aspect of the third embodiment, the seventh embodiment, or the eleventh embodiment, where the mammal is a human, increased butyrate levels in the distal colon range from about 15% to about 24%. In an aspect of the third embodiment, the seventh embodiment, or the eleventh embodiment, where the mammal is a human, increased butyrate levels in the distal colon range from about 4% to about 13%.

A fourteenth embodiment is directed to a process for preparing a sphingan polysaccharide ("SPS") and/or a sphingan oligosaccharide ("SOS").

A process for preparing a SPS comprises: hydrating a native HA/IA/LA sphingan in water and reducing the molecular weight of the native HA/IA/LA sphingan by homogenization, sonication, radiation, oxidation, and/or hydrolysis.

Reducing the molecular weight (i.e., reducing the chain length) of a native HA/IA/LA sphingan may be achieved using high-pressure homogenization by a process that comprises: (i) hydrating a HA/LA sphingan product powder in deionized water to obtain a hydrated HA/IA/LA sphingan (about 1% w/v) solution; (ii) passing the hydrated HA/IA/LA sphingan solution through a homogenizer from 1 to 10 times operating at a pressure of from about 8,500 psi to about 12,000 psi (and all values in between) to obtain a homogenized HA/IA/LA SPS solution; (iii) adding a sufficient amount of a suitable organic solvent to the homogenized solution to obtain a HA/IA/LA SPS precipitate; (iv) collecting the HA/IA/LA SPS precipitate by centrifugation; and (v) drying and milling the collected HA/IA/LA SPS powder.

In one aspect of the process for preparing a HA/IA/LA SPS, the HA/IA/LA sphingan may be, for example, high acyl gellan, intermediate acyl gellan, low acyl gellan, high acyl diutan, intermediate acyl diutan, low acyl diutan, a high acyl rhamsan, an intermediate acyl rhamsan, and a low acyl rhamsan. In another aspect of the process for preparing a HA/IA/LA SPS, said passing occurs 1-10 times (e.g., 1, 2, 3, 4, etc.) at a pressure of about 8,500 psi. In yet another aspect of the process for preparing a SPS, said passing occurs 1-10-times (e.g., 1, 2, 3, 4, etc.) at a pressure of about 12,000 psi. In a further aspect of the process for preparing a SPS, said passing occurs 10-times at a pressure of about 12,000 psi. And, in yet another aspect of the process for preparing a SPS, the suitable organic solvent is one that promotes precipitation of the so-formed HA/IA/LA sphingan polysaccharide, including, for example, isopropanol.

A process for preparing a HA/IA/LA SOS comprises: preparing a first composition comprising a native HA/IA/LA sphingan or a HA/IA/LA SPS and a liquid medium; hydrolyzing a glycosidic bond of the HA/IA/LA sphingan or HA/IA/LA SPS to obtain a second composition; subjecting the second composition to ultrafiltration, size-exclusion chromatography, precipitation, centrifugation, or a combination thereof to obtain a third composition comprising the HA/IA/LA SOS; and optionally, isolating or recovering the third composition by a suitable technique, such as, for example, lyophilization.

In an aspect of the process for preparing a HA/IA/LA SOS, said hydrolyzing may be mediated by an acid, an enzyme, sonication, high-pressure homogenization, radiation, or a combination thereof.

In an aspect of the process for preparing a HA/IA/LA SOS, said hydrolyzing may be mediated by an aqueous medium having a pH of about 1 to about 3. In another aspect, said hydrolyzing may be mediated by an aqueous medium having a pH of about 1 to about 3 (or a pH of about 2), wherein said aqueous medium may comprise a suitable inorganic or organic acid. Examples of suitable acids include, but are not limited to, sulfuric acid, hydrochloric acid, nitric acid, phosphoric acid, citric acid, oxalic acid, formic acid, acetic acid, trifluoroacetic acid, or a combination thereof.

In an aspect of the process for preparing a HA/IA/LA SOS, said hydrolyzing is mediated by hydrolyzing with formic acid at a pH of about 2 and a temperature of about 95° C. for a sufficient time to hydrolyze the glycosidic bond of the HA/IA/LA sphingan or HA/IA/LA SPS.

In an aspect of the process for preparing a HA/IA/LA SOS, said hydrolyzing is mediated by an enzyme, wherein the enzyme is capable of cleaving one or more sphingan glycosidic bonds, including, but not limited to, a gellanase, a rhamnogalacturonan endolyase (EC 4.2.2.23), rhamnogalacturonan exolyase (EC 4.2.2.24), gellan lyase (EC 4.2.2.25) described by Hashimoto, a gellan lyase described by Kennedy (1994), or a combination thereof. It is understood that the expression "gellanase" refers to an enzyme that is capable of cleaving one or more glycosidic bonds of a sphingan.

In an aspect of the process for preparing a HA/IA/LA SOS, said subjecting comprises filtering the second composition through a membrane having a molecular weight cutoff of either about 5 kDa or about 10 kDa to obtain a filtrate comprising the third composition.

A fifteenth embodiment is directed to a composition comprising a sphingan oligosaccharide as prepared by the fourteenth embodiment.

Unless defined otherwise, all technical and scientific terms used herein have the same meaning as commonly understood by one of ordinary skill in the art. The following examples are intended only to further illustrate the embodiments claimed and disclosed herein, and are not intended to limit the scope of the claimed subject matter.

Examples

I. Example I. Preparation of HA/LA SPSs and SOSs

Preparation of a Sphingan Polysaccharide.

The chain length of a native sphingan may be reduced using high-pressure homogenization by a process that comprises: (i) hydrating a sphingan (e.g., gellan, diutan, and rhamsan) product powder at 1% w/v in 1-L of deionized water to obtain a hydrated sphingan solution; (ii) mechanically digesting the hydrated sphingan solution in an APV Model 1000 homogenizer at about 12,000 psi (×10) to obtain homogenized solutions; (iii) adding a sufficient amount of isopropyl alcohol to the homogenized solution to obtain a sphingan polysaccharide precipitate; (iv) collecting the sphingan polysaccharide precipitate by centrifugation; and (v) drying and milling the collected sphingan polysaccharide powder. Using this procedure on selected sphingans (e.g., high acyl gellan, low acyl gellan, high acyl diutan, and high acyl rhamsan), the following samples of sphingan polysaccharides were prepared, as shown in Table 1, which were hydrated in water at a concentration of 0.8% w/v for subsequent studies.

TABLE 1

Summary of sphingan polysaccharides (Sample Nos. 1-7).

| Sample No. | Comments |
| --- | --- |
| 1 | Gellan polysaccharide obtained from KELCOGEL ® LT100 gellan (high acyl gellan, unclarified). |
| 2 | Gellan (high acyl) polysaccharide obtained from KELCOGEL ® HT gellan (high acyl enzyme treated PHB-free). |
| 3 | Gellan polysaccharide obtained from GELRITE ™ MK gellan (low acyl clarified, double-precipitated). |
| 4 | Diutan polysaccharide obtained from PHB-free-diutan. |
| 5 | Rhamsan polysaccharide obtained from native rhamsan. |
| 6 | Gellan (from strain 438) polysaccharide.$^a$ |
| 7 | Gellan (from strain 438) polysaccharide.$^b$ |

Notes:
$^a$Sample No. 6 is a gellan polysaccharide obtained from gellan, which was produced from strain 438, a strain derived from wild-type, *Sphingomonas elodea*. The gellan from strain 438 was isolated by treating the fermentation broth with protease, EDTA, SDS, lysozyme and glucoamylase; followed by gellan gum recovery by isopropanol induced precipitation of the treated and heated broth.
$^b$Sample No. 7 is a gellan polysaccharide obtained from gellan, which was produced from strain 438. The gellan from strain 438 was isolated by centrifuging the fermentation broth to obtain pelleted cells and a supernatant, treating the collected supernatant with glucoamylase and protease, and recovering gellan from heated broth using isopropanol precipitation.

A gellan polysaccharide manufactured herein is unlike commercialized gellan products in that the chain-length is reduced by high-pressure homogenization. Indeed, previous studies showed that high-pressure homogenization reduces the chain-length (and, thus, the molecular weight) of native gellan. (See U.S. Pat. No. 6,242,035B1, incorporated by reference in its entirety, where high-pressure homogenization of native gellan gum (MW≈2.5×10$^6$; MN≈2.2×10$^6$) results in a gellan gum having a MW of less than or equal to about 1.7×10$^6$, as measured by Size Exclusion Chromatography/Multiple Angle Laser Light Scattering.)

Preparation of Sphingan Oligosaccharides (SOSs)

SOS preparation generally comprises: (i) preparing a 2% w/v native HA/IA/LA sphingan (or a HA/IA/LA SPS) solution; (ii) hydrolyzing with formic acid (pH 2) at 95° C., overnight to obtain a hydrolysate; (iii) filtering the hydrolysate using an ultrafiltration membrane having a molecular weight cut-off of either 5 kDa or 10 kDa to obtain a filtrate; (iv) lyophilizing the filtrate to obtain a lyophilizate; (v) washing the lyophilizate with anhydrous ethanol (×3) to obtain a washed powder; and (vi) drying the washed powder to obtain a SOS. (Alternatively, hydrolysis may occur using: (i) a suitable enzyme, such as a gellanase; (ii) sonication; (iii) high-pressure homogenization; (iv) radiation; or (v) other known processes.) Using the acid hydrolysis (e.g., formic acid) procedure or enzyme hydrolysis (e.g., Japan gellanase (EC 4.2.2.25) or strain 438 gellanase), the following samples of HA/LA sphingan oligosaccharides were prepared, as shown in Table 2a, where the percent monosaccharide content relates to the monosaccharide (glucose and rhamnose) content divided by the concentration of the sample, the monosaccharide composition, oligosaccharide content, and molecular weight is as described below.

TABLE 2a

Summary of Sphingan Oligosaccharide (Sample Nos. 8-18.)

| Sample No. | Comments |
| --- | --- |
| 8 | SOSs obtained from KELCOGEL ® LT100 gellan; acid hydrolysis; 5k Da cutoff (1.7% monosaccharide content). |
| 9 | SOSs obtained from KELCOGEL ® HT gellan; acid hydrolysis, 5k Da cutoff (1.5% monosaccharide content). Monosaccharide composition: Rha, Glc, GlcA, Glyc in an approximate ratio of 3:5:2:2 with an unknown uronic acid present Oligosaccharide content: gellan-like oligosaccharides (both acetylated and glycerated) having a DP of about 2 to about 9. Molecular weight: Sample molecular weight about 0.5 kDa to about 4 kDa (dual peak smaller and larger than about 1.2 kDa observed). |
| 10 | SOSs obtained from GELRITE ™ MK gellan; acid hydrolysis; 5k Da cutoff (1.8% monosaccharide content). Monosaccharide composition: Rha, Glc, GlcA in an approximate ratio of 3:5:2. Only trace amounts of glycerate Oligosaccharide content: gellan-like oligosaccharides (mainly unesterified) having a DP of about 2 to about 12. Molecular weight: Sample molecular weight about 0.5 kDa to about 4 kDa (dual peak smaller and larger than 1.2 kDa observed). |
| 11 | SOSs obtained from native PHB-free diutan; acid hydrolysis; 5k Da cutoff (0.7% monosaccharide content). |
| 12 | SOSs obtained from native rhamsan; acid hydrolysis; 5k Da cutoff (2.2% monosaccharide content). |
| 13 | SOSs obtained from KELGOGEL ® HT gellan; acid hydrolysis; 10k Da cutoff. |
| 14 | SOSs obtained from GELRITE ™ MK gellan; acid hydrolysis; 10k Da cutoff. |
| 15 | SOSs obtained from native PHB-free diutan; acid hydrolysis; 10k Da cutoff. |
| 16 | SOSs obtained from native rhamsan; acid hydrolysis; 10k Da cutoff. |
| 17 | SOSs obtained from GELRITE ™ MK gellan; enzyme (Japan gellanase, EC 4.2.2.25) hydrolysis; 5k Da cutoff. Monosaccharide composition: ratio of Rha and Glc of about 1 to about 2 (trace amounts of glucuronic acid and large amounts of unknown compound 1 and 2). Oligosaccharide content: about 50% unsaturated GlcA,Glc,Rha,Glc and about 10% unsaturated GlcA,Glc,Rha. Molecular weight: narrow size distribution about 1 kDa |

TABLE 2a-continued

Summary of Sphingan Oligosaccharide (Sample Nos. 8-18.)

| Sample No. | Comments |
|---|---|
| 18 | SOSs obtained from KELCOGEL ® HT gellan; enzyme (from strain 438) hydrolysis, 5k Da cutoff. Monosaccharide composition: Rha, Glc, GlcA, Glyc in an approximate ratio of 3:5:2:2 with an unknown uronic acid present. Oligosaccharide content: gellan-like oligosaccharides (both acetylated and glycerated) having a DP of about 2 to about 9 with minor amounts of unsaturated compounds. Molecular weight: Sample molecular weight of about 0.5 kDa to about 4 kDa observed (dual peak smaller and larger than about 1.2 kDa observed, same as SN9). |

The monosaccharide content determined for selected SOS samples by dissolving SOS sample in deionized water and analyzing for the content of glucose and rhamnose using Thermo Fisher's Ion Chromatography system. The total monosaccharide content is calculated as the total concentration of the glucose and rhamnose divided by the concentration of the sample.

The monosaccharide composition (for Sample Nos. 9-10 and 17-18) was determined as follows. SOS samples were dissolved in 4% sulfuric acid to a concentration of 3.5 g/L and autoclaved at 121° C. for one hour. Monosaccharides were quantified using a Dionex ICS-5000 system according to Zeuner (2016). Glycerate was quantified using external standards. Unknown compound 1 ("UNK1"), unknown compound 2 ("UNK2"), and unknown uronic acid 1 ("UNK URON1") were quantified as glucuronic acid units. Table 2b summarizes the monosaccharide composition for each of Sample Nos. 9-10 and 17-18.

TABLE 2b

Summary of Sphingan Oligosaccharide (Monosaccharide Composition, Sample Nos. 9-10 and 17-18.)

| Sample Nos. | UNK1 | UNK2 | Rha | Glc | Glyc | GlcA | UNK URON1 |
|---|---|---|---|---|---|---|---|
| | | | mol % (std. dev.) | | | | |
| 9 | 0.44 | 1.58 | 29.22 | 50.22 | 21.56 | 20.57 | 8.02 |
| | (0.07) | (0.47) | (1.61) | (1.05) | (1.32) | (0.33) | (0.44) |
| 10 | 0.42 | 1.60 | 27.45 | 53.16 | 0.00 | 19.40 | 7.87 |
| | (0.09) | (0.51) | (1.60) | (0.43) | (0.00) | (0.16) | (0.16) |
| 17 | 21.26 | 70.71 | 34.09 | 65.91 | 0.00 | 0.00 | 0.00 |
| | (0.90) | (2.15) | (0.52) | (1.83) | (0.00) | (0.00) | (0.00) |
| 18 | 0.48 | 1.18 | 29.14 | 50.86 | 23.17 | 20.00 | 7.85 |
| | (0.04) | (0.13) | (1.36) | (4.44) | (1.33) | (2.04) | (0.45) |

The oligosaccharide content (for Sample Nos. 9-10 and 17-19) was determined as follows. Identification and relative quantification of oligosaccharides was performed by liquid chromatography electrospray ionization mass spectrometry (LC-ESI-MS) on an Amazon SL iontrap (Bruker Daltonics, Bremen Germany) coupled to an UltiMate 3000 UHPLC (Dionex, Sunnyvale, Calif. USA). 5 μL sample in 50% ACN (5 g/L final) was injected on a TSKgel Amide 80 HILIC column (150 mm×2 mm; 2 μm, TOSOH, Greisheim, Germany). The chromatography was performed at 0.2 mL/min at 45° C. on a three-eluent system comprised of eluent A (water), eluent B (acetonitrile), and C (100 mM ammonium formate pH 5). Eluent C was kept at 5% at all time. The elution profile was as follows (time indicated in min): 0-5, isocratic 75% B; 5-25, linear gradient to 25% B; 25-30, isocratic 5% B; 30-40, isocratic 75% B. The electrospray was operated in negative mode with UltraScan mode and a scan range from 100-2000 m/z, smart parameter setting of 1000 m/z. Automatic $MS^2$ events was executed for the two highest prevalent precursor ions. Capillary voltage at 4.5 kV, end plate off-set 0.5 kV, nebulizer pressure at 3.0 bar, dry gas flow at 12.0 L/min, and dry gas temperature at 280° C. Compounds were identified by MS and $MS^n$, and quantified by relative intensity in Data analysis 4.2 SR2.

TABLE 2c

Summary of Sphingan Oligosaccharide (Oligosaccharide Content, Sample Nos. 9-10 and 17-18).

| SOSs | Sample Nos./SOS Content, % | | | |
|---|---|---|---|---|
| | 9 | 10 | 17 | 18 |
| Glc,GlcA | 3.24 | 2.37 | — | 2.71 |
| Glc,GlcA,Glyc | 3.28 | — | — | 3.06 |
| Glc,GlcA,Rha$^a$ | 0.80 + 14.25 | 0.79 + 16.85 | — | 1.22 + 12.79 |
| Glc,GlcA,Rha,Glyc | 1.02 | — | — | 0.65 |
| Glc,GlcA,Rha,–H20 | — | — | 11.92 | — |
| Glc,Rha | 4.33 | 1.74 | 1.30 | 3.39 |
| Glc,Rha+28 | 0.89 | 0.39 | — | 0.96 |
| Glc2,GlcA | 0.88 | — | — | 0.84 |
| Glc2,GlcA,Rha | 11.95 | 15.84 | — | 10.07 |
| Glc2,GlcA,Rha,+28 | 7.52 | 8.83 | — | 8.11 |
| Glc2,GlcA,Rha,Ac | 1.36 | — | — | 1.04 |
| Glc2,GlcA,Rha,Glyc | 10.86 | — | — | 10.20 |
| Glc2,GlcA,Rha,Glyc,+28 | 4.22 | — | — | 5.25 |
| Glc2,GlcA,Rha,Glyc.—H2O | — | — | — | 0.50 |
| Glc2,GlcA,Rha,Rha,—H2O | — | — | 54.88 | — |
| Glc2,GlcA,Rha2,Glyc | — | — | — | 1.47 |
| Glc2,GlcA2,Rha | — | 0.33 | — | — |
| Glc2,GlcA2,Rha2,Ac2,Glyc2,—H2O | — | — | — | 3.29 |
| Glc2,Rha | — | — | 23.00 | — |
| Glc3,GlcA,Rha | 0.97 | 2.10 | — | 0.78 |
| Glc3,GlcA,Rha2 | 0.56 | — | — | — |
| Glc3,GlcA,Rha2 | 1.53 | 2.79 | — | 0.56 |
| Glc3,GlcA,Rha2 | 2.79 | — | — | — |
| Glc3,GlcA,Rha2,Glyc | 2.79 | — | — | 2.42 |

TABLE 2c-continued

Summary of Sphingan Oligosaccharide (Oligosaccharide Content, Sample Nos. 9-10 and 17-18).

| | Sample Nos./SOS Content, % | | | |
|---|---|---|---|---|
| SOSs | 9 | 10 | 17 | 18 |
| Glc3,GlcA2,Rha | — | 1.81 | — | — |
| Glc3,GlcA2,Rha,Glyc | 1.81 | — | — | 1.81 |
| Glc3,GlcA2,Rha2,Glyc | 5.47 | — | — | 4.82 |
| Glc3,GlcA3,Rha2 | — | 2.90 | — | — |
| Glc3,GlcA3,Rha2 | 3.36 | 11.59 | — | 3.19 |
| Glc4,GlcA,Rha2,+43 | — | 5.40 | — | 1.57 |
| Glc4,GlcA,Rha2,Ac, Glyc | 2.70 | — | — | 2.72 |
| Glc4,GlcA2,Rha | — | 2.59 | — | — |
| Glc4,GlcA2,Rha,Ac,Glyc,—H2O | — | — | — | 0.87 |
| Glc4,GlcA2,Rha,Ac,Glyc2 | — | — | — | 0.89 |
| Glc4,GlcA2,Rha2,Ac,Glyc | 2.04 | — | — | 1.68 |
| Glc4,GlcA2,Rha2,Glyc | 5.49 | — | — | 3.97 |
| Glc4,GlcA3,Rha2 | — | 13.12 | — | 2.58 |
| Glc4,GlcA,Rha3,Ac | 0.95 | — | — | 0.88 |
| Glc4,GlcA3,Rha2/Glc4,GlcA2,Rha2,Glyc2 | 2.79 | — | — | 2.20 |
| Glc5,GlcA2,Rha2 | 0.69 | 0.69 | — | 0.44 |
| Glc5,GlcA2,Rha2 | — | 0.69 | — | — |
| Glc5,GlcA2,Rha2,Ac | 1.57 | — | — | 1.57 |
| Glc5,GlcA4,Rha2 | — | 0.24 | — | — |
| Glc6,GlcA3,Rha3 | — | 0.07 | — | — |
| unknown 1513 derivative | 3.24 | — | — | — |
| unknown 379z1 | — | — | 2.86 | — |
| unknown 597z2 | — | 1.24 | — | — |
| unknown 668z2 | — | 7.40 | — | — |
| unknown 719z1 + Glyc | — | — | — | 0.63 |
| unknown 719z1 | — | — | — | 0.89 |
| unknown Glc2,GlcA,Rha,—H2O derivative | — | — | 6.04 | — |
| unknown Glc3,GlcA2,Rha2 derivative | — | 0.93 | — | — |

$^a$Glc,Glc,Rha could be Rha-Glc-GlcA or GlcA-Glc-Rha.

The SOS identified as Glc2,GlcA,Rha,Glyc represents a gellan tetramer unit with a single glycerate, while the SOS identified as Glc2,GlcA,Rha,Ac represents a gellan tetramer unit with a single acetyl. Certain SOSs include multiple sugar moieties (viz., Glc5,GlcA2,Rha2,Ac)—the oligosaccharide may be deduced from the specified saccharide numbers. For instance, Glc5,GlcA2,Rha2,Ac includes two tetrameric units (viz., Glc-GlcA-Glc-Rha) with an additional glucopyranosyl (Glc) and an acetyl (Ac). Further, Glc6, GlcA3,Rha3 represents an oligosaccharide that includes three tetrameric units (viz., Glc-GlcA-Glc-Rha times three). The SOSs identified by loss of water ("–H2O", see e.g., Glc2,GlcA,Rha,Glyc.–H2O) represents the unsaturated product of a lyase/β-elimination. In some cases for the longer gellan-like oligomers (e.g., Glc4,GlcA3,Rha2/Glc4, GlcA2,Rha2,Glyc2), two structures are proposed because mass spectral fragmentation is insufficient to distinguish between the presence of one glucuronic acid or two glycerate substitutions. Not all of the observed SOSs could be structural identified. Based on the fragmentation, some compounds could be partially identified because of the similarity in fragmentation pattern, hence denoted "unknown m/z derivative" after the most similar identified compound. Other compounds were impossible to identify due to poor fragmentation or due to being a different type of compound than the expected gellan derived SOSs. These unknown SOSs are denoted "unknown (observed m/z) z1 or z2" depending on whether one or two charges was observed. As evidenced by the Size Exclusion Chromatography data, infra, the analyzed samples may comprise sphingan polysaccharides (DP>30, but less than a native sphingan) and sphingan oligosaccharides (2≥DP≤30).

The reported molecular weight of the SOS samples was determined as follows. High Performance Size Exclusion Chromatography was performed using an Ultimate iso-3100 SD pump with a WPS-3000 sampler (Dionex) connected to an RI-101 refractive index detector (Shodex). 100 µL of sample was loaded on a TSKgel G3000PW column (300× 7.5 mm) equipped with a TSKgel PWH guard column (7.5×7.5 mm) (Tosoh Bioscience). Elution was performed with 100 mM sodium nitrate at a flow rate of 1.0 mL/min at 40° C. Pullulan standards were used as references.

FIG. 1$a$ depicts a size exclusion chromatogram ("SEC") for acid (SN9, solid line) and enzyme-treated (SN18, dashed line) sphingan poly- and oligosaccharides derived from a high acyl gellan, while FIG. 1$b$ depicts a SEC for acid (SN10, solid line) and enzyme-treated (SN17, dashed line) sphingan poly- and oligosaccharides derived from a low acyl gellan. Both FIG. 1$a$ and FIG. 1$b$ show pullulan molecular weight standard elution times (viz., >50 kDa (6.5 min, filled square (■)), 12 kDa (8.8 min, filled circle (●)), 5 kDa (9.3 min, filled triangle (▲)), 1 kDa (10 min, empty square (□)), 342 Da (10.65 min, empty circle (○)), and 180 Da (11.15 min, empty triangle (△))). The SEC data for FIG. 1$a$ show a comparable distribution of sphingan polysaccharides (SPSs) and sphingan oligosaccharides (SOSs) derived from a high acyl sphingan. This should be compared to the SEC data for FIG. 1$b$ where the distributions of SPSs and SOSs for the acid-treated sample (SN10) differs from the distributions of SPSs and SOSs for the enzyme-treated sample (SN17). The SEC data also show molecular weight range of about 0.5 kDa to about 4 kDa (and possibly up to about 12 kDa) for Sample Nos. 9, 10, and 18. Interestingly, the sample (SN17) derived from a low acyl sphingan with enzyme treatment shows a primary elution of SOSs having a molecular weight range of about 0.5 kDa to about 1 kDa (with a narrow size distribution of the peak at about 1 kDa).

The oligomer content of SOSs was determined by mass spectral analysis. Generally, a SOS sample was prepared by dissolving a SOS at a concentration of 0.4% using water/acetonitrile (1:1) containing 1 mM NaCl. Samples were filtered through a 0.22 micron filter before introduction into Thermo Fisher's MSQ plus Single Quad Mass Spec. The mass spectrometer was operated in negative electrospray ionization mode, scanning from 150-1000 m/z. From the intact mass of the oligomers, different oligosaccharides were found in the SOS samples. Table 3 summarizes the oligomers observed for selected SOS samples.

TABLE 3

Identified oligomers in SOSs.

| Sample No. | Identified Oligomers |
|---|---|
| 9 | Tetramer (663), tetramer with glycerate (751), octamer (654 two charges), Glc,GlcA,Glc (517), Rha,Glc,GlcA (501), Glc,Rha (361, chloride adduct) |
| 10 | tetramer (663), octamer (654, two charges), pentamer (Glc,GlcA,Glc,Rha,Glc, 825), GlcA,Glc,Rha (501), Glc,GlcA,Glc (517), Glc,GlcA (355) |
| 11 | Glc(Glc-Glc), GlcA (679), Glc(Glc-Glc) (539, chloride adduct), GlcA, Glc (391, chloride adduct), Glc,Glc (377, chloride adduct) |
| 12 | Tetramer (663), GlcA,Glc,(Rha-Rha) (683, chloride adduct), Glc-(Rha-Rha),Rha (654, chloride adduct), GlcA,Glc,Rha (501), Glc,GlcA,Glc (517), Rha,Glc (361, chloride adduct), GlcA,Glc (355) |

( ) denotes side chain.

II. Example II. Effect of Sphingans (e.g., Native Sphingans, SPSs, and SOSs) on the Activity of Selected Gut Microbiota Samples containing 8 mg/mL (0.8% w/v) of SPS or SOS were diluted by a factor of two to provide samples containing 4 mg/mL (0.4% w/v) of SPS or SOS. The effect of Sample Nos. 1-12 at a concentration of 4 mg/mL on a panel of over twenty-five gut microbiota was assessed after 24 h of fermentation using an in vitro fermentation screening platform ("i-screen"), as described by Fehlbaum (2018). Specifically, a standard fecal microbiota pool derived from 5-6 healthy adults (health based on exclusion criteria) was used that was pre-cultured overnight from a frozen stock. This was followed by dilution in microtiter plates in which the samples were added and subsequently anaerobically incubated for 24 h at 37° C. After incubation, culture samples were harvested and processed for further analysis. In a 96 well plate some wells were used for technical controls, control without microbiota (n=3), and a negative control with microbiota only (n=3), leaving 80 wells available for experiments. A number of sphingan samples and comparative samples—plant extracts (e.g., pectins, pectin oligosaccharides, and carrageenans) and biogums (e.g., xanthan and xanthan oligosaccharides)) were analyzed at a concentration of about 4 mg/mL, which corresponds to a dose of about 4 g/day. (Van den Abbeele (2011).)

Shifts in microbiota composition were determined by next generation sequencing, which recognizes bacteria at the genus level and in many cases (but not all) at the species level. To have a uniform distribution of samples in the sequencing pool total bacterial load was established by a quantitative Polymerase Chain Reaction ("PCR") using a universal primer-probe set. 16s rDNA amplicons of the V4 region were prepared by PCR, thereby standardizing the level of template DNA and using unique error correcting barcoded primers and avoiding over-amplification. Next, amplicons were gel-purified, quantified and pooled. Sequence analysis was then performed on the lllumina MiSeq® instrument by paired end sequencing (2×250 bp). Downstream sequence analysis was performed using a standardized sequencing pipeline developed by the Netherlands Organization for Applied Scientific Research. The pipeline foresees in assembly of the paired end reads, quality filtering, chimera removal and taxonomic classification+ clustering of processed reads.

The standard controls were carried out in triplicate. In particular, the microbe panel included *Bacteroides, Coprococcus, Lachnospiraceae* unclassified, *Megasphaera, Escherichia/Shigella, Clostridium* X1Va, *Allisonella, Bifidobacterium, Dorea, Collinsella, Mogibacterium, Sutterella, Bilophila, Blautia, Clostridium sensu stricto, Phascolarctobacterium, Faecalibacterium, Clostridium* X1Vb, *Clostridium* XI, *Acidaminococcus, Gemmiger, Lachnospira, Parabacteroides, Paraprevotella,* and *Butyricicoccus.* The effect was determined relative to an untreated control. Table 4a summarizes the observed effect for a first i-screen analysis of Sample Nos. 1-12 on *Bifidobacterium* and *Faecalibacterium* growth, where the reported results are relative to an untreated control (growth denoted as 1.0).

TABLE 4a

Selected gut microbiota activity data observed for Sample Nos. 1-12.

| | Bacterial Growth | | | |
|---|---|---|---|---|
| Sample No. | *Bifido-bacterium* | *Blautia* | *Faecali-bacterium* | *Para-bacteroides* |
| 1 | 1.42 | 1.09 | 0.90 | 1.80 |
| 2 | 1.11 | 0.87 | 0.71 | 1.63 |
| 3 | 1.23 | 0.85 | 0.83 | 4.03 |
| 4 | 1.16 | 0.84 | 0.51 | 0.93 |
| 5 | 1.32 | 1.60 | 0.43 | 2.51 |
| 6 | 0.85 | 0.81 | 1.58 | 2.37 |
| 7 | 0.88 | 0.92 | 0.78 | 4.62 |
| 8 | 0.96 | 3.23 | 112.77 | 9.47 |
| 9 | 1.00 | 2.42 | 58.31 | 5.37 |
| 10 | 0.78 | 4.78 | 188.91 | 21.11 |
| 11 | 0.91 | 2.58 | 41.57 | 32.57 |
| 12 | 0.96 | 3.49 | 70.44 | 38.69 |

The bolded values represent significant changes in bacterial growth compared to untreated control. Consistent with results reported in Example III (infra), sphingan polysaccharides (viz. Sample Nos. 1-3) promoted the growth of *Bifidobacterium*. Surprisingly, sphingan oligosacccharides (viz., Sample Nos. 8-12) promoted the growth of each of *Faecalibacterium, Blautia,* and *Parabacterioides* by a substantial degree relative to untreated control. It is well known that *Bifidobacterium* and *Faecalibacterium* (e.g., *Faecalibacterium prausnitzii*) are butyrate producing bacteria. Accordingly, the i-screen results showing that sphingan oligosacccharides promote growth of *Faecalibacterium* suggests that these compositions exhibit prebiotic activity. And, since *Faecalibacterium prausnitzii* is known to be associated with anti-inflammation, the i-screen results suggest that SOSs function as anti-inflammatory agents by promoting the growth of *Faecalibacterium prausnitzii*.

Additional i-screen analyses were performed on Sample Nos. 9, 10, 17, and 18 using three different fecal pools, viz., two pools derived from healthy adults (H1 and H2) and one pool obtained from patients having irritable bowel disease ("IBD") for three or four bacteria (viz., *Blautia, Parabacte-* roides, *Faecalibacterium, Clostridium* XVIII). Specifically, fecal pools used include: (i) the H1 pool was derived from six healthy adult volunteers (Caucasian, 25-60 years old, European lifestyle and nutrition, self-assessment of health status, no antibiotic use in the last 3 months), (ii) the H2 pool was derived from (5) healthy adult volunteers (20-65 years old, no antibiotic use in the last 3 months, self-assessment of health status), and (iii) the IBD pool was derived from four patients with IBD, viz., ulcerative colitis. Table 4b summarizes the observed effect for the additional i-screen analyses (viz., first i-screen (Nos. 1-2), second i-screen (Nos. 3-4), and third i-screen (Nos. 5-16)) of Sample Nos. 9-10 and 17-18 on three or four bacteria (viz., *Blautia* ("Blaut."), *Parabacteroides* ("Para."), *Faecalibacterium* ("Faecal."), *Clostridium* XVIII ("ClXVIII")) growth, where the reported results are relative to an untreated control (growth denoted as 1.0).

TABLE 4b

Selected gut microbiota activity data observed for Sample Nos. 9-10 and 17-18.

| No. | Sample No. | Pool | Blaut. | Para. | Faecal. | ClXVIII |
|---|---|---|---|---|---|---|
| 1 | 9[a] | H1 | 2.42 | 5.37 | 58.31 | — |
| 2 | 10[a] | H1 | 4.78 | 21.11 | 188.91 | — |
| 3 | 9[b] | H1 | 2.21 | 6.79 | 30.71 | — |
| 4 | 10[b] | H1 | 3.20 | 15.99 | 51.54 | — |
| 5 | 9 | H1 | 1.91 | 3.56 | 3.75 | — |
| 6 | 10 | H1 | 2.67 | 8.37 | 23.19 | — |
| 7 | 17 | H1 | 2.54 | 4.34 | 7.86 | — |
| 8 | 18 | H1 | 1.90 | 3.82 | 5.16 | — |
| 9 | 9 | H2 | 1.10 | 3.64 | 6.76 | 16.63 |
| 10 | 10 | H2 | 1.79 | 7.25 | 21.93 | 31.13 |
| 11 | 17 | H2 | 2.18 | 6.84 | 1.39 | 55.91 |
| 12 | 18 | H2 | 1.27 | 3.38 | 7.47 | 12.66 |
| 13 | 9 | IBD | — | 1.74 | 5.11 | 31.39 |
| 14 | 10 | IBD | — | 6.92 | 6.06 | 30.84 |
| 15 | 17 | IBD | — | 6.79 | 2.45 | 98.28 |
| 16 | 18 | IBD | — | 1.63 | 5.26 | 32.58 |

[a]Faecal. responses are as reported in Table 4a.
[b]Faecal. responses are as reported in Table 5.

With respect to Table 4b entries 1-4, it may be seen that SOSs promoted the increase in the fold-change of *Blautia, Parabacteroides* and *Faecalibacterium* in fecal pools of healthy adults compared to untreated controls. SOSs derived from low acyl gellan oligomers exhibited the highest fold change of *Faecalibacterium* (188.91), as well as *Parabacteroides* (21.11) and *Blautia* (4.78).

With respect to Table 4b entries 5-8, the following observations were made. SOSs (acid and enzyme treated) promoted the growth of *Blautia, Parabacteroides* and *Faecalibacterium* in fecal pools of healthy adults compared to untreated controls. These results validate the findings from the first and second i-screen results for acid treated high and low acyl gellan oligomer samples. Higher fold-change values in the three genera were obtained with low acyl acid treated gellan oligomers. Furthermore, high and low acyl gellan oligomers produced with enzyme treatment were also effective at increasing the growth of the three genera in the same fecal pool.

Using the H2 fecal pool (Table 4b entries 9-12), it may be seen that SOSs (acid and enzyme treated) increased the fold change of *Blautia, Parabacteroides, Faecalibacterium* and bacteria from *Clostridium* cluster XVIII. SOSs (acid treated) promoted the highest fold change of *Faecalibacterium* (21.93) and *Parabacteroides* (7.25). *Clostridium* XVIII cluster fold-change values ranged from 12.66 to 55.91. As a point of reference, most of the *Clostridium* XVIII and *Clostridium* XIVa clusters found in the gut produce acetate (a few strains in *Clostridium* XIVa cluster also produces butyrate along with acetate), also based on the genomic analysis (metabolic network) both clusters produce no toxins. Narushima (2014).

Using the IBD fecal pool (Table 4b entries 13-16), the results show that SOSs (from low acyl gellan) promoted the highest fold-change values of *Parabacteroides*. Acid treated low acyl gellan oligomers exhibited the highest fold-change of *Faecalibacterium*. The fold-change of *Clostridium* cluster XVIII was also increased ranging from 30.84 to 98.28. It is of interest to note that there is a significant growth of *Parabacteroides* in SOSs. *Parabacteroides* digest healthful, high fiber diets, they protect from inflammation. These bacteria are missing from patients suffering from inflammatory bowel diseases. Martinez (2010), Noor (2010), Segata (2012), and Zitomersky (2013).

Table 5 summarizes the observed effect for a second i-screen analysis of Sample Nos. 9-16 (and Comparative Samples 1-16, as well as Livaux™ supplement, Inulin, and Amoxicillin) on a panel of eight bacteria (Lachnospiraceae unclassified ("Lachn.U."), *Clostridium* XIVa ("ClXIVa"), *Bifidobacterium* ("Bifid."), *Coprococcus* ("Copro.") *Blautia* ("Blaut."), *Phascolarctobacterium*, ("Phasc."), *Faecalibacterium* ("Faecal."), *Butyricicoccus* ("Butyr."), and *Parabacteroides* ("Para.")), where the reported results are relative to an untreated control (growth denoted as 1.0).

TABLE 5

Effect of selected SOSs (SN9-SN16) and Comparative Samples (CS) against a panel of eight bacteria.

| Sample | Lachn. U. | ClX1Va | Bifid. | Copro. | Blaut. | Phasc. | Faecal. | Butyr. | Para. |
|---|---|---|---|---|---|---|---|---|---|
| SN9 | 2.42 | 1.00 | 0.65 | 1.02 | 2.21 | 1.08 | 30.71 | 0.95 | 6.79 |
| SN10 | 1.19 | 0.93 | 0.73 | 0.83 | 3.20 | 1.37 | 51.54 | 0.93 | 15.99 |
| SN11 | 1.20 | 1.07 | 0.38 | 1.22 | 2.56 | 1.97 | 30.24 | 1.12 | 26.30 |
| SN12 | 0.53 | 1.17 | 1.34 | 0.31 | 2.28 | 2.90 | 48.73 | 0.73 | 37.79 |
| SN13 | 2.06 | 0.96 | 0.80 | 0.88 | 2.12 | 1.04 | 17.49 | 0.91 | 9.36 |
| SN14 | 1.16 | 0.83 | 0.86 | 0.78 | 3.00 | 1.29 | 43.63 | 0.99 | 17.67 |
| SN15 | 1.14 | 0.88 | 0.67 | 1.12 | 4.96 | 1.24 | 29.05 | 0.84 | 6.59 |
| SN16 | 1.08 | 0.80 | 1.32 | 0.82 | 2.30 | 2.11 | 11.24 | 0.92 | 31.01 |
| CS1 | 3.90 | 0.62 | 1.01 | 0.52 | 1.86 | 1.21 | 3.74 | 0.55 | 0.49 |
| CS2 | 3.54 | 0.52 | 0.62 | 0.39 | 1.26 | 1.31 | 3.09 | 0.67 | 0.53 |
| CS3 | 3.08 | 0.54 | 0.83 | 0.56 | 1.91 | 1.58 | 3.63 | 0.77 | 0.52 |
| CS4 | 2.82 | 0.54 | 0.88 | 0.51 | 1.68 | 1.64 | 3.20 | 0.71 | 0.55 |
| CS5 | 1.67 | 0.55 | 0.43 | 0.71 | 1.31 | 1.94 | 3.49 | 0.91 | 0.71 |
| CS6 | 2.45 | 0.54 | 0.89 | 0.50 | 1.74 | 1.67 | 2.26 | 0.84 | 0.47 |
| CS7 | 1.52 | 0.71 | 0.53 | 0.93 | 1.15 | 1.09 | 1.35 | 1.49 | 0.75 |
| CS8 | 1.13 | 0.51 | 0.65 | 0.58 | 0.55 | 1.27 | 1.13 | 1.19 | 0.46 |

TABLE 5-continued

Effect of selected SOSs (SN9-SN16) and Comparative Samples (CS) against a panel of eight bacteria.

| Sample | Lachn. U. | ClX1Va | Bifid. | Copro. | Blaut. | Phasc. | Faecal. | Butyr. | Para. |
|---|---|---|---|---|---|---|---|---|---|
| CS9 | 1.22 | 1.02 | 0.74 | 1.27 | 0.92 | 0.98 | 1.46 | 1.25 | 0.98 |
| CS10 | 2.03 | 0.66 | 0.84 | 0.87 | 1.49 | 1.53 | 3.64 | 0.71 | 0.80 |
| CS11 | 1.20 | 1.07 | 0.60 | 0.84 | 1.13 | 1.86 | 1.77 | 0.72 | 1.38 |
| CS12 | 2.35 | 0.54 | 2.13 | 0.57 | 2.72 | 1.79 | 2.18 | 0.67 | 0.58 |
| CS13 | 0.72 | 0.59 | 1.95 | 0.56 | 5.15 | 2.17 | 1.81 | 0.68 | 0.52 |
| CS14 | 1.17 | 1.05 | 0.56 | 1.07 | 1.31 | 1.24 | 1.04 | 0.68 | 2.80 |
| CS15 | 1.23 | 0.81 | 1.05 | 0.83 | 1.79 | 1.21 | 1.15 | 1.33 | 7.16 |
| CS16 | 1.38 | 0.73 | 1.52 | 0.82 | 2.52 | 1.50 | 1.25 | 1.00 | 8.26 |
| CS17 | 1.19 | 0.82 | 1.11 | 1.03 | 1.79 | 1.28 | 0.94 | 1.07 | 7.01 |
| CS18 | 0.97 | 0.72 | 1.68 | 1.15 | 1.53 | 1.07 | 1.14 | 0.74 | 0.79 |
| CS19 | 0.73 | 0.81 | 3.35 | 0.82 | 3.64 | 0.78 | 0.93 | 0.89 | 0.62 |
| CS20 | 0.04 | 0.03 | 0.24 | 0.04 | 0.23 | 0.08 | 0.37 | 0.00 | 12.10 |

Table 6 summarizes the compositional makeup of Comparative Samples 1-16 used in the second screen.

TABLE 6

Summary of Comparative Samples ("CS") 1-16.

| CS | Comments |
|---|---|
| CS1 | Semi-finished lemon pectin (67.3% DE; IV 5.3 dL/g).[a] |
| CS2 | Lime pectin (55.5% DE; IV 5.0 dL/g; random esterification pattern ("EP")).[a] |
| CS3 | Semi-finished orange pectin (55.7% DE; IV 3.1 dL/g).[a] |
| CS4 | Orange pectin (28.3% DE; IV 3.0 dL/g), random EP.[a] |
| CS5 | Semi-finished sugar beet pectin (53.0% DE, IV 2.4 dL/g, 18.0% DAc).[a] |
| CS6 | Orange pectin (55.1% DE, IV 1.7 dL/g).[a] |
| CS7 | Sugar beet pectic oligosaccharides ("POS") obtained by treating sugar beet pectin with pectin lyase and polygalacturonase; passing through 0.2 micron filter; and subjecting permeate to 3 kDa filter. |
| CS8 | Lemon POS (methylated) obtained by treating lemon pectin with pectin lyase; subjecting to 70 kDa filter; and then subjecting permeate to 3 kDa filter. |
| CS9 | Lemon POS (non-methylated) obtained by treating lemon pectin with pectin methyl esterase and pectin lyase; subjecting to 70 kDa filter; and then subjecting permeate to 3 kDa filter. |
| CS10 | Insoluble citrus fiber. |
| CS11 | κ-Carrageenan (partially modified: typically 17-18% nu). |
| CS12 | Pectin extracted from peel waste. |
| CS13 | Sugar beet HR (hairy region, or RG1, rhamnogalacturonan 1) obtained by treating sugar beet HR with pectin lyase and polygalacturonase; subjecting to 0.2 micro filter; and subjecting retentate to 10 kDa filter. |
| CS14 | Xanthan polysaccharide prepared from non-pyruvylated xanthan ("NPX"). |
| CS15 | NPX oligosaccharide derived from CS14 by treating with xanthanase; followed by passing through a 5 kDa filter. |
| CS16 | Xanthan polysaccharide derived from clarified xanthan gum (KELTROL ® T xanthan) powder. |
| CS17 | Xanthan oligosaccharide derived from xanthan polysaccharide (cf. CS16) by additional xanthanase digestion; followed by passing through 5 kDa filter. |
| CS18 | Livaux ™ kiwifruit powder (commercial product claiming promotion of F. prausnitzii). |
| CS19 | Inulin (commercially available from Sigma). |
| CS20 | Amoxicillin (commercially available from Sigma). |

[a]For semi-finished pectins and pectic oligosaccharides (POS), pectin samples were treated using either pectin methyl esterase for lower degree of esterification (DE) or polygalacturonase and pectin lyase for pectins with lower MW/IV (molecular weight/intrinsic viscosity).

Based on the Table 5 results, it may be seen that all sphingan oligosaccharides exhibited the highest growth of *Faecalibacterium* relative to all of the Comparative Samples. In particular, the highest growth of *Faecalibacterium* was shown by gellan oligosaccharides (about 52-fold) obtained from GELRITE™ MK gellan (5 kDa cutoff (SN10)), rhamsan oligosaccharides (about 49-fold) obtained from native rhamsan (SN12), and gellan oligosaccharides (43-fold) obtained from GELRITE™ MK (10 kDa cutoff (SN14)). Interestingly, the Livaux™ product—promoted as having *Faecalibacterium* growth activity (see, e.g., livaux-.com/livaux-gi-problem/)—showed only a 1.14-fold increase in *Faecalibacterium* growth activity compared to untreated control. The relatively low *Faecalibacterium* growth activity for Livaux™ product activity is consistent with published data. (US20170326190A1).

A comparison of the results from Table 4 and Table 5 shows, in certain instances, variability for selected samples (cf, SN10 (188.31 v. 51.54) and SN12 (70.44 v. 48.73)). Additional analysis of selected data shows that the coefficient of variation (viz., the ratio of the standard deviation to the mean) for selected sphingans may vary from about 7% to about 32%, and in some instances, up to about 80%.

Based on the Table 5 results, it may be seen that all sphingan oligosaccharides exhibited an increase in growth activity for *Blautia* (viz., 2-5 fold increase relative to untreated control).

Data not shown reveals that all sphingan oligosaccharides exhibited a decrease in growth activity for *Escherichia/Shigella* (ca. 9-36% reduction relative to untreated control). This should be contrasted to Livaux™ product, which exhibited an increase in growth activity for *Escherichia/Shigella* (ca. 45% increase relative to untreated control).

III. Example III. Effect of a Gellan Gum on the Activity and Composition of the Luminal and Mucosal Gut Microbiome in the Human Gastrointestinal Tract A. Material and Methods, Design of the SHIME Experiment, and Typical SHIME Reactor Setup Aspects of the Simulator of the Human Intestinal Microbial Ecosystem (or SHIME) are known. (See, e.g., Molly (1993), Possemiers (2004), Possemiers (2017), Van de Wiele (2013), Van den Abbeele (2012), and Van den Abbeele (2013).)

The typical reactor setup of the SHIME, representing the gastrointestinal tract of the adult human, was described by Molly (1993). It consists of a succession of five reactors simulating the different parts of the human gastrointestinal tract (e.g., stomach (V1), small intestine (V2), ascending colon (V3), transverse colon (V4), and descending colon (V5)). The first two reactors are of the fill-and-draw principle to simulate different steps in food uptake and digestion, with peristaltic pumps adding a defined amount of SHIME feed (140 mL 3×/day) and pancreatic and bile liquid (60 mL 3×/day), respectively to the stomach (V1) and small intestine (V2) compartment and emptying the respective reactors after specified intervals. The last three compartments simulate the large intestine. These reactors are continuously stirred; they have a constant volume and pH control. Retention time and pH of the different vessels are chosen in order to resemble in vivo conditions in the different parts of the colon. Upon inoculation with fecal microbiota, these reactors simulate the ascending (V3), transverse (V4) and descending (V5) colon. Inoculum preparation, retention time, pH, temperature settings and reactor feed composition were previously described by Possemiers (2004). Upon stabilization of the microbial community in the different regions of the colon, a representative microbial community is established in the three colon compartments, which differs both in composition and functionality in the different colon regions.

The human intestinal tract harbors a large and complex community of microbes which is involved in maintaining human health by preventing colonization by pathogens and by producing nutrients. Microorganisms are not randomly distributed throughout the intestine and those adhering to the gut wall play an important role as a 'barrier' against pathogens, instructing mucosal immune responses and occupying a niche at the expense of potentially harmful colonizers. However, current in vitro strategies do not allow to culture the fraction of microorganisms which adhere to the gut mucosa and are limited to modeling of the luminal microbial community. This means that an important part of the gut ecosystem is not taken into account and potentially crucial information is lost.

To overcome this problem, the SHIME system was modified to account for colonization of the mucus layer. (See, e.g., Van den Abbeele (2012) and Van den Abbeele (2013).) The modified SHIME system is known as M-SHIME, which allows to culture both the luminal and mucus-associated microbial community over periods of several weeks.

Inclusion of the mucosa compartment increases the value and modeling capacity of the SHIME and allows to evaluate whether a specific treatment is also able to modulate the mucosa-associated microbial community.

1. Adapted SHIME Setup for Study

The SHIME setup was adapted from a TWINSHIME configuration to a TripleSHIME configuration, which included a vessel (or reactor) for the stomach, small intestine, proximal colon, and distal colon for each of the donors. The TripleSHIME configuration permitted comparison of the three different conditions in parallel. Potential fermentation of a gellan gum by the microbiota of three different human donors was evaluated (Donor A: female, 28 y Donor B: female, 41 y; Donor C: female, 34 y). The colon regions were limited to two regions as compared to three regions in the TWINSHIME. The retention times and pH ranges were optimized in order to obtain results that are representative for a full gastrointestinal tract simulation. In practice, in TripleSHIME experiments, instead of working with 2 units, each composed of an AC-TC-DC configuration (ascending, transverse and descending colon), one used 3 PC-DC units. Upon inoculation with a fecal microbiota of a human adult, these reactors simulate the proximal colon (PC; pH 5.6-5.9; retention time=20 h; volume of 500 mL) and distal colon (DC; pH 6.6-6.9; retention time=32 h; volume of 800 mL).

The SHIME experiment for this study consisted of three stages (Stabilization, Control, and Treatment) that spanned over a seven-week period.

Stabilization Period:

After inoculation of the colon reactors with an appropriate fecal sample, a two-week stabilization period allowed the microbial community to differentiate in the different reactors depending on the local environmental conditions. During this period the basic nutritional matrix was provided to the SHIME to support the maximum diversity of the gut microbiota originally present in the fecal inoculum.

Control Period:

During this two-week reference period, the standard SHIME nutrient matrix was further dosed to the model for a period of 14 days. Analysis of samples in this period allows to determine the baseline microbial community composition and activity in the different reactors, which was used as a reference for evaluating the treatment effects.

Treatment Period:

During this three-week period, the SHIME reactor was operated under nominal conditions, but with a diet supplemented with the test product. Samples taken from the colon reactors in this period allow investigation of the specific effect on the resident microbial community composition and activity.

B. Analysis of the Microbial Community Composition and Activity

A feature of the SHIME is the possibility to work with a stabilized microbiota community and to regularly collect samples from the different intestinal regions for further analysis. The large volumes in the colonic regions allow collection of sufficient volumes of liquids each day, without disturbing the microbial community or endangering the rest of the experiment.

A number of microbial parameters are monitored throughout the entire experiment as part of the standard SHIME experiment. These measurements are necessary to evaluate the performance of the model and allow monitoring basic changes in the microbial community composition and activity due to the prebiotic treatment.

1. Analysis of the Microbial Community Composition and Activity

Acid/Base Consumption:

the production of microbial metabolites in the colon reactors alters the pH. Without continuous pH control (through the addition of acid or base), the pH would exceed the fixed intervals. Consumption of acid/base is continuously monitored during a SHIME experiment.

Total Gas Production:

the evaluation of total gas production is an important aspect related to potential tolerance issues in case of final application. However, online total gas production measurements are difficult in continuous models of the gut, due to continuous in-and-outflow of masses. Total gas production analysis is therefore typically assessed in batch setups.

2. Microbial Community Activity (3×/Week)

Short-Chain Fatty Acids (SCFA):

the concentrations of acetic acid, propionic acid and butyric acid were analyzed.

Lactate:

precursor of SCFA and potential antimicrobial agent.

Ammonium and Branched SCFA (isobutyric acid, isovaleric acid and isocaproic acid) are markers of proteolytic fermentation, with rather adverse effects on host health.

Microbial community composition (1×/week); samples were taken for 16S-targeted Illumina sequencing.

C. Gellan Gum Used for Studies

The test product included a food-grade gellan gum, KELCOGEL® LT100-P gellan gum ("Gellan Gum"). KELCO- GEL® LT100-P gellan gum is a native (high acyl) gellan gum. The product was tested at an in vitro dose of 1 g/d, which corresponds to an in vivo dosage of 2 g/d.

D. Stability of the SHIME Setup

During the control period, SCFA levels were very stable within the three SHIME units (on average, the levels were 94.4% similar between consecutive time points in the control period), clearly indicating stability of the microbial community in terms of activity and composition. Stable reactor conditions increase confidence that any effect observed during the treatment truly resulted from the administered test product.

E. Overall Fermentative Activity

1. Acid/Base Consumption

The consumption of acid and base reflects the overall microbial activity throughout a SHIME experiment. To ensure that optimal environmental conditions are maintained, the pH in a SHIME system is controlled by pH controllers between 5.6-5.9 in the proximal colon and 6.6-6.9 in the distal colon. Upon stabilization of the microbial community in the different reactors (starting from 2 weeks after inoculation), base-acid consumption is generally low. However, during a treatment, bacteria may produce increased amounts of SCFA. As a consequence, the environment in the reactors will acidify, requiring administration of base to the respective reactors to keep them in the pre-set pH-ranges. As a result, the acid/base consumption will increase. By measuring the acid/base consumption throughout an experiment, one is able to estimate the potential effect of the test product on the microbial community activity. However, it must be noted that acid/base consumption is only a rough indicator of microbial fermentation as not all acids produced via fermentation cause a similar pH decrease (acids with lower pKa, such as acetate, effectively decrease pH), while conversion of acids to one another can also affect pH (e.g., conversion of acetate/lactate to propionate/butyrate increases pH). Actual measurement of microbial metabolites (such as SCFA and lactate) provides a more accurate reading.

The Table 7 data shows that the overall fermentation of the test product showed similar trends over the three donors tested in both the proximal and distal colon compartment.

TABLE 7

Average weekly base-acid consumption (mL/day) during two control (C1 and C2) and three treatment (TR1-TR3) weeks for the treatment with Gellan Gum for three different donors (A, B and C) in the proximal colon (PC) reactors and average acid/base consumption over the entire control (n = 6) and treatment (n = 9) period.

| Periods | PC | | | DC | | |
|---|---|---|---|---|---|---|
| | A | B | C | A | B | C |
| C1 | 1.1 | 2.2 | 0.9 | 15.9 | 13.8 | 18.5 |
| C2 | 0.8 | 0.5 | 1.1 | 17.3 | 15.4 | 16.1 |
| TR1 | −0.4 | −0.7 | 0.0 | 21.6 | 18.2 | 19.6 |
| TR2 | 1.6 | 1.4 | 0.5 | 15.0 | 15.1 | 17.5 |
| TR3 | 4.3 | 3.1 | 2.9 | 19.3 | 17.2 | 21.1 |
| CON(ave) | 1.0 | 1.3 | 1.0 | 16.6 | 14.6 | 17.3 |
| TRT(ave) | 1.8 | 1.3 | 1.1 | 18.6 | 16.8 | 19.4 |

In the proximal colon, acidification was very limited, however a trend towards increased base consumption was observed during the final week of treatment for all donors tested. In the distal colon, acidification was more pronounced during the control period as compared to the proximal colon. This is explained by the fact that the physical transfer of the more acidic proximal colon suspension (pH=5.6-5.9) to the distal colon automatically provokes higher base consumption in this distal colon to keep the pH in the correct interval (pH=6.6-6.9). Supplementation of the test product resulted in a slightly elevated base consumption immediately after the initiation of treatment for all donors tested.

2. Gas Production

Since gasses are a major endpoint of fermentative activity by gut microbes, changes in gas production provide an indication of the overall fermentation profile. Because gas production is not monitored in the continuous SHIME model, given the regular flushing of the headspace with nitrogen gas (to ensure anaerobiosis), gas production is evaluated in separate short-term batch incubations. During such incubations, the same dose of the product under investigation is supplied to a microbiota derived from the proximal colon of the SHIME during the control period, thus mimicking the processes that occur when initiating the treatment in the continuous SHIME model.

Donor-dependent effects were observed in terms of gas production (data not shown). Whereas a slightly increased gas production was observed for Donor B upon treatment with the test product, the treatment resulted in a slightly reduced gas production for the other donors. Overall, gas production was most intense during the 6-24 h time interval for all conditions. Only during the 4-6 h time interval, a consistent (but mild) increase in gas production was observed over all donors upon treatment with the test product, whereas the other time intervals were characterized by donor-specific differences.

Overall, the treatment with Gellan Gum hardly affected gas production by the gut microbiota for the three donors tested.

F. Analysis of the Microbial Community Activity

1. Short Chain Fatty Acid (SCFA) Production

The information that follows describes the effect of the test product on SCFA production in the Triple-SHIME experiment. SCFA production results from carbohydrate metabolism in the colon and is related with various health effects. The most abundant SCFAs are acetate, propionate and butyrate. SCFAs are well-known to play a crucial role in gut health. Acetate can be used as an energy source for the host and as a potential substrate for lipid synthesis in the body. Moreover, it is an important byproduct in the synthesis of butyrate and can exert antimicrobial effects against pathogens. However, the health-promoting effects are mainly attributed to propionate and butyrate, which act as the main energy sources for the gut epithelium and have shown protective effects against inflammation and colon cancer. Cummings (1987). Propionate is known to be transported to the liver, where it has a cholesterol-lowering effect in plasma and positively affects glycemic control. (See Wright (1990), Demigne (1995), and Wong (2006).)

In summary, beneficial effects of the investigated substrates on SCFA production therefore include an increase of acetate, propionate and/or butyrate production. The information that follows considers a direct comparison of the results for the three donors.

For optimal comparison of the different donors, the average SCFA levels for all three of them are presented for each of the different SCFA (per week and per period).

2. Acetate Production

Figure 2A:
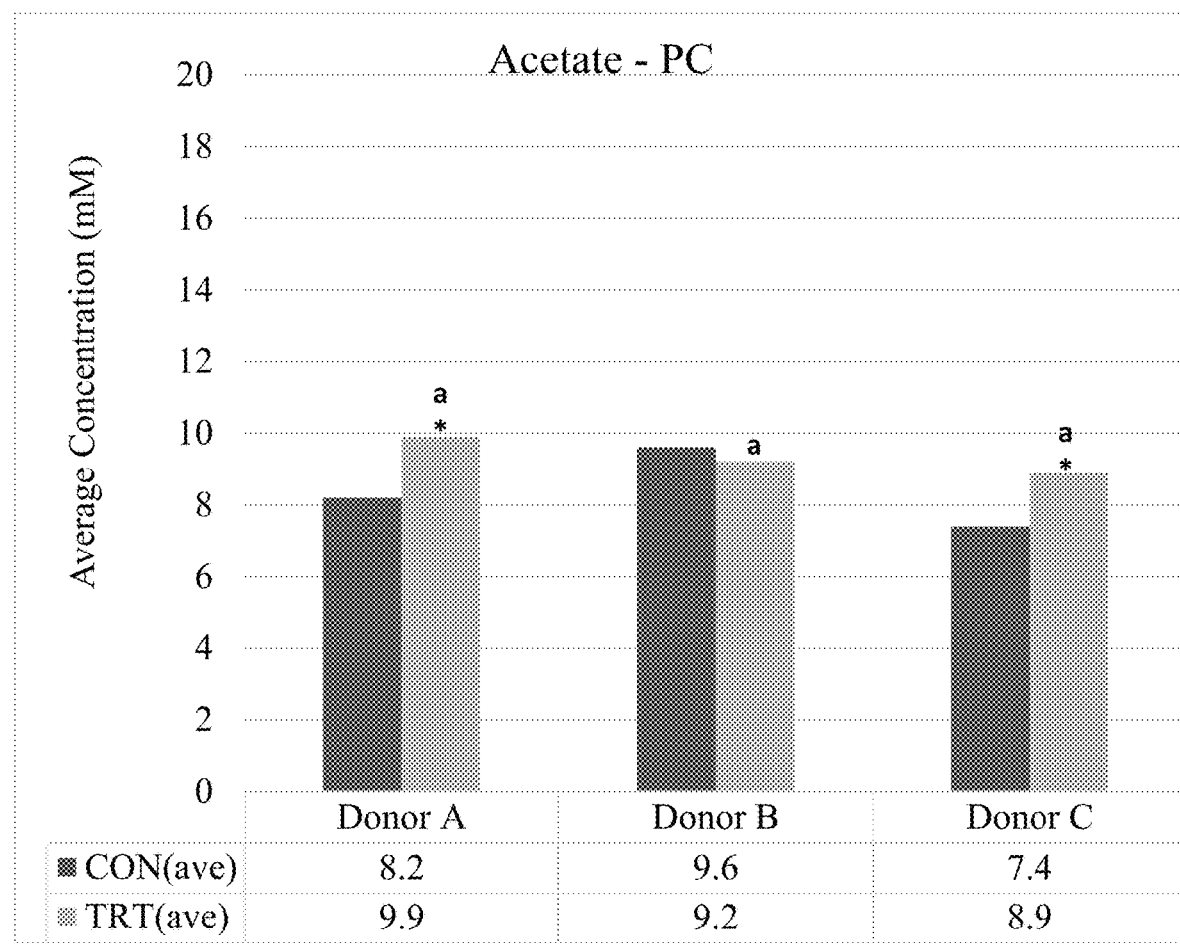
FIG. 2a. Average acetate production (mM) over the control (CON(ave), n=6) and treatment (TRT(ave), n=9) period for proximal colon (PC) reactor for the three different donors (A, B, and C), where * indicates statistically significant differences relative to the preceding period, while different letters indicate a statistical difference between different treatments; $p<0.05$.

Acetate can be produced by a wide range of gut microbes including among many others *Bacteroides* spp. (phylum Bacteroidetes) and Bifidobacteria. It followed that while Gellan Gum significantly increased acetate levels in the proximal colon of Donor A and C, acetate levels were unaffected for Donor B (FIG. 2a, Table 8). The biggest average increase was observed for Donor A (i.e., an increase of 1.7 mM or +21%). In contrast, in the distal colon, increased acetate levels upon Gellan Gum treatment were only observed for Donor B (FIG. 2b, Table 8) with an average increase of 2.1 mM (+6%) versus the control period.

TABLE 8

Figure 1B:
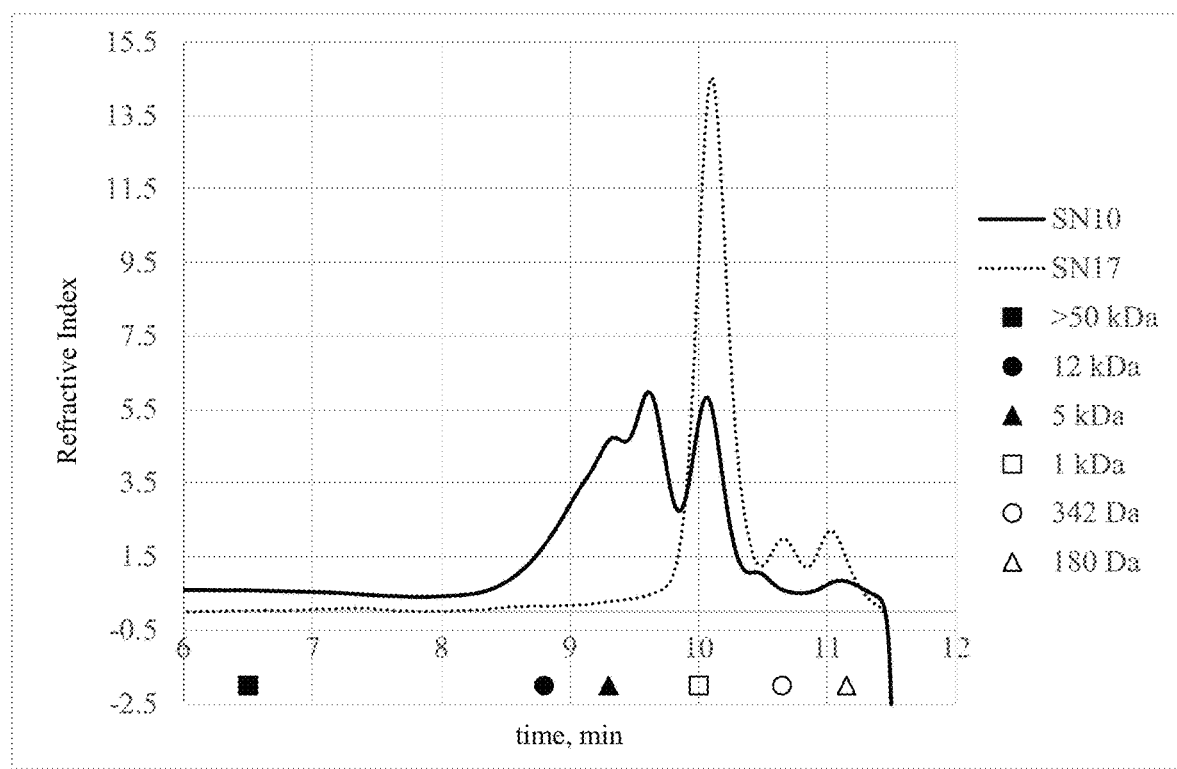
FIG. 1b. Size exclusion chromatogram for acid (SN10, solid line) and enzyme-treated (SN17, dashed line) sphingan poly- and oligosaccharides derived from a low acyl gellan showing Pullulan molecular weight standard elution times (viz., >50 kDa (6.5 min, filled square (■)), 12 kDa (8.8 min, filled circle (●)), 5 kDa (9.3 min, filled triangle (▲)), 1 kDa (10 min, empty square (□)), 342 Da (10.65 min, empty circle (○)), and 180 Da (11.15 min, empty triangle (Δ))).

Effect of Gellan Gum treatment on acetate production (in mM) in the proximal (PC) and distal colon (DC) reactors for the three different donors (A, B and C), and average weekly acetate production during control (C1 and C2) and treatment (TR1-TR3) weeks (see also FIGS. 1a-1b).

| Periods | PC | | | DC | | |
|---|---|---|---|---|---|---|
| | A | B | C | A | B | C |
| C1 | 8.5 | 11.7 | 7.4 | 38.9 | 36.0 | 37.7 |
| C2 | 8.0 | 7.4 | 7.4 | 35.9 | 34.8 | 36.5 |
| TR1 | 8.5 | 9.6 | 8.3 | 36.4 | 36.7 | 36.8 |
| TR2 | 9.5 | 8.0 | 7.5 | 35.2 | 37.2 | 35.5 |
| TR3 | 11.6 | 10.1 | 10.8 | 39.3 | 38.5 | 38.5 |
| CON(ave) | 8.2 | 9.6 | 7.4 | 37.4 | 35.4 | 37.1 |
| TRT(ave) | 9.9 | 9.2 | 8.9 | 37.0 | 37.5 | 36.9 |

3. Propionate Production

Figure 3A:
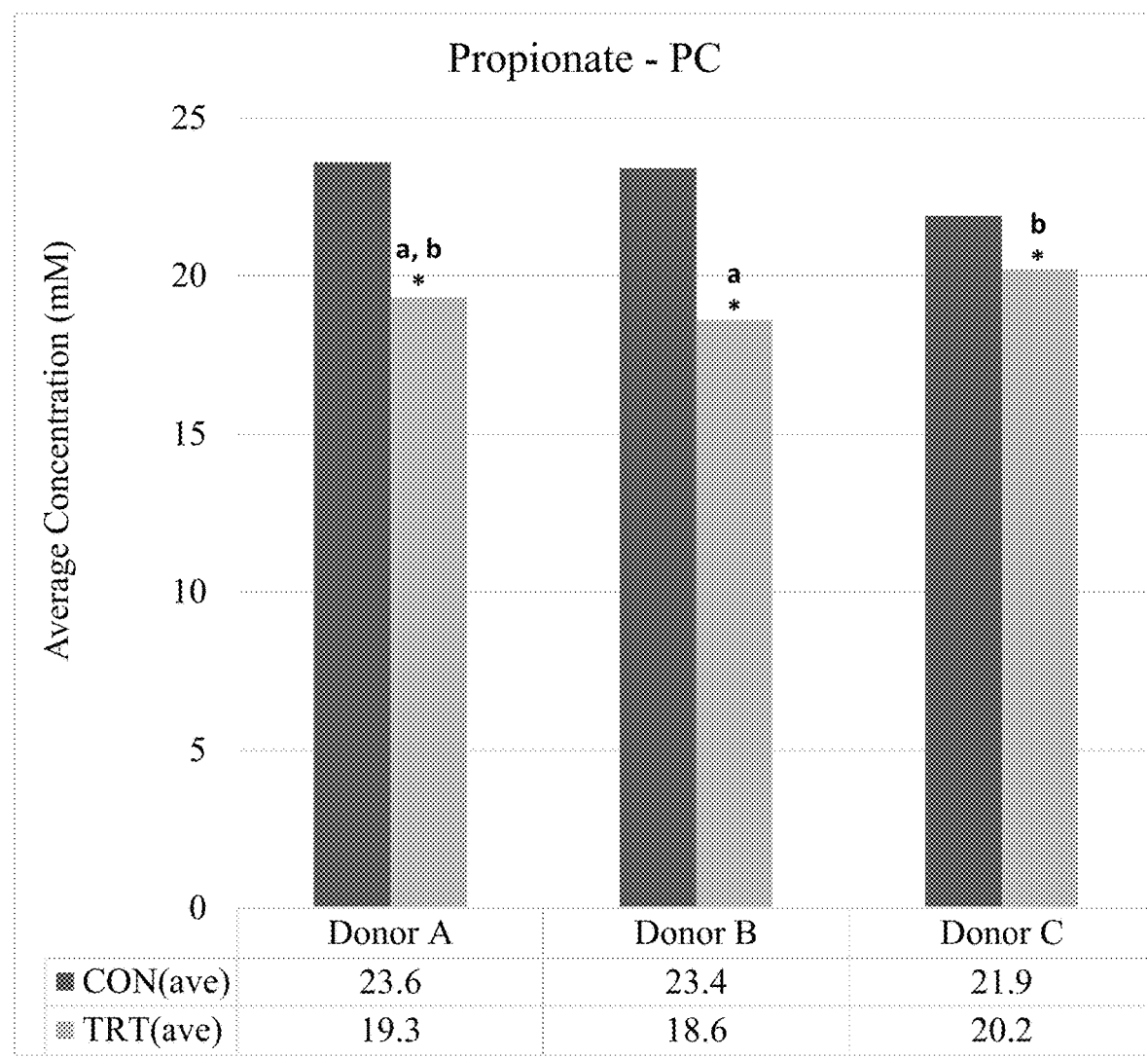
FIG. 3a. Average propionate production (mM) in the proximal colon (PC) reactor over the control (CON(ave), n=6) and treatment (TRT(ave), n=9) period for the three different donors (A, B, and C), where * indicates statistically significant differences relative to the preceding period, while different letters indicate a statistical difference between different treatments; $p<0.05$.
Figure 3B:
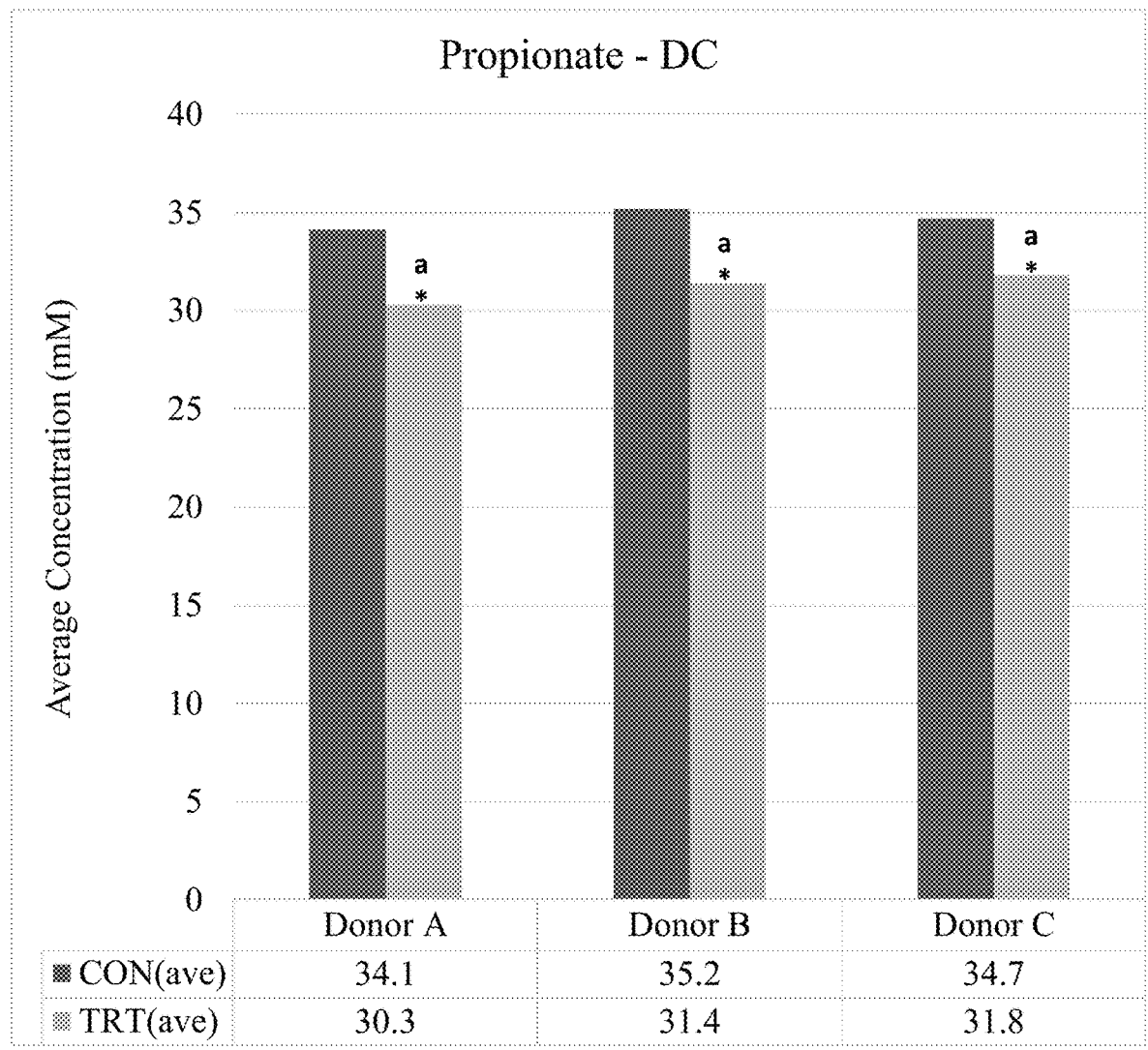
FIG. 3b. Average propionate production (mM) in the distal colon (DC) reactor over the control (CON(ave), n=6) and treatment (TRT(ave), n=9) period for the three different donors (A, B, and C), where * indicates statistically significant differences relative to the preceding period, while different letters indicate a statistical difference between different treatments; $p<0.05$.

Propionate can be produced by a wide range of gut microbes, with the most abundant propionate producers being *Bacteroides* spp. (phylum Bacteroidetes), *Veillonella* (phylum Firmicutes) and *Akkermansia muciniphila* (phylum Verrucomicrobia). For all three donors tested, Gellan Gum administration resulted in a significant decrease of propionate levels in response to the treatment for both colon regions (FIGS. 3a-3b, Table 9). In the proximal colon, a strong immediate decrease was observed for Donors A and B, whereas the effect was less pronounced for Donor C (i.e., a decrease of 1.7 mM (−8%) for Donor C versus −4.3 mM (−18%) and −4.8 mM (−20%) for Donors A and B, respectively). In the distal colon on the other hand, a more gradual decrease in propionate levels was observed for all donors. These findings are surprising in view of the studies of Edwards (1995) and Anderson (1988). For instance, Edwards (1995) stated that for Wistar rats gellan gum had no consistent effect on SCFA content, while Anderson (1988) reports that ingestion of large quantities of gellan gum resulted in a 23% decrease in propionate fecal content for female volunteers and a 33% increase in propionate fecal content for male volunteers.

TABLE 9

Figure 2B:
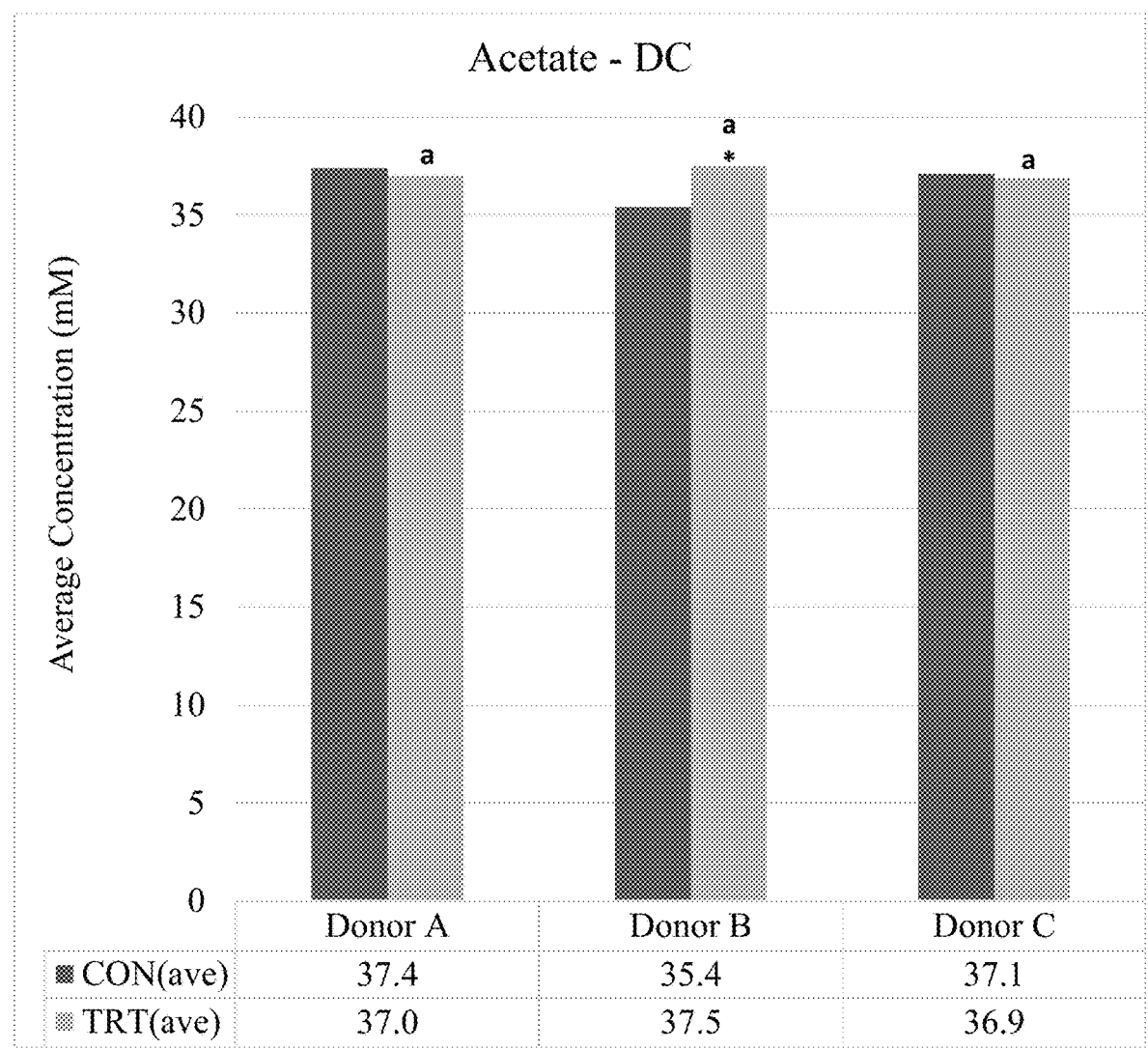
FIG. 2b. Average acetate production (mM) over the control (CON(ave), n=6) and treatment (TRT(ave), n=9) period for distal colon (DC) reactor for the three different donors (A, B, and C), where * indicates statistically significant differences relative to the preceding period, while different letters indicate a statistical difference between different treatments; $p<0.05$.

Effect of Gellan Gum treatment on propionate production (in mM) in the proximal (PC) and distal colon (DC) reactors for the three different donors (A, B and C), and average weekly propionate production during control (C1 and C2) and treatment (TR1-TR3) weeks (see also FIGS. 2a -2b).

| Periods | PC | | | DC | | |
|---|---|---|---|---|---|---|
| | A | B | C | A | B | C |
| C1 | 24.2 | 23.5 | 21.3 | 34.9 | 34.5 | 34.4 |
| C2 | 23.1 | 23.2 | 22.6 | 33.2 | 36.0 | 35.0 |
| TR1 | 19.3 | 19.1 | 21.5 | 32.7 | 33.9 | 33.9 |
| TR2 | 19.1 | 16.9 | 18.7 | 28.4 | 29.9 | 30.9 |
| TR3 | 19.5 | 19.6 | 20.4 | 29.8 | 30.3 | 30.7 |
| CON(ave) | 23.6 | 23.4 | 21.9 | 34.1 | 35.2 | 34.7 |
| TRT(ave) | 19.3 | 18.6 | 20.2 | 30.3 | 31.4 | 31.8 |

4. Butyrate Production

Figure 4A:
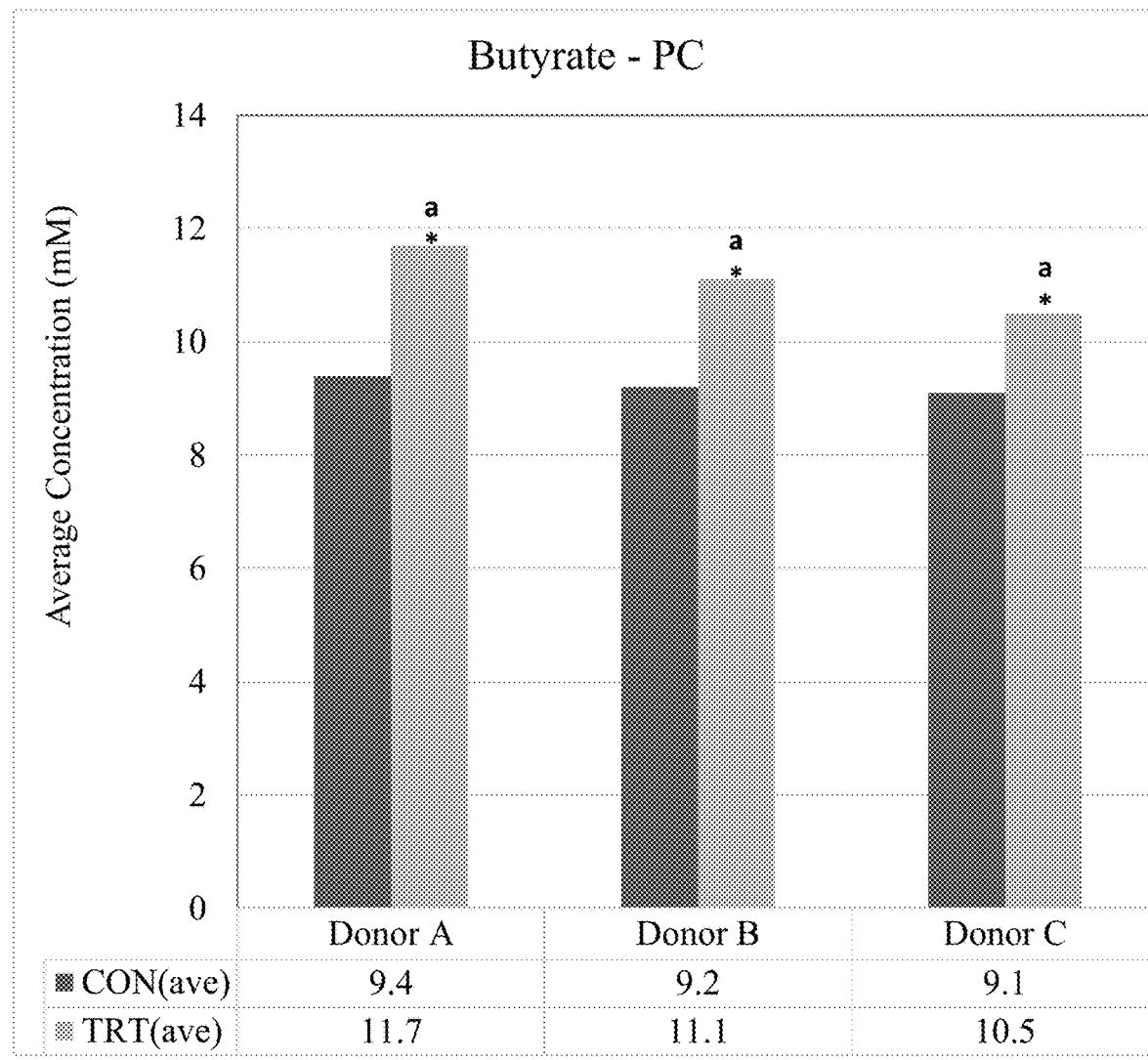
FIG. 4a. Average butyrate production (mM) in the proximal colon (PC) reactor over the control (CON(ave), n=6) and treatment (TRT(ave), n=9) period for the three different donors (A, B, and C), where * indicates statistically significant differences relative to the preceding period, while different letters indicate a statistical difference between different treatments; $p<0.05$.
Figure 4B:
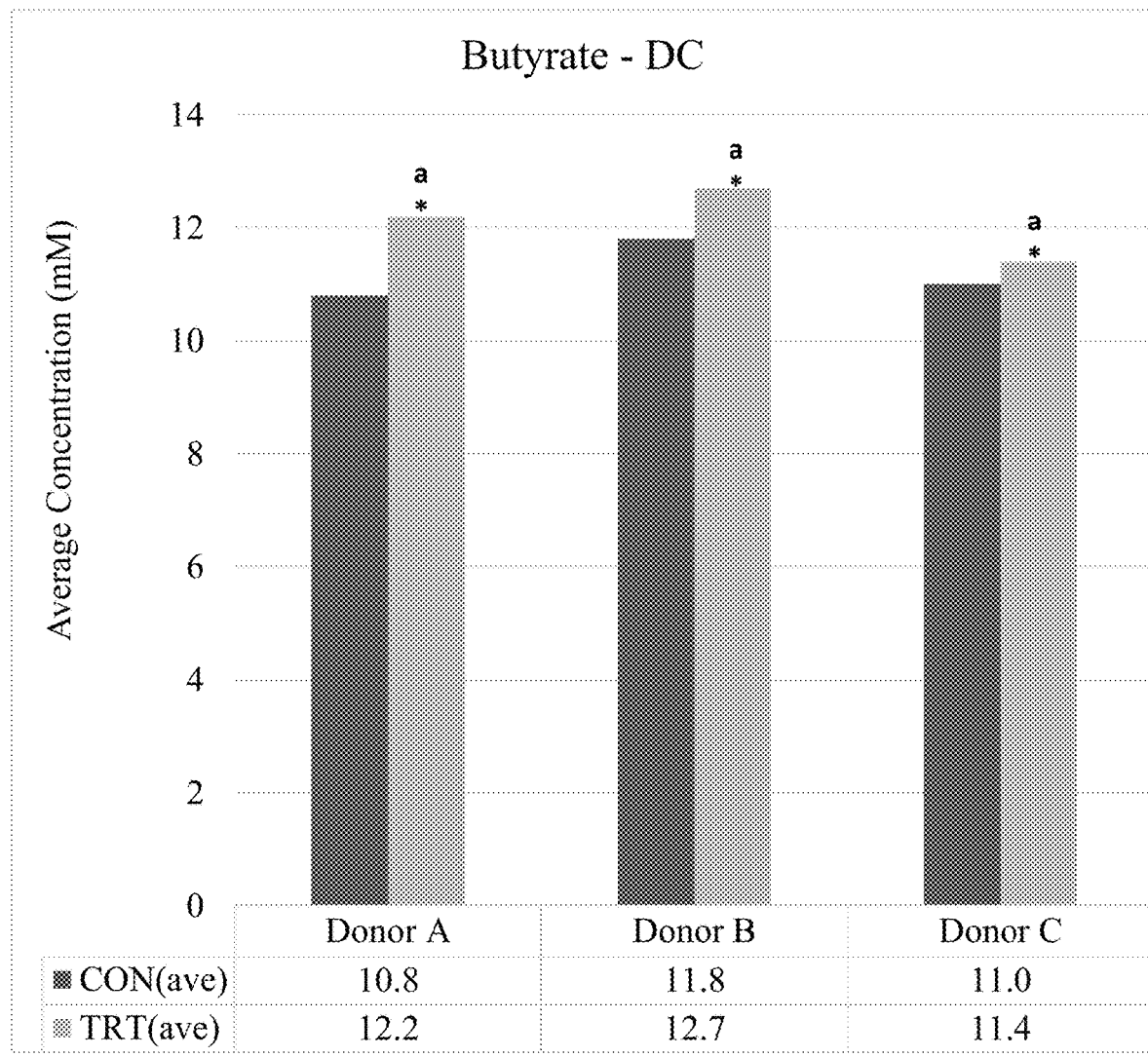
FIG. 4b. Average butyrate production (mM) in the distal colon (DC) reactor over the control (CON(ave), n=6) and treatment (TRT(ave), n=9) period for the three different donors (A, B, and C), where * indicates statistically significant differences relative to the preceding period, while different letters indicate a statistical difference between different treatments; $p<0.05$.

Butyrate is produced by members of the *Clostridium* clusters IV and XIVa (phylum Firmicutes). In a process referred to as cross-feeding, these microbes convert acetate and/or lactate (along with other substrates) to the health-related butyrate. Butyrate levels gradually increased upon supplementation of Gellan Gum in the proximal and to a lesser extent in the distal colon for all donors tested (FIGS. 4a-4b, Table 10). The effect was most pronounced in the proximal colon with significant increases of 2.3 mM (+24%), 1.9 mM (+21%) and 1.4 mM (+15%) for Donor A, Donor B and Donor C, respectively. In the distal colon, only Donor A had significantly increased butyrate levels upon Gellan Gum supplementation (i.e., an increase of 1.4 mM (+13%)).

TABLE 10

Effect of Gellan Gum treatment on butyrate production (in mM) in the proximal (PC) and distal colon (DC) reactors for the three different donors (A, B and C), and average weekly butyrate production during control (C1 and C2) and treatment (TR1-TR3) weeks (see also FIGS. 4a-4b).

| Periods | PC | | | DC | | |
|---|---|---|---|---|---|---|
| | A | B | C | A | B | C |
| C1 | 9.4 | 9.2 | 9.4 | 10.6 | 12.2 | 11.3 |
| C2 | 9.4 | 9.2 | 8.9 | 10.9 | 11.3 | 10.7 |
| TR1 | 10.8 | 9.1 | 9.0 | 11.4 | 11.5 | 10.1 |
| TR2 | 12.2 | 11.5 | 10.4 | 12.1 | 13.5 | 12.1 |
| TR3 | 12.0 | 12.8 | 12.2 | 13.0 | 13.2 | 12.2 |
| CON(ave) | 9.4 | 9.2 | 9.1 | 10.8 | 11.8 | 11.0 |
| TRT(ave) | 11.7 | 11.1 | 10.5 | 12.2 | 12.7 | 11.4 |

5. Lactate Production

The human intestine harbors both lactate-producing and lactate-utilizing bacteria. Lactate is produced by lactic acid bacteria and decreases the pH of the environment. Especially at low pH values, lactate can exert strong antimicrobial effects against pathogens. Another beneficial effect of lactate results from its conversion to butyrate and/or propionate. As different microbial species thus produce and convert lactate, an increase of lactate concentration can both result from an increased production as well as a decreased conversion. Therefore, one needs to be careful with data interpretation of lactate results.

In the proximal colon, lactate concentrations increased during the final week of treatment for all donors tested, reaching significance only for Donor A (Table 11). However, for the other donors high standard deviations could be observed during the final week of treatment as lactate concentrations gradually increased during the course of this week, i.e., from 0.19 mM at the beginning of the final treatment week till 0.73 mM at the end of the week for Donor B and from 0.13 mM till 0.46 mM for Donor C. In the distal colon, significantly increased lactate concentrations were observed during the final week of treatment for Donor C. For Donor A, a trend towards higher lactate concentrations upon Gellan Gum supplementation was observed, whereas lactate concentrations were not affected upon treatment for Donor B.

TABLE 11

Figure 5A:
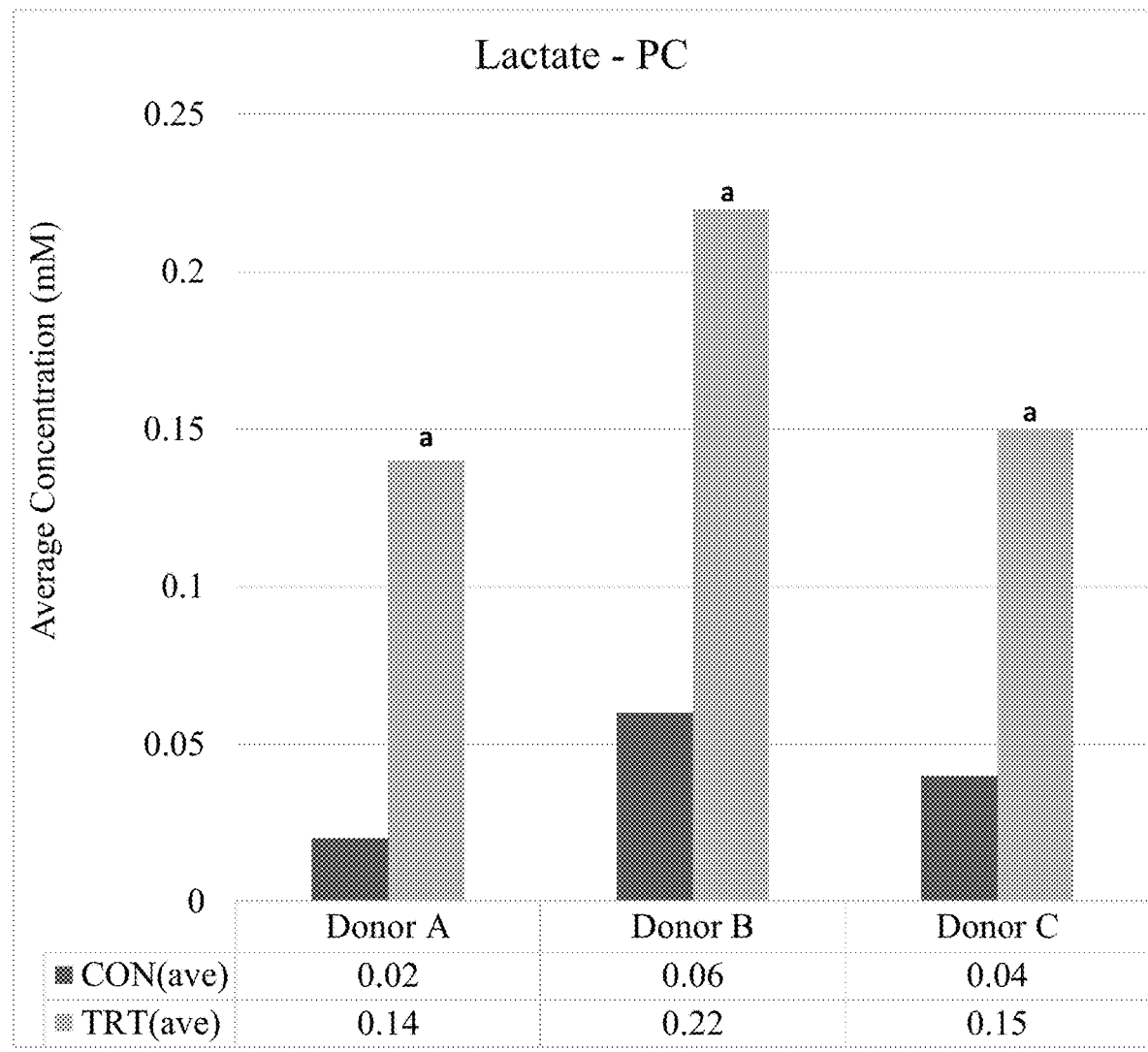
FIG. 5a. Average lactate production (mM) in the proximal colon (PC) reactor over the control (CON(ave), n=6) and treatment (TRT(ave), n=9) period for the three different donors (A, B, and C), where different letters indicate a statistical difference between different treatments; $p<0.05$.
Figure 5B:
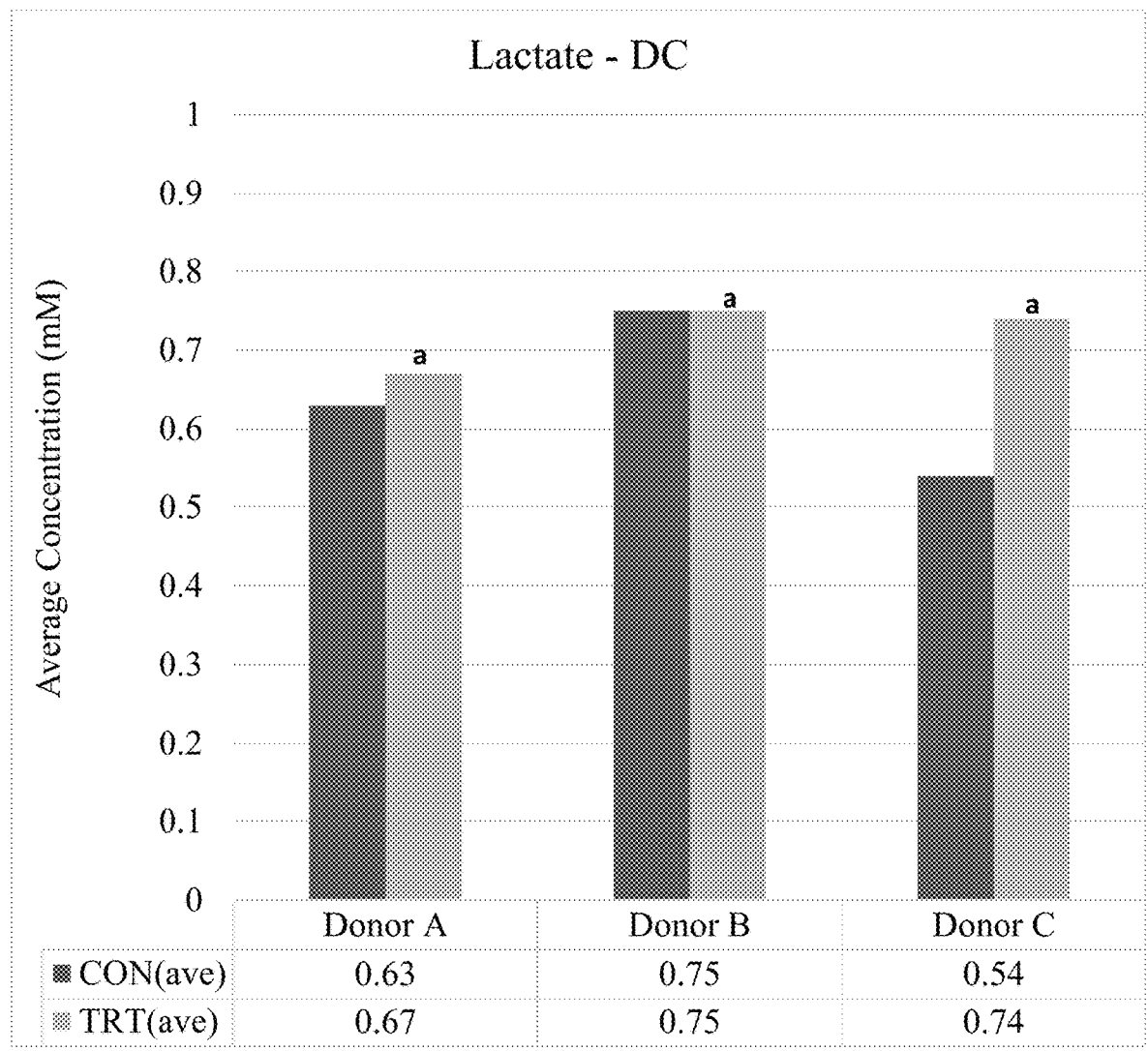
FIG. 5b. Average lactate production (mM) in the distal colon (DC) reactor over the control (CON(ave), n=6) and treatment (n=9) period for the three different donors (A, B, and C), where different letters indicate a statistical difference between different treatments; $p<0.05$.

Effect of Gellan Gum treatment on lactate production (in mM) in the proximal (PC) and distal colon (DC) reactors for the three different donors (A, B and C), and average weekly lactate production during control (C1 and C2) and treatment (TR1-TR3) weeks (see also FIGS. 5a-5b).

| Periods | PC | | | DC | | |
| --- | --- | --- | --- | --- | --- | --- |
| | A | B | C | A | B | C |
| C1 | 0.03 | 0.10 | 0.06 | 0.61 | 0.84 | 0.62 |
| C2 | 0.02 | 0.01 | 0.01 | 0.65 | 0.65 | 0.45 |
| TR1 | 0.03 | 0.05 | 0.05 | 0.57 | 0.84 | 0.60 |
| TR2 | 0.06 | 0.15 | 0.11 | 0.64 | 0.74 | 0.66 |
| TR3 | 0.32 | 0.45 | 0.30 | 0.79 | 0.67 | 0.96 |
| CON(ave) | 0.02 | 0.06 | 0.04 | 0.63 | 0.75 | 0.54 |
| TRT(ave) | 0.14 | 0.22 | 0.15 | 0.67 | 0.75 | 0.74 |

6. Ammonium and Branched SCFA Production

Figure 6A:
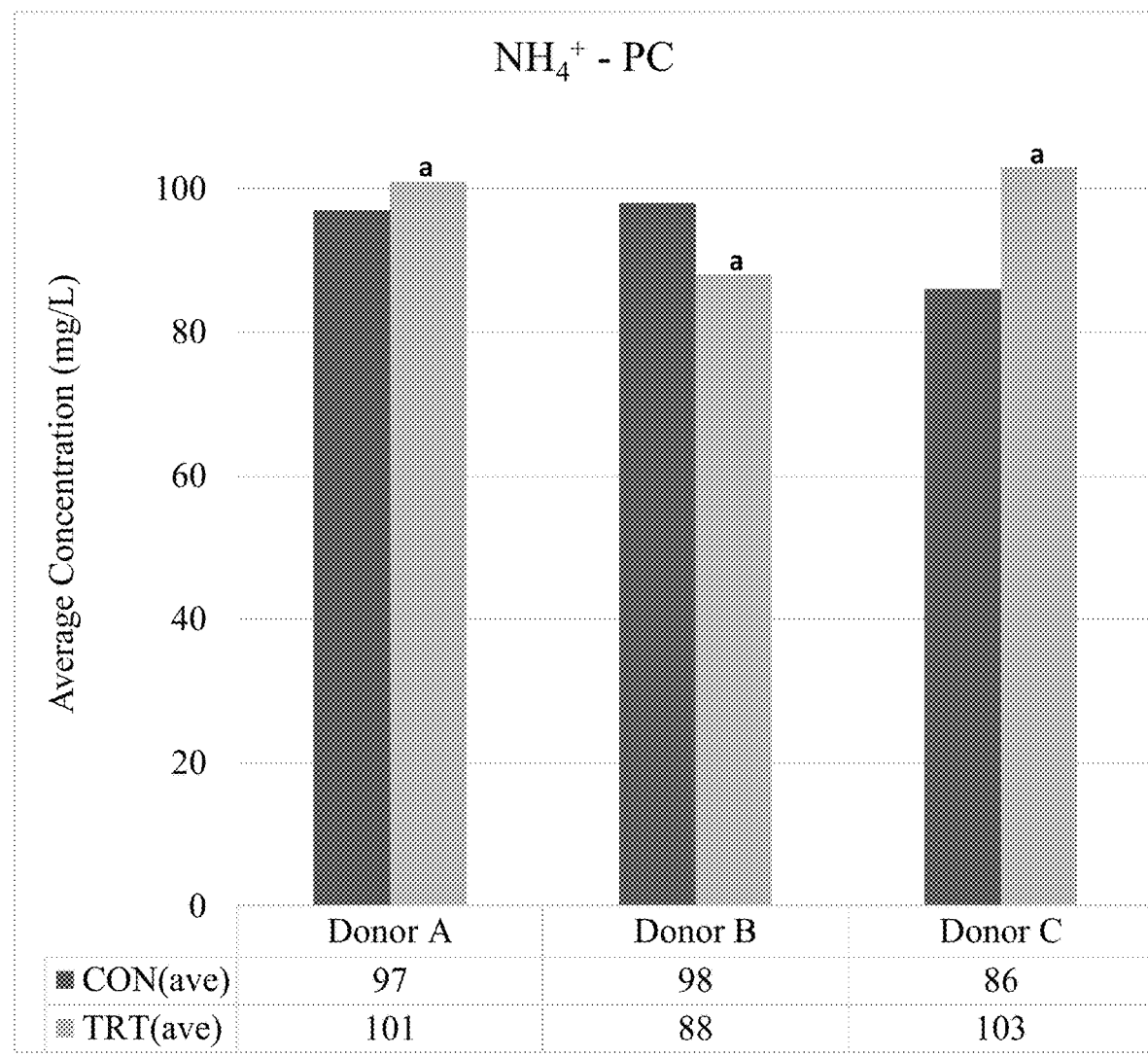
FIG. 6a. Average ammonium production (mg/L) in the proximal colon (PC) reactor over the control (CON(ave), n=6) and treatment (TRT(ave), n=9) period for the three different donors (A, B, and C), where different letters indicate a statistical difference between different treatments; p<0.05.
Figure 6B:
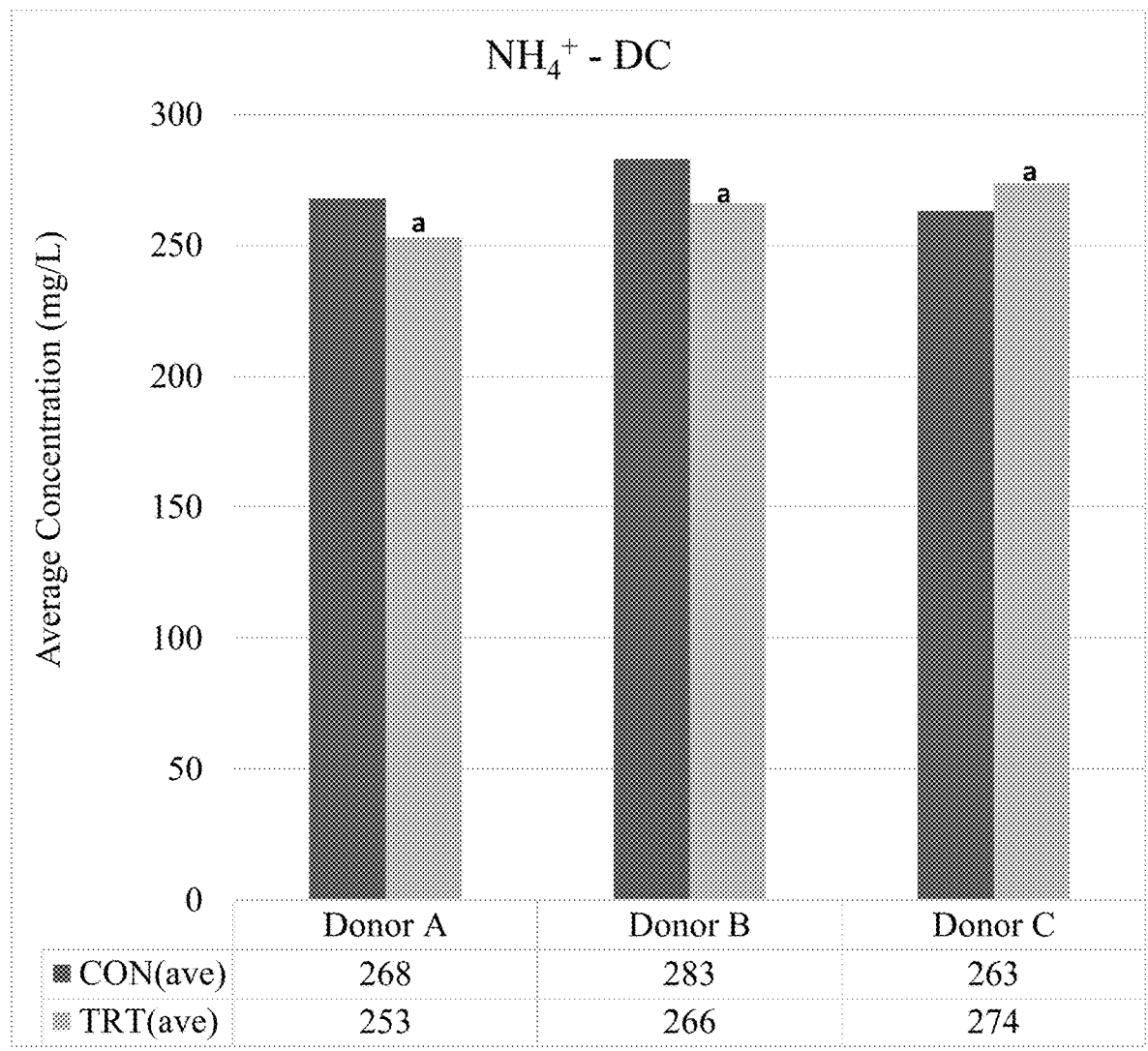
FIG. 6b. Average ammonium production (mg/L) in the distal colon (DC) reactor over the control (CON(ave), n=6) and treatment (TRT(ave), n=9) period for the three different donors (A, B, and C), where different letters indicate a statistical difference between different treatments; p<0.05.

Both the production of ammonium ($NH_4^+$) and branched SCFA (b-SCFA=sum of isobutyrate, isovalerate and isocaproate) result from protein degradation and reflect proteolytic activity of the gut microbiota. As the latter has been associated with direct and indirect detrimental health effects (for instance, colon carcinogenesis), a reduction in ammonium/b-SCFA production is considered as beneficial. FIG. 6a-6b (Table 12) presents the average ammonium (in mg/mL) production associated with the different treatments in the two colon regions, while FIG. 7a-7b (Table 13) presents the average branched SCFA production (in mM) associated with the different treatments in the two colon regions.

Ammonium levels were unaffected by the treatment with gellan gum in both proximal and distal colon for all donors tested, except for a slight increase in the proximal colon during the final week of treatment for Donor C. These results were confirmed by the branched SCFA levels, where only slight increases were observed towards the end of the treatment in both proximal and distal colon for all donors tested.

TABLE 12

Effect of Gellan Gum treatment on ammonium production (mg/L) in the proximal (PC) and distal colon (DC) reactors for the three different donors (A, B and C), and average weekly ammonium production (mg/L) during control (C1 and C2) and treatment (TR1-TR3) weeks (see also FIGS. 6a-6b).

| Periods | PC | | | DC | | |
| --- | --- | --- | --- | --- | --- | --- |
| | A | B | C | A | B | C |
| C1 | 102 | 110 | 82 | 271 | 280 | 281 |
| C2 | 92 | 85 | 90 | 265 | 285 | 245 |
| TR1 | 72 | 54 | 89 | 240 | 225 | 281 |
| TR2 | 120 | 95 | 92 | 268 | 273 | 291 |
| TR3 | 110 | 114 | 129 | 251 | 299 | 250 |
| CON(ave) | 97 | 98 | 86 | 268 | 283 | 263 |
| TRT(ave) | 101 | 88 | 103 | 253 | 266 | 274 |

TABLE 13

Figure 7A:
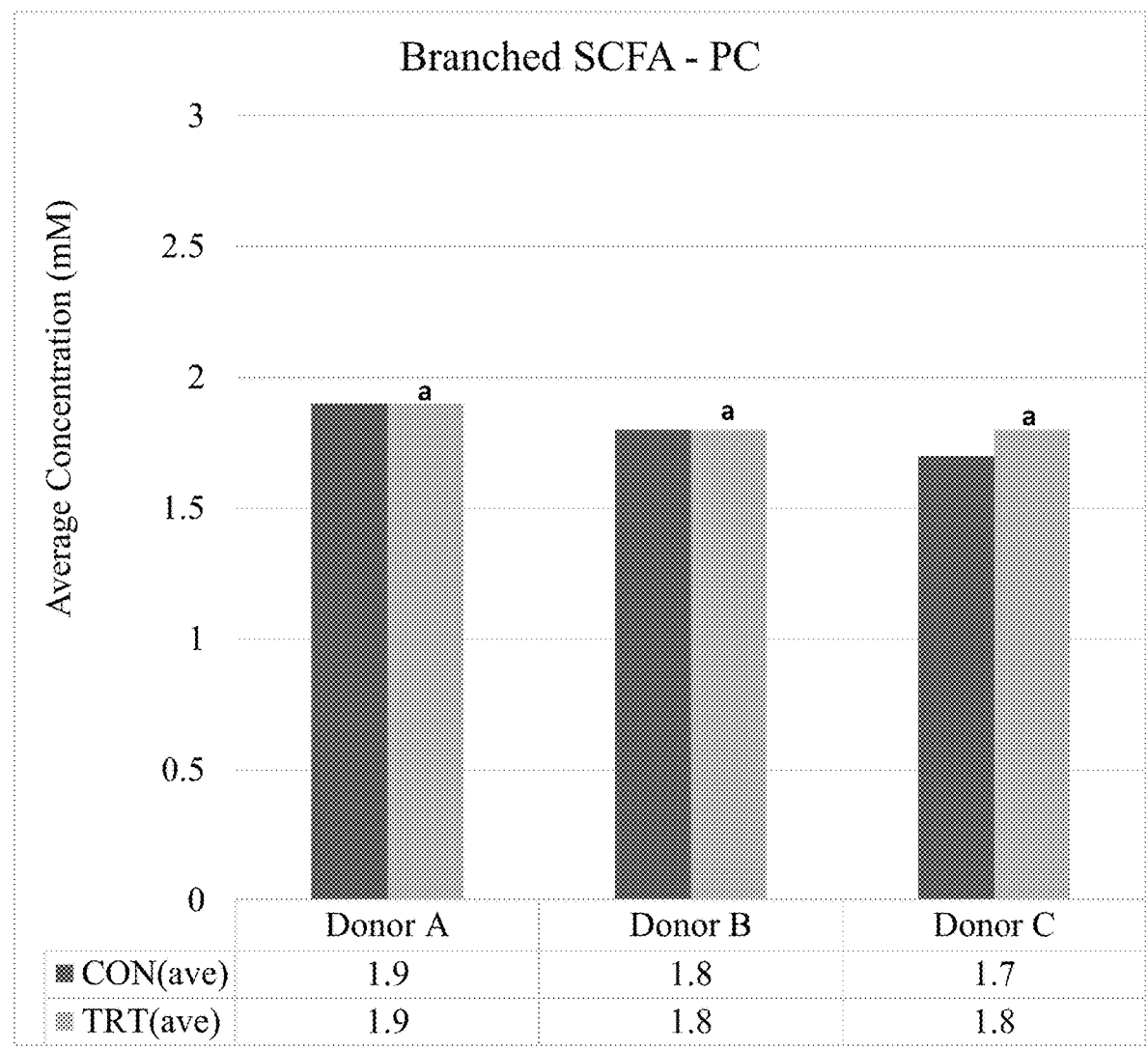
FIG. 7a. Average branched SCFA production (mM) in the proximal colon (PC) reactor over the control (CON(ave), n=6) and treatment (TRT(ave), n=9) period for the three different donors (A, B, and C), where different letters indicate a statistical difference between different treatments; p<0.05.
Figure 7B:
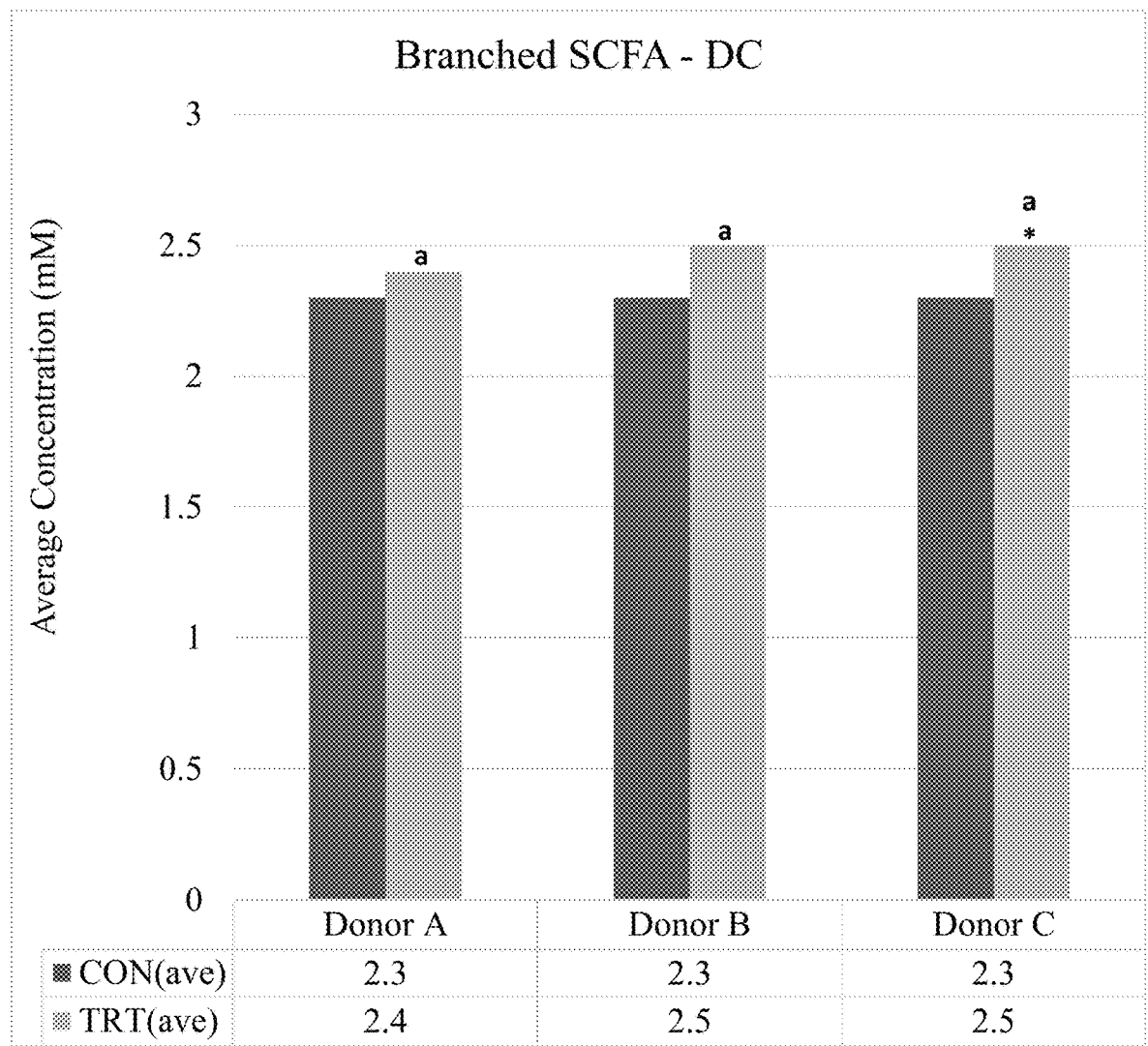
FIG. 7b. Average branched SCFA production (mM) in the distal colon (DC) reactor over the control (CON(ave), n=6) and treatment (TRT(ave), n=9) period for the three different donors (A, B, and C), where * indicates statistically significant differences relative to the preceding period, while different letters indicate a statistical difference between different treatments; p<0.05.

Effect of Gellan Gum treatment on branched SCFA production (mM) in the proximal (PC) and distal colon (DC) reactors for the three different donors (A, B and C), and average weekly branched SCFA production (mM) during control (C1 and C2) and treatment (TR1-TR3) weeks (see also FIGS. 7a-7b).

| Periods | PC | | | DC | | |
| --- | --- | --- | --- | --- | --- | --- |
| | A | B | C | A | B | C |
| C1 | 1.9 | 1.7 | 1.7 | 2.3 | 2.3 | 2.3 |
| C2 | 1.8 | 1.8 | 1.7 | 2.3 | 2.3 | 2.3 |
| TR1 | 1.7 | 1.6 | 1.7 | 2.2 | 2.4 | 2.4 |
| TR2 | 2.1 | 1.8 | 1.7 | 2.4 | 2.4 | 2.5 |
| TR3 | 2.0 | 2.1 | 2.1 | 2.5 | 2.7 | 2.7 |
| CON(ave) | 1.9 | 1.8 | 1.7 | 2.3 | 2.3 | 2.3 |
| TRT(ave) | 1.9 | 1.8 | 1.8 | 2.4 | 2.5 | 2.5 |

G. Analysis of the Microbial Community Composition 16S-targeted Illumina sequencing is a molecular technique which is based on the amplification of the 16S rRNA gene. Because the Illumina sequencing method is PCR-based, microbial sequences are amplified until a saturation level is reached. Therefore, while information on a broad spectrum of (non-predefined) OTUs is obtained (>100 different of the most dominant OTUs), the results are presented as proportional values versus the total amount of sequences within each sample, thus providing semi-quantitative results. The methodology applied herein involves primers that span two hypervariable regions (V3-V4) of the 16S rDNA. Using a paired sequencing approach, sequencing of 2×250 bp results in 424 bp amplicons. Such fragments are taxonomically more useful as compared to smaller fragments that are taxonomically less informative. Besides processing the data at phylum and family level, specific OTUs that changed can be identified, while also the Simpson diversity index can be calculated as a measure of both diversity and evenness. The lowest possible value of the index is 1, representing a community consisting of only one OTU. The highest possible value is the total number of OTUs. The index will approach the maximal value more, when the OTU distribution is more even, while a community that is dominated by a small number of OTUs will result in values closer to 1. The higher the index, the larger the diversity and the larger the evenness.

1. Diversity Index

The reciprocal Simpson Diversity index was calculated as a measure of diversity, both in terms of species richness and evenness. Based on the diversity indices, it followed that during the control period, each of the three SHIME units was colonized by reproducible luminal and mucosal microbial communities, both in the PC and DC. The diversity was higher in the DC, while it was also significantly higher for luminal microbiota versus mucosal microbiota, both in the PC and DC (Table 14).

TABLE 14

Average reciprocal Simpson Diversity Index in the lumen (L) and mucus (M) of the proximal (PC) and distal colon (DC) of three units of the SHIME during the control period (n = 6). Further, also significant differences (p < 0.05) for the reciprocal Simpson Diversity Index between L and M or between PC and DC, as evidenced by the means of their p-value as calculated using a Student's t-test.

|  | L | | M | | PC vs. DC | | L vs. M | |
|---|---|---|---|---|---|---|---|---|
|  | PC | DC | PC | DC | L | M | PC | DC |
| Diversity Index | 4.8 | 11.3 | 3.5 | 7.7 | 0.000 | 0.002 | 0.012 | 0.037 |

Further, with respect to the treatment effects, Gellan Gum increased the diversity of the gut microbiota versus the control for all three donors tested (FIG. 8). Only the diversity of the luminal microbiota in the PC slightly decreased upon Gellan Gum treatment.

2. Phylum Level

Also, the microbiota composition at phylum level pointed out that the three different SHIME units were colonized by reproducible luminal and mucosal microbial communities, both in the proximal and distal colon. As a result, the average values for each of the four environments were calculated while statistical tests were performed to understand the preference of specific phyla for any of the four environments (Table 15).

TABLE 15

Average abundance (%) at microbial phylum level in the lumen (L) and mucus (M) of the proximal (PC) and distal colon (DC) of three units of the SHIME during the control period (n = 6). Further, also significant differences (p < 0.05) for a certain phylum between L and M or between PC and DC are bolded and underlined by means of their p-value as calculated using a Student's t-test.

| | Abundance (%) | | | | p-value | | | |
|---|---|---|---|---|---|---|---|---|
| | L | | M | | PC vs. DC | | L vs. M | |
| Phylum | PC | DC | PC | DC | L | M | PC | DC |
| Actinobacteria | 34% | 2% | 44% | 5% | 0.000 | 0.000 | 0.124 | 0.096 |
| Bacteroidetes | 17% | 47% | 12% | 17% | 0.001 | 0.234 | 0.508 | 0.000 |
| Firmicutes | 44% | 38% | 43% | 40% | 0.107 | 0.579 | 0.913 | 0.586 |
| Lentisphaerae | 0% | 0% | 0% | 0% | 0.060 | 0.080 | >0.05 | 0.063 |
| Proteobacteria | 6% | 3% | 1% | 5% | 0.123 | 0.034 | 0.044 | 0.108 |
| Synergistetes | 0% | 10% | 0% | 32% | 0.000 | 0.000 | 0.537 | 0.000 |
| Verrucomicrobia | 0% | 0% | 0% | 0% | 0.091 | 0.287 | 0.866 | 0.929 |

This revealed a phylum-specific colonization of the lumen versus the mucus layer with: (i) higher levels of Bacteroidetes in the lumen (only significant in DC); (ii) higher levels of Proteobacteria in the lumen (only significant in PC); and (iii) higher levels of Synergistetes in the mucus (only present in DC). Further, following longitudinal differences were observed along the colon: (i) increased Actinobacteria levels in the PC; (ii) increased Bacteroidetes levels in the DC (only significant in the lumen); (iii) presence of Synergistetes in the DC; and (iv) lower Proteobacteria levels in the PC in the mucus layer, whereas an opposite trend was observed in the lumen.

With respect to the treatment, it followed that at the main site of fermentation, i.e., the lumen of the proximal colon (FIG. 9), Gellan Gum strongly increased Actinobacteria levels at the expense of Bacteroidetes and Firmicutes for all three donors tested. Similar observations were noted for the luminal samples of the distal colon (FIG. 9). Additionally, in the distal colon, luminal levels of Synergistetes and Lentisphaerae increased upon treatment with Gellan Gum. In the mucosal compartment (FIG. 9), variability tended to be higher in the samples over time. This might be attributed to the more heterogeneous composition of the biofilm that is formed on top of the mucus layer versus the homogeneous luminal suspension. Similar as in the lumen, mucosal Actinobacteria were enriched in both proximal and distal colon upon treatment with Gellan Gum (except for Donor C in the PC, which showed a very strong stimulation of Synergistetes), however this was not accompanied by a decrease in Bacteroidetes and Firmicutes as in the lumen. Actually, in the mucosal compartment inter-individual differences were observed in Firmicutes levels upon Gellan Gum treatment, i.e., Donor A showed a reduction of Firmicutes levels, whereas an increase was observed for Donors B and C. Finally, treatment with Gellan Gum tended to increase the abundance of Proteobacteria in the mucosal samples of the proximal colon.

3. Family and OTU Level

At family level, the treatment effects of Gellan Gum will mainly be discussed for the main site of fermentation, i.e., the lumen of the proximal colon (FIG. 10). For the other colonic environments (luminal distal colon (FIG. 11), mucosal proximal colon (FIG. 12) and mucosal distal colon (FIG. 13)), many similar observations were made and, therefore, only specific and distinct changes from the main site of fermentation will be discussed.

Gellan Gum strongly increased Bifidobacteriaceae levels for all three donors tested. The information presented in FIGS. 10-11 shows that the Bifidobacteriaceae levels in the lumen of the proximal colon reactors for the two control periods averaged 24.7±5.5%, while the Bifidobacteriaceae levels in the lumen of the proximal colon reactors for the three treatment periods averaged 39.0±8.8%. Further, the information presented in FIGS. 10-11 shows that the Bifidobacteriaceae levels in the lumen of the distal colon reactors for the two control periods averaged 1.85±1.0%, while the Bifidobacteriaceae levels in the lumen of the distal colon reactors for the three treatment periods averaged 8.3±2.3%. At the OTU level, the main changes were found to be attributed to an increase in Bifidobacteriaceae OTU 2 (related to *Bifidobacterium adolescentis*). This strong bifidogenic effect corresponds nicely with the significantly increased acetate levels observed for all three donors upon Gellan Gum treatment.

Treatment with Gellan Gum strongly decreased Bacteroidaceae levels for all three donors tested. The Bacteroidaceae family contains many known propionate producers, which explains the strong decrease in propionate levels that was observed upon Gellan Gum supplementation. Additionally, a decrease in abundance of Veillonellaceae was observed upon treatment with Gellan Gum, which was mainly attributed to a decrease in Veillonellaceae OTU 1 (related to *Megamonas* sp.). As this OTU is a potent propionate producer (while consuming lactate), its decrease likely contributed to the decreased propionate concentrations observed during the treatment period.

Gellan Gum also slightly increased Lachnospiraceae levels throughout the three-week treatment period for the three donors tested, which can be linked to the increased butyrate concentrations observed during the same period. In contrast, in the luminal distal colon Lachnospiraceae levels decreased, whereas other butyrate-producing families increased upon Gellan Gum treatment, i.e., Acidaminococcaceae, Eubacteriaceae and Ruminococcaceae. However, during the final week of treatment, levels of Ruminococcaceae decreased again in the distal colon, while a stimulation of Veillonellaceae was observed during the same week. The latter explains the increased propionate production observed in the distal colon during the final week of treatment and is mainly attributed to a stimulation of the Veillonellaceae OTU 1 (related to *Megamonas* sp.).

Another butyrate-producing family that was solely enriched in the mucosal environment upon treatment with Gellan Gum was the Clostridiaceae family, with a distinct increase of Clostridiaceae OTU 23 (related to *Clostridium butyricum*) in the proximal colon versus Clostridiaceae OTU 17 (related to *Clostridium tertium*) in the distal colon.

Another consistent finding upon Gellan Gum treatment was the increase in several families within the Proteobacteria phylum, such as an increase in Enterobacteriaceae and Xanthomonadaceae. These families are mainly known as they contain several opportunistic pathogenic species, however also many commensals are present within these families, which are known to ferment proteins in the different colonic regions, but mainly in the distal colon. Indeed, similar observations were made for the distal colon region, where several families of the Proteobacteria phylum slightly increased upon treatment with Gellan Gum. These findings can be correlated with the slight increases in branched SCFA levels that were observed towards the end of the treatment period.

Finally, some donor-specific changes were observed upon Gellan Gum treatment in the luminal proximal colon: (i) increased Microbacteriaceae levels for Donors B and C; (ii) increased Micrococcaceae levels for Donors A and C; (iii) increased Enterococcaceae levels, especially observed for Donor C (similar observations were made in the distal colon, which could explain the increased lactate concentration during the final week of treatment that was observed for this donor); and (iv) increased Synergistaceae levels for Donor C. As Synergistaceae are mainly colonizers of the distal colon regions, stronger effects were observed in the luminal distal colon samples, where a strong enrichment of Synergistaceae was observed for all three donors tested.

H. Summary of Example III Results

Acid/base consumption, gas, SCFA, lactate and ammonium production were all very stable within the three different SHIME units during the control period. This indicated that the SHIME model was operated under its most optimal conditions resulting in a stable colon microbiota. This stability is a prerequisite that any effect observed during the treatment truly resulted from the administered test product at a concentration corresponding to an in vivo dose of 2 g/d.

Upon initiating the treatment with Gellan Gum, base consumption increased in the proximal colon (indicating microbial fermentation via SCFA/lactate production) during the final week of treatment for all donors tested. Also, mild immediate increases in base consumption were observed in the distal colon. In terms of gas production, donor-dependent effects were observed, with slightly increased gas production for Donor B, whereas gas production decreased for the other donors upon product addition.

While base consumption and gas production only provide a rough indication of microbial fermentation, SCFA measurements provide more detailed insights in the saccharolytic fermentation processes. This demonstrated that Gellan Gum was mainly fermented in the proximal colon, where it immediately decreased propionate levels, while increasing acetate and butyrate levels gradually. The microbiota of Donor A resulted in the most pronounced increases in both acetate and butyrate levels upon treatment with Gellan Gum. Also in the distal colon, acetate and butyrate levels gradually increased during the course of the treatment, while propionate levels gradually decreased, followed by an increase during the final week of treatment. The largest increase in acetate production was observed for Donor B, whereas Donor A resulted in the largest increase in butyrate levels. Further, lactate concentrations remained overall very stable. In the proximal colon, lactate only increased significantly during the final week of treatment for Donor A. In the distal colon, significantly increased lactate concentrations were observed during the final week of treatment for Donor C.

With respect to markers for proteolytic fermentation, it followed that ammonium levels were unaffected for all donors tested in both the proximal and distal colon, except for a slight increase in the proximal colon during the final week of treatment for Donor C. These results were confirmed by the branched SCFA levels, where only slight increases were observed towards the end of the treatment in both proximal and distal colon for all donors tested.

S-targeted sequencing analysis revealed that the SHIME model maintained a diverse luminal and mucosal microbiota, both in the proximal and distal colon compartment for the three donors tested. Interestingly, the mucosal microbiota was, in consistency with findings for human adults, strongly enriched with families containing well-known butyrate-producing species. Besides this species-specific colonization of the mucus layer, also longitudinal differences in microbial colonization (proximal versus distal colon) were established.

With respect to treatment effects on microbial community composition, it was found that Gellan Gum increased the diversity of the gut microbiota of the three donors tested versus the control period. Further, it followed that at the main site of fermentation (lumen of proximal colon) Gellan Gum strongly increased Actinobacteria levels at the expense of Bacteroidetes and Firmicutes. The increase in Actinobacteria was mainly related to a bloom in Bifidobacteriaceae that nicely corresponded with the increased acetate levels for all three donors tested. Interestingly, the bifidogenic effect upon Gellan Gum supplementation was merely attributed to increases in an OTU related to *Bifidobacterium adolescentis*. The decreases in Bacteroidetes and Firmicutes levels were mainly attributed to decreased Bacteroidaceae and Veillonellaceae levels for all three donors tested. Both families contain several potent propionate producers, correlating to the decreased propionate concentrations observed during the treatment period. Finally, the increasing butyrate production throughout the 3-week treatment period with Gellan Gum was potentially attributed to the increase in butyrate-producing species belonging to several Firmicutes families, such as Lachnospiraceae in the luminal proximal colon, Acidaminococcaceae, Eubacteriaceae and Ruminococcaceae in the luminal distal colon and Clostridiaceae in the mucosal environment.

IV. Example IV. Effect of Gellan Gum on Gut-Wall Functions

A. Introduction

The micro-organisms in the gut represent a biologically active community which lies at the interface of the host with its nutritional environment. As a consequence, they profoundly influence several aspects of the physiology and metabolism of the host. A wide range of microbial structural components and metabolites directly interact with host intestinal cells to influence nutrient uptake and epithelial health. Both microbial associated molecular patterns (MAMPs) and bacterial-derived metabolites (e.g., short-chain fatty acids (SCFA)) activate various signaling pathways such as lymphocyte maturation, epithelial health, neuroendocrine signaling, pattern recognition receptors (PRRs)-mediated and G-protein coupled receptor (GPRs)-mediated signaling. In turn, these signaling pathways will dictate inflammatory tone, energy balance, gut motility and appetite regulation (reviewed in Ha (2014)). Dysregulation of host-microbiome interactions is nowadays recognized to contribute to numerous diseases (Groschwitz (2009)), including metabolic syndrome and obesity, inflammatory bowel diseases (IBD) such as Crohn's disease (CD) and ulcerative colitis (UC), irritable bowel syndrome (IBS), celiac disease, diabetes, allergies, asthma and autoimmune diseases. Common to these disorders is the dysregulation of the intestinal epithelial barrier (more permeable), initiating the pathology (Fasano (2011)). When the intestinal barrier function is disrupted, the trafficking of molecules is no longer under control, so that luminal contents may enter the lamina propria and activate the immune system, thereby leading to uncontrolled immune responses (a process known as 'leaky gut'). The intestinal epithelial barrier is formed by intercellular tight junctions, a complex protein-protein network that mechanically links adjacent cells and seals the intercellular space. Therefore, the intestinal epithelial barrier controls the equilibrium between immune tolerance and immune activation, and so it has a prominent role in 'leaky gut' pathogenesis. An improper functioning or regulation of these tight junctions seems to be responsible for larger intercellular spaces allowing luminal element passage through the barrier, with a consecutive local and systemic inflammation.

B. The Caco-2/THP1 Co-Culture In Vitro Model

Figure 14:
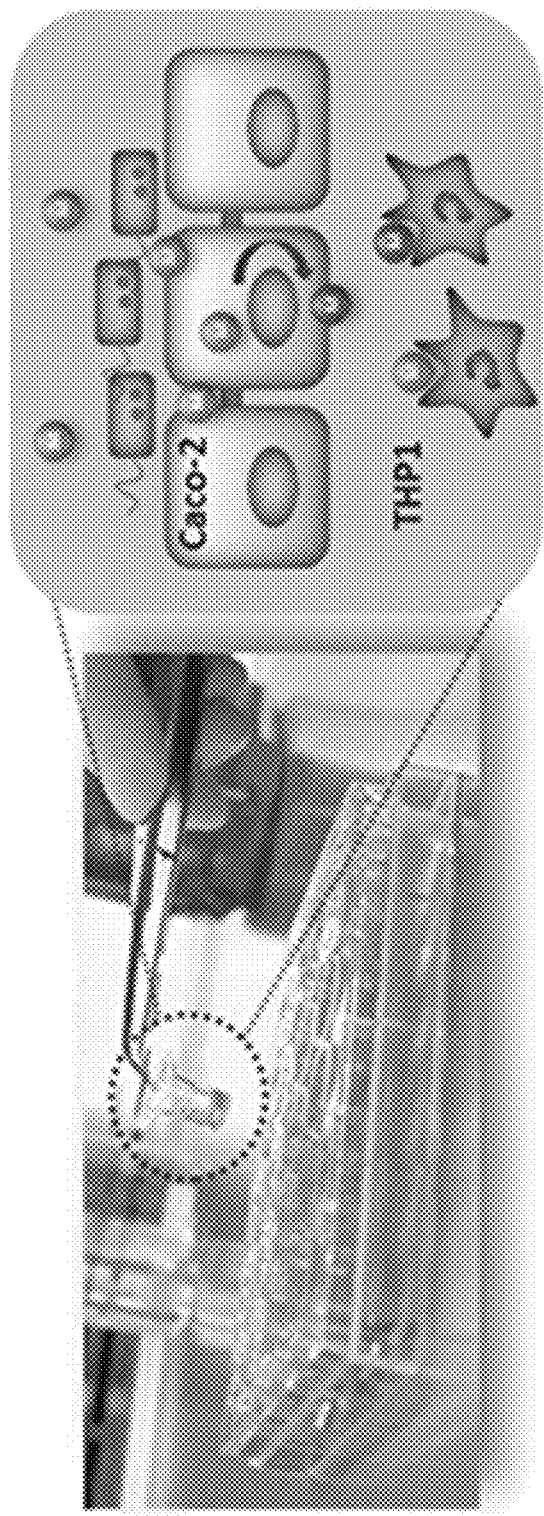
FIG. 14. Schematic representation of the co-culture of Caco-2 and THP1 cells. Caco-2 cells are seeded on a semi-permeable membrane that is placed on top of wells that are seeded with THP1 cells. This creates an apical (AP) and a basolateral (BL) compartment. The monolayer of Caco-2 cells creates a barrier to macro-molecules and allows the passage by passive transport of small molecules between the intercellular space and the active transport of micro- and macro-molecules across the cell membranes. The co-culture of both cell types allows the indirect cross-talk between the luminal content that is in contact with the Caco-2 cells and the peri-intestinal content in contact with the immune cells (THP1). In addition, metabolites used/transformed by the epithelial cells may modulate the immune cell response, and vice-versa.

To mimic the interface between host and gut microbiome, several in vitro models have been developed in the past years which include the use of intestinal epithelial-like cells and immune cells of human origin. The model used herein was a co-culture model of intestinal epithelial-like cells (Caco-2 cells) and human monocytes/macrophages (THP1 cells). (See FIG. 14; see also Possemiers (2013) Satsu (2006).) Caco-2, when seeded on suitable supports, spontaneously differentiate into mature enterocyte-like cells, characterized by polarization, presence of villi, formation of domes, presence of tight junctions and vectorial transport and expression of apical brush-border enzymes (reviewed by Sambuy (2005)). THP1 monocytes, isolated from a human patient with acute leukemia, differentiate into macrophage-like cells upon phorbol 12-myristate 13-acetate (PMA) treatment. PMA-activated THP1 cells acquire morphological features characteristic of macrophages, are able to adhere to the support, develop lamellipodia necessary for migration and phagocytosis and become primed for toll-like receptor (TLR) responses. (Dumrese (2009).) Tight junction proteins keep adjacent epithelial cells together, thereby forming a virtually impermeable barrier to macromolecules. The 'tightness' of these junctions can be measured as transepithelial electrical resistance (TEER), with a high TEER corresponding to a tighter barrier. Upon loss of barrier function, the paracellular transport (in-between cells) of fluids increases, which can be measured as a reduction of the TEER. When Caco-2 cells are placed on top of PMA-activated THP1 cells, which secrete cytokines into the supernatant, their monolayer becomes disrupted. This is possibly due to cytokine-mediated disruption of tight junctions and can be measured as a decrease in TEER.

Figure 15:
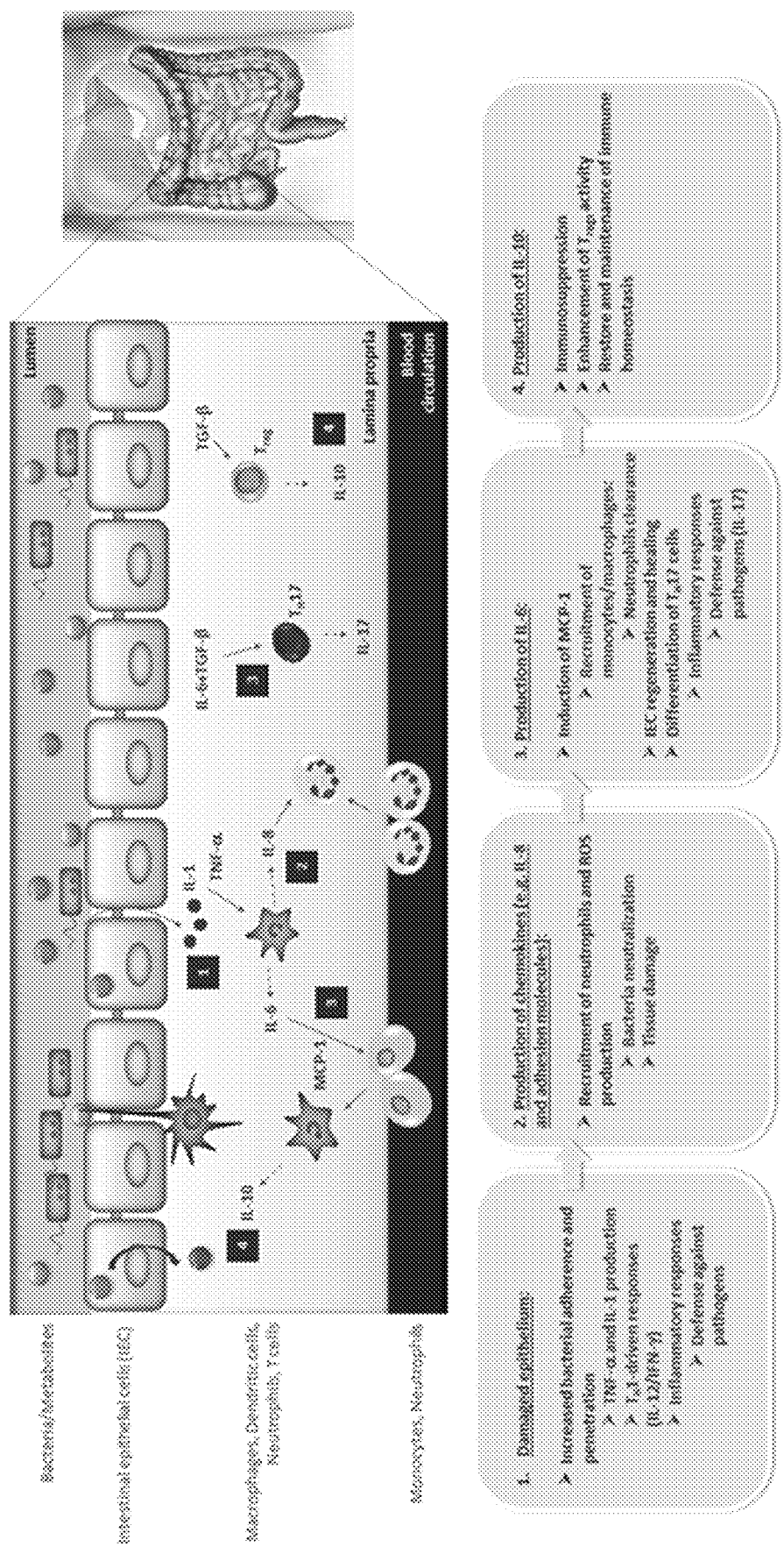
FIG. 15. Signaling cascade activated upon damage of the intestinal epithelial barrier, leading to luminal content breaching the intestinal cell wall. IFN-$\gamma$: interferon gamma; IL: interleukins; MCP-1: monocyte chemoattractant protein 1; ROS: reactive oxygen species; TGF-$\beta$: transforming growth factor beta; $T_H$: helper T cells; TNF-$\alpha$: tumor necrosis factor alpha; $T_{reg}$: regulatory T cells.

Within the gut, chemical, mechanical or pathogen-triggered barrier disruption may lead to the influx of bacteria from the lumen into the lamina propria (FIG. 15). This will activate the immune system, which will switch from a physiological 'tolerogenic' inflammation into a detrimental pathological inflammation. An inflammatory signaling cascade will be initiated with the production of alarm molecules such as pro-inflammatory cytokines (e.g., tumor necrosis factor (TNF)-$\alpha$ and interleukin (IL)-1$\beta$). TNF-$\alpha$, together with interferon (IFN)-$\gamma$, is produced by leukocytes and CD4$^+$ $T_H$ (helper) type 1 cells, critical cellular defenders against invading microorganisms. These pro-inflammatory cytokines will induce the production of chemokines (e.g., IL-8 and chemokine (C-X-C motif) ligand (CXCL)-10) and adhesion molecules), necessary for neutrophil recruitment and reactive oxygen species (ROS) production. ROS production is necessary to kill the invading bacteria and to seal breaches in the epithelial wall. However, they may also cause tissue disruption and inflammation, leading to the need to resolve the inflammation by the production of anti-inflammatory cytokines, like IL-6 and IL-10.

IL-6 possesses both pro- and anti-inflammatory properties. Scheller (2011). IL-6 leads to monocyte/macrophage recruitment via activation of monocyte chemoattractant protein (MCP)-1, which promote the clearance of neutrophils. IL-6 is also able to inhibit the production of pro-inflammatory cytokines such as IL-1. Moreover, IL-6 has a positive effect on the regeneration of the intestinal epithelium and wound healing. Dann (2008). On the other hand, IL-6, together with transforming growth factor (TGF)-$\beta$, induces the differentiation of an important subset of CD4$^+$ T cells— $T_H17$ cells—that have a key role in host defense against extracellular microbes in mucosal tissues.

IL-10 is an anti-inflammatory cytokine, able to suppress several innate and adaptive immune cell types. Also, IL-10 induces the activation of anti-inflammatory molecules and enhances regulatory T cell ($T_{reg}$) function, which will restore immune homeostasis. Lyer (2012). When these switch-off mechanisms are impaired and immune homeostasis cannot be restored, gut pathology can occur, which may result in chronic inflammation (as seen for example in IBD, which is characterized by an over-activation of $T_H1$-mediated responses, namely by overproduction of TNF-$\alpha$).

Figure 16:
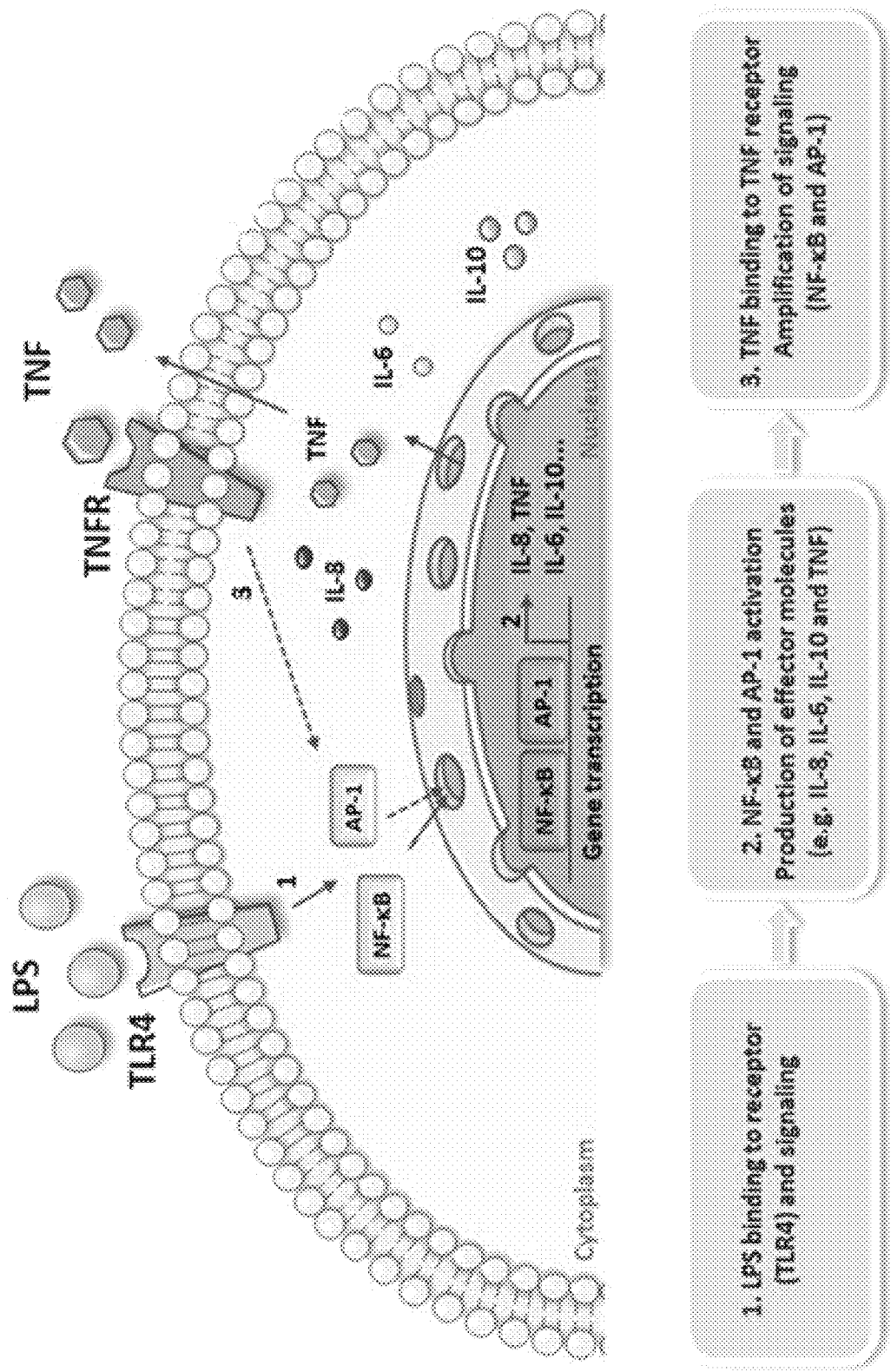
FIG. 16. LPS and TNF-$\alpha$ signaling pathways leading to inflammation. AP-1: activator protein 1 (transcription factor); IL: interleukins, LPS: lipopolysaccharides; NF-$\kappa$B: nuclear factor kappa B (transcription factor); TLR4: toll-like receptor 4 (LPS receptor); TNF-$\alpha$: tumor necrosis factor alpha; TNFR: TNF-$\alpha$ receptor.

In terms of inflammation, TNF-$\alpha$ is one of the most potent and dangerous cytokines produced by the immune system as it exerts pleiotropic effects and is able to amplify inflammatory signaling (FIG. 16). When not counteracted, TNF-$\alpha$ can lead to chronic inflammation and even death in cases of acute inflammation. For this reason, anti-TNF-$\alpha$ therapy is widely used in chronic inflammatory conditions, including IBD and rheumatoid arthritis.

The Caco-2/THP-1 co-culture model shows some features also observed in IBD patients, and is, therefore, suggested to be an 'IBD-like' model, which can be used for testing the effect of substances that both can protect the intestinal epithelial barrier integrity and reduce inflammation. Satsu (2006). As said, in this model, protection of intestinal barrier function is measured as an increase in TEER, while anti-inflammatory potential is determined via analysis of the cytokine profile (increase in anti-inflammatory cytokines and decrease in pro-inflammatory cytokines).

The colonic suspensions collected from the SHIME are brought in contact with the apical side of the co-cultures (Caco-2 cells). The effects observed on the basolateral chamber (where the THP1 cells reside) are then mediated indirectly by signals produced by the Caco-2 cells and/or by the transport of micro- and macro-molecules. The unique aspect of this approach resides in the fact that it allows evaluating the effect induced by the product and the fermentation-derived metabolites produced by the gut microbiota during the digestive steps (so, not only by the pure product). Daguet (2016).

C. Aim of the Study

The aim of this part of the study was to investigate the potential positive effects of the product Gellan Gum and their metabolites on gut-wall functions, in three different donors. Bacteria closely interact with the gut-wall, so modulation of the microbial activity is likely to affect gut-wall functions. This will be assessed by evaluating intestinal epithelial permeability and specific immune markers in vitro.

D. Materials and Methods

Samples collected from the SHIME experiment described above were used to evaluate in vitro the effect of the fermented products on intestinal epithelial barrier function and immune markers. These include samples from the proximal and distal colon reactors of three different donors, collected at the end of the control and treatment periods.

E. Caco-2 Cells

The co-culture experiment was performed as previously described. Daguet (2016). Briefly, Caco-2 cells (HTB-37; American Type Culture Collection) were seeded in 24-well semi-permeable inserts. Caco-2 monolayers were cultured for 14 to 21 days, with three medium changes/week, until a functional cell monolayer with a transepithelial electrical resistance (TEER) was obtained. Cells were maintained in Dulbecco's Modified Eagle Medium (DMEM) containing glucose and glutamine and supplemented with HEPES and 20% (v/v) heat-inactivated (H1) fetal bovine serum (FBS).

F. THP1-Blue™ Cells

THP1-Blue™ (InvivoGen) cells were maintained in Roswell Park Memorial Institute (RPMI) 1640 medium containing glucose and glutamine, supplemented with HEPES, sodium pyruvate and 10% (v/v) H1-FBS. THP1-Blue™ are THP1 human monocytes stably transfected with a reporter construct expressing a secreted alkaline phosphatase (SEAP) gene under the control of a promoter inducible by the transcription factor nuclear factor kappa B (NF-κB). Upon TLR activation (e.g., by lipopolysaccharide (LPS); isolated from Gram-negative bacteria), NF-κB becomes activated and induces the expression and secretion of SEAP. SEAP activity can then be measured in the supernatants by using the QUANTI-Blue reagent (InvivoGen). THP1-Blue™ cells were seeded in 24-well plates and treated with PMA that induces the differentiation of the cells into macrophage-like cells, which are able to adhere and are primed for TLR signaling.

G. Caco-2/THP1-Blue™ Co-Culture

Before setting up the co-culture, the TEER of the Caco-2 monolayers was measured (=0 h time point). The TEER of an empty insert was subtracted from all readings to account for the residual electrical resistance of an insert. Then, the Caco-2-bearing inserts were placed on top of the PMA-differentiated THP1-Blue™ cells for further experiments, as previously described. Possemiers (2013) and Lyer (2012).

Briefly, the apical compartment (containing the Caco-2 cells) was filled with sterile-filtered (0.22 μm) colonic SHIME suspensions or with different concentrations of live bacteria. Cells were also treated apically with sodium butyrate (NaB) (Sigma-Aldrich) as positive control. The basolateral compartment (containing the THP1-Blue™ cells) was filled with Caco-2 complete medium. Cells were also exposed to Caco-2 complete medium in both chambers as control. Cells were treated for 24 h, after which the TEER was measured (=24 h time point). After subtracting the TEER of the empty insert, all 24 h values were normalized to its own 0 h value (to account for the differences in initial TEER of the different inserts) and are presented as percentage of initial value. Then, the basolateral supernatant was discarded, and cells were stimulated at the basolateral side with Caco-2 complete medium containing ultrapure LPS (Escherichia coli K12, InvivoGen). Cells were also stimulated at the basolateral side with LPS in combination with hydrocortisone (HC) (Sigma-Aldrich) and medium without LPS (LPS−) as controls. After LPS stimulation, the basolateral supernatants were collected for cytokine measurement (human IL-1β, IL-6, IL-8, IL-10, TNF-α, CXCL10 and MCP-1 by Luminex® multiplex (Affymetrix-eBioscience)) and for NF-κB activity, according to the manufacturers' instructions. Cells were incubated at 37° C. in a humidified atmosphere of air/$CO_2$ (95:5, v/v).

H. Statistics

The experimental controls are presented first in separate plots; these relate to the complete media control (CM or LPS−), the lipopolysaccharide (LPS+)-treated cells and the sodium butyrate (NaB) and hydrocortisone (HC) controls. Concerning the TEER, the conditions CM and NaB are compared and statistical significance was calculated by using unpaired, two-tailed Student's t-test. For the immune markers (cytokines/chemokines and NF-κB activity), all conditions (LPS−, LPS+HC and LPS+NaB) are compared to LPS+. Statistical significance was calculated by using one-way ANOVA with Dunnett's multiple comparisons test against LPS+. (*), (), (*) and (****) represent $p<0.05$, $p<0.01$, $p<0.001$ and $p<0.0001$, respectively.

The results concerning the SHIME samples are presented separately. The control (C) and treatment (T) samples, presented for both colon reactors (proximal (PC) and distal (DC) colon) were taken as biological triplicates in the SHIME experiment. Results for the three different donors separately as also the mean of the three donors are shown. To evaluate the differences in TEER, NF-κB activation and cytokine production between each treatment sample and the control, an ordinary one-way ANOVA with Tukey's multiple comparisons test was performed (significance is depicted with an asterisk (*)). (*), (), (*) and (****) represent $p<0.05$, $p<0.01$, $p<0.001$ and $p<0.0001$, respectively. All statistics were performed using GraphPad Prism™ software version 7.02 for Windows (GraphPad Software, San Diego, Calif., USA).

I. Control Results

1. Transepithelial Electrical Resistance (TEER)

Figure 17:
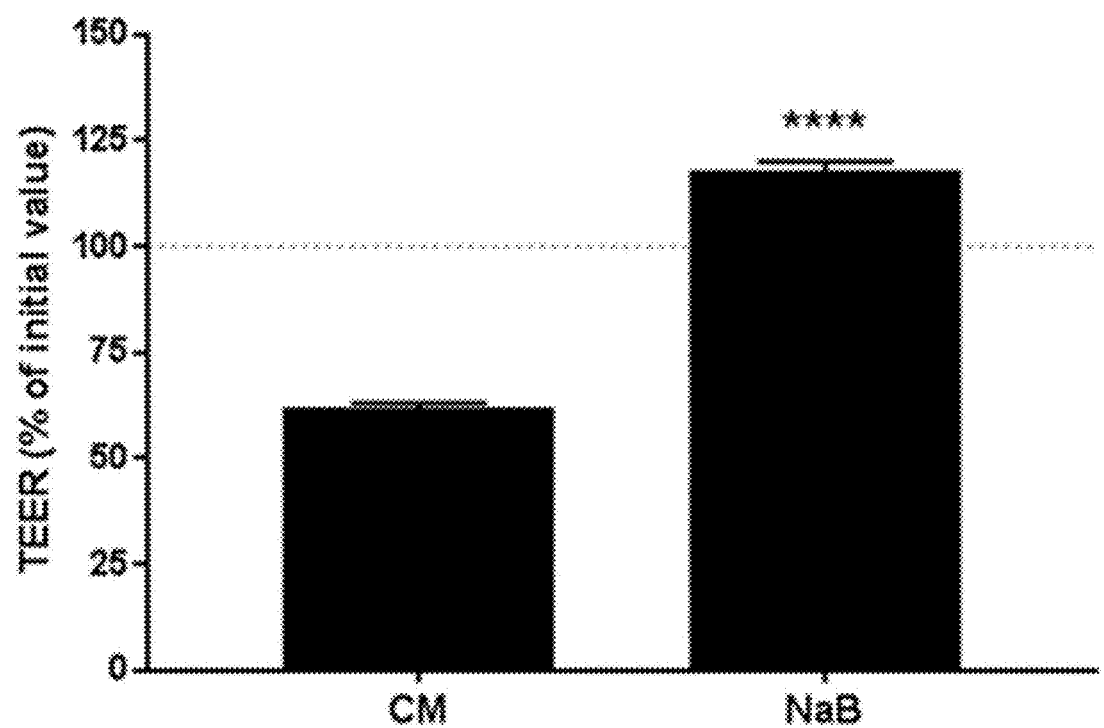
FIG. 17. Transepithelial electrical resistance (TEER) on the control tests CM and NaB. The TEER was measured 24 h after treatment of the Caco-2/THP1-Blue™ co-cultures and each 24 h value was normalized to its corresponding 0 h value and is shown as percentage of initial value. The dotted line represents 100% (initial value). Data are plotted as mean±SEM. (*) represents statistical significant difference between CM and NaB. (****)=$p<0.0001$. CM: complete medium; NaB: sodium butyrate.

After 24 h co-culture incubation, the complete medium (CM) control showed a nearly 40% decrease in TEER due to the damage induced by PMA-activated THP1 cells on Caco-2 cells (FIG. 17). As expected, sodium butyrate (NaB; positive control) was able to protect Caco-2 cells from this damage and to maintain the TEER of the monolayer. Peng (2007). Note that LPS is only added after the TEER has been measured at 24 h. However, preliminary experiments had shown that the dose of LPS used does not significantly affect the barrier integrity of the Caco-2 cells.

2. Immune Markers

Figure 18:
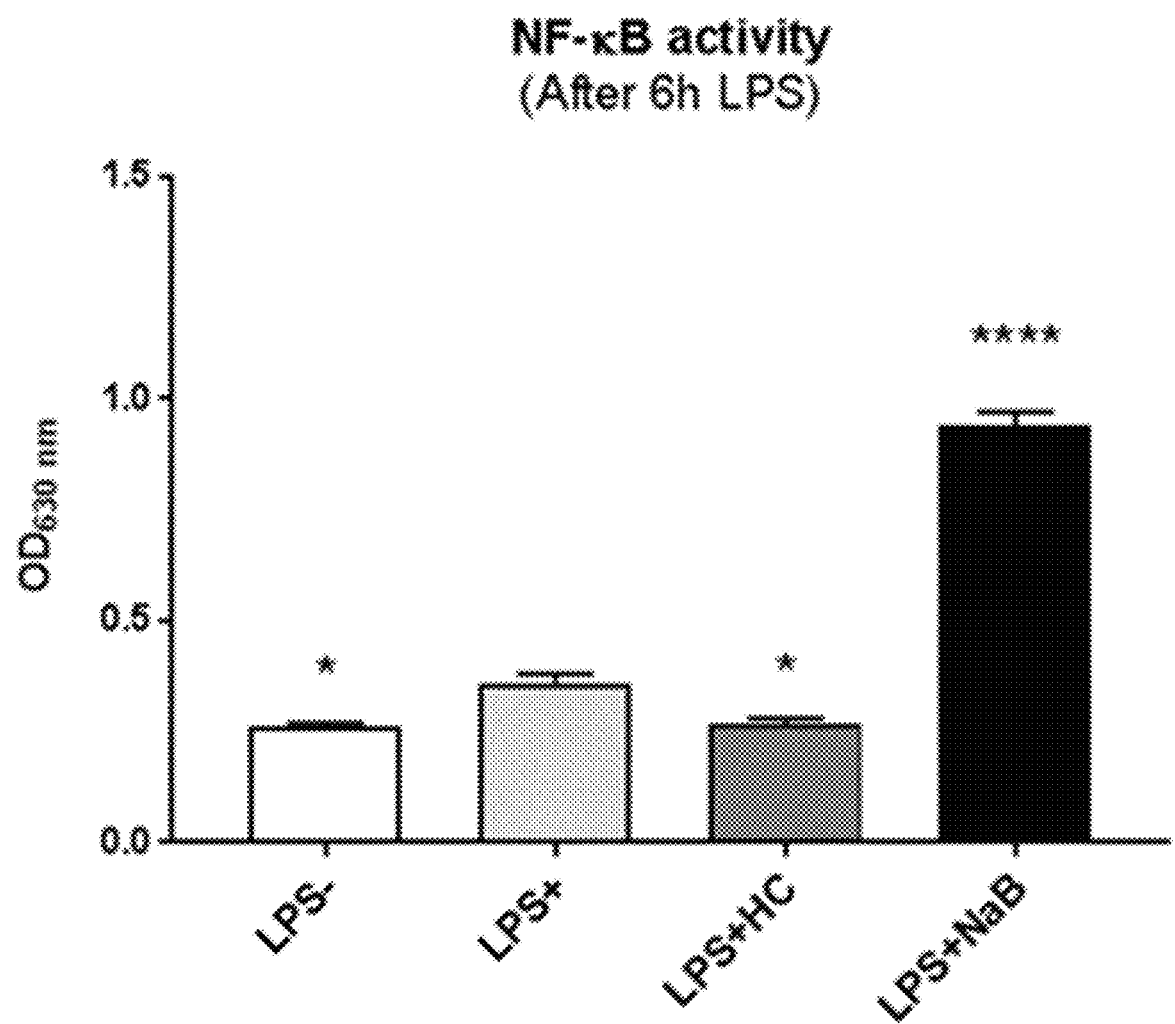
FIG. 18. Basolateral NF-$\kappa$B activity of THP1-Blue™ cells in the control tests LPS−, LPS+, LPS+HC and LPS+NaB. NF-$\kappa$B activity was measured after 6 h of LPS treatment of the Caco-2/THP1-Blue™ co-cultures at the basolateral side after pre-treatment for 24 h with NaB or complete medium at the apical side. Data are plotted as mean±SEM. (*) represents statistical significant differences compared to LPS+. (*)=$p<0.05$; (****)=$p<0.0001$. LPS−: cells treated with complete medium (no LPS); LPS+: LPS-treated cells; HC: hydrocortisone; NaB: sodium butyrate.
Figure 20:
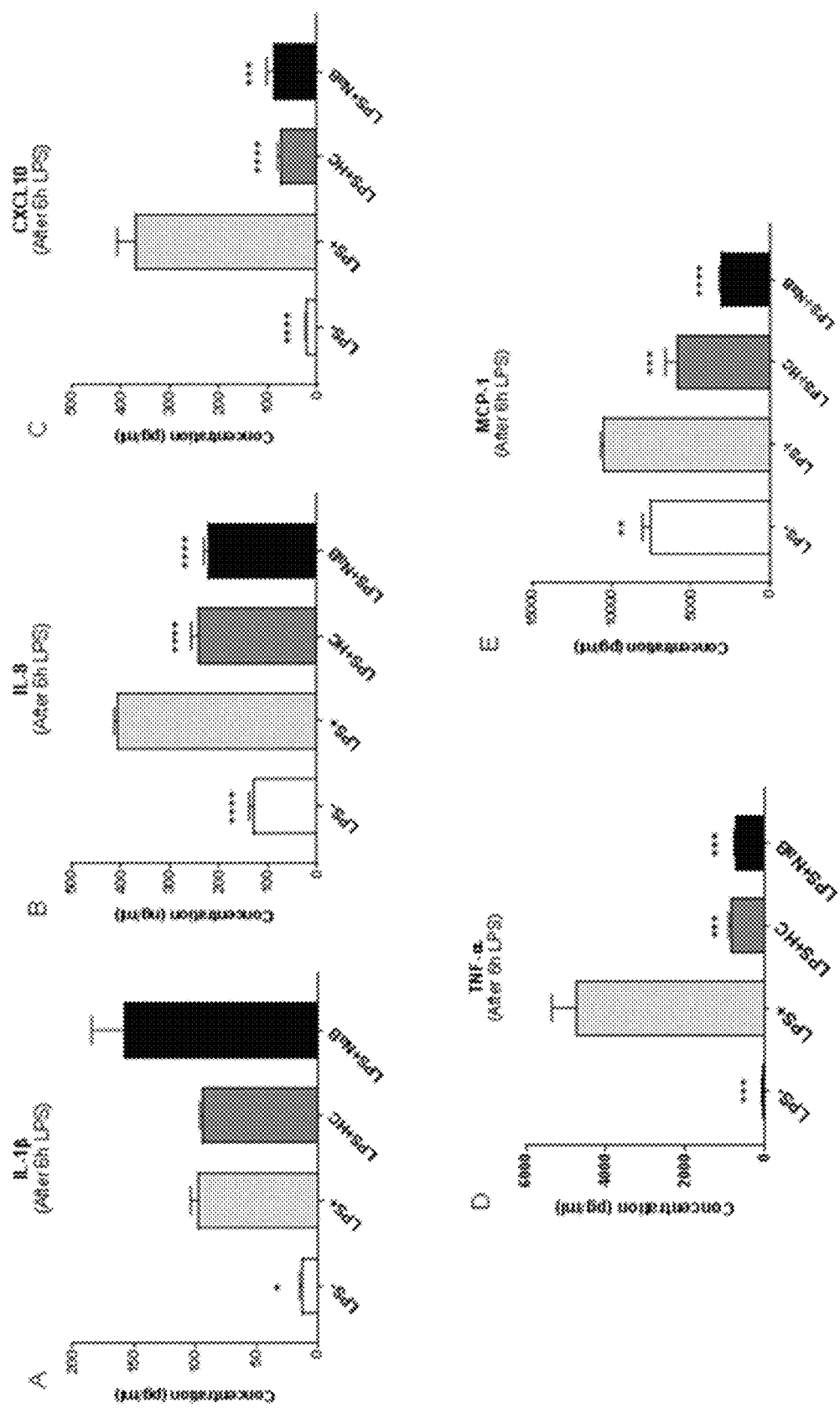
FIG. 20. Basolateral secretion of IL-1$\beta$ (A), IL-8 (B), CXCL10 (C), TNF-$\alpha$ (D) and MCP-1 (E) in the control tests LPS−, LPS+, LPS+HC and LPS+NaB. Cytokines were measured after 6 h of LPS treatment of the Caco-2/THP1-Blue™ co-cultures at the basolateral side after pretreatment for 24 h with NaB or complete medium at the apical side. Data are plotted as mean±SEM. (*) represents statistical significant differences compared to LPS+. (*)=p<0.05; ()=p<0.01; (*)=p<0.001; (****)=p<0.0001. LPS−: cells treated with complete medium (no LPS); LPS+: LPS-treated cells; HC: hydrocortisone; NaB: sodium butyrate.

The results obtained for the different immune markers can be seen in FIG. 18, FIG. 19 and FIG. 20. As expected, LPS was able to increase NF-κB activation (FIG. 18) as well as secretion of all cytokines tested (IL-6 and IL-10 (FIG. 19) and IL-β, IL-8, CXCL10, TNF-α and MCP-1 (FIG. 20)). Also, hydrocortisone (HC), being a corticosteroid, acts as a broad immunosuppressant by dampening LPS-induced cytokines and chemokines (FIG. 19 and FIG. 20) and by inhibiting LPS-induced transcriptional activity of NF-κB (FIG. 18). In contrast, sodium butyrate (NaB) showed marker-dependent effect. NaB increased the transcriptional activity of NF-κB (FIG. 18), an effect which is possibly mediated by the attenuation of histone deacetylase (HDAC) inhibitory activities on non-histone proteins such as NF-κB. Glozak (2005) and Vinolo (2011). In addition, NaB showed clear selective post-transcriptional inhibitory activities on some immune mediators. More specific, NaB selectively increased LPS-induced IL-6 and IL-10 secretion (involved in immune homeostasis) (FIG. 19), while it selectively inhibited LPS-induced TNF-α (pro-inflammatory cytokines) and IL-8, CXCL10 and MCP-1 (chemokines involved in recruitment of immune cells) (FIG. 20).

In conclusion, all controls behaved as expected in this experiment and the results obtained for the SHIME samples are presented below. Note that in this experiment, HC and NaB unexpectedly did not reduce the LPS-induced IL-1β expression.

J. Results of SHIME Samples

1. Transepithelial electrical resistance (TEER)

SHIME samples collected during the last weeks of control and treatment from all colon reactors were diluted (1:5, v/v) in Caco-2 complete medium after filtration (0.22 μm) and were given apically to the co-cultures for 24 h.

Figure 21:
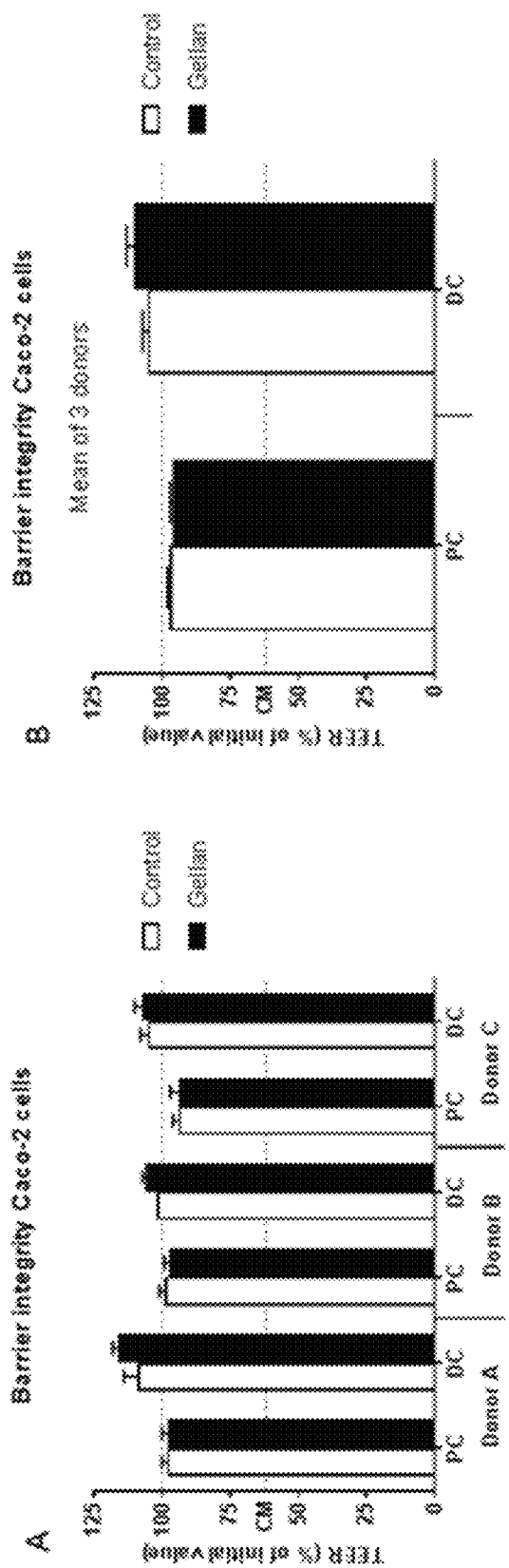
FIG. 21. Effect of the SHIME samples on transepithelial electrical resistance (TEER) of the Caco-2/THP1-Blue™ co-cultures. Results are shown for the three different donors separately (A) and as the mean of the three donors (B). TEER was measured 24 h after treatment of the co-cultures and each 24 h value was normalized to its corresponding 0 h value and is shown as percentage of initial value. The grey dotted line represents 100% (initial value). The dotted line corresponds to the experimental control CM (complete medium). Data are plotted as mean±SEM. No significant differences were found between the control and treatment of the three different donors. PC: proximal colon samples; DC: distal colon samples.

As compared to the complete medium (CM) control where the TEER decreased approximately 40% (FIG. 17), all control and treatment samples collected from the SHIME, were able to maintain the TEER nearly at the initial value (FIG. 21). A mild, although not significant, increase in TEER was observed for Gellan Gum treatment in the distal colon samples of all three donors, compared to the control. Given the fact that this increase was consistently observed for all three donors, it can be concluded that fermentation of Gellan Gum has potential to improve the intestinal epithelial barrier function in the in vitro model used.

2. Immune Markers

After 24 h of apical pre-treatment of the Caco-2/THP-1-Blue™ co-cultures with SHIME samples, the basolateral supernatant was discarded, and the cells were stimulated with LPS. After 6 h stimulation, the basolateral supernatant was collected to measure cytokines and chemokines secreted in the medium and to determine NF-κB activity.

Figure 22:
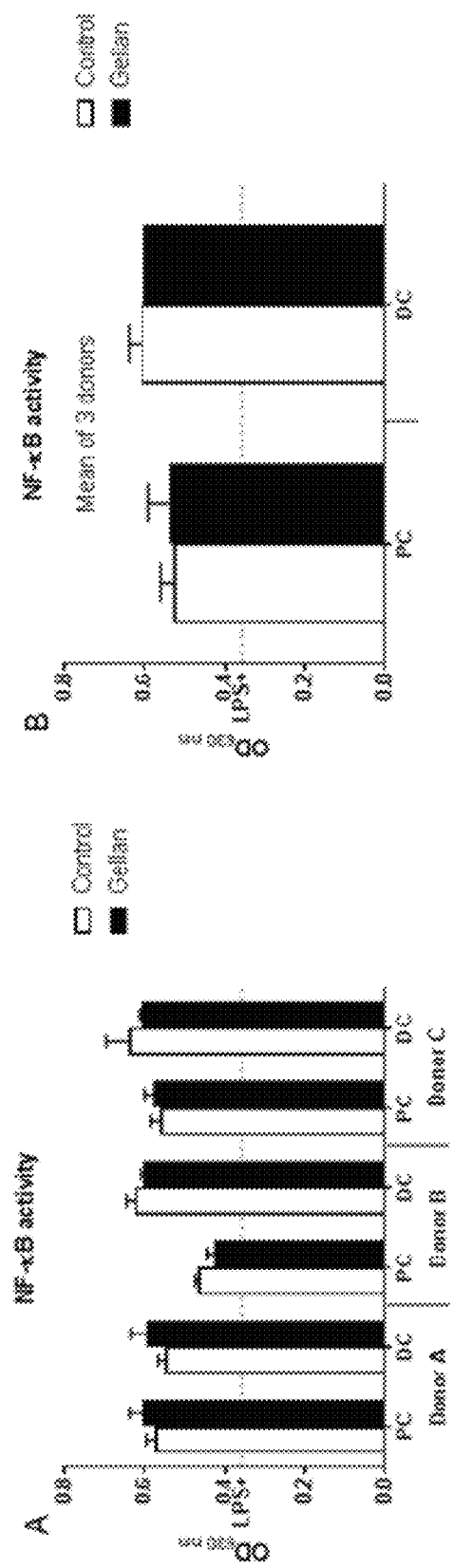
FIG. 22. Effect of SHIME samples on NF-κB activity of THP-1-Blue™ cells. Results are shown for the three different donors separately (A) and as the mean of the three donors (B). NF-κB activity levels were measured 6 h after LPS treatment on the basolateral side of the Caco-2/THP-1-Blue™ co-cultures after pretreatment of the apical side for 24 h with SHIME samples. The dotted line corresponds to the experimental control LPS+. Data are plotted as mean±SEM. No significant differences were found between the control and treatment of the three different donors. PC: proximal colon samples; DC: distal colon samples.

When compared to the LPS+ control (red dotted line), all SHIME samples increased LPS-induced NF-κB transcriptional activity (FIG. 22). However, there was no statistically significant difference between the control samples and the treatment samples. Therefore, the increase in NF-κB activity rather reflects the effect of the SHIME suspension on the cells and not of the test compound.

Figure 23:
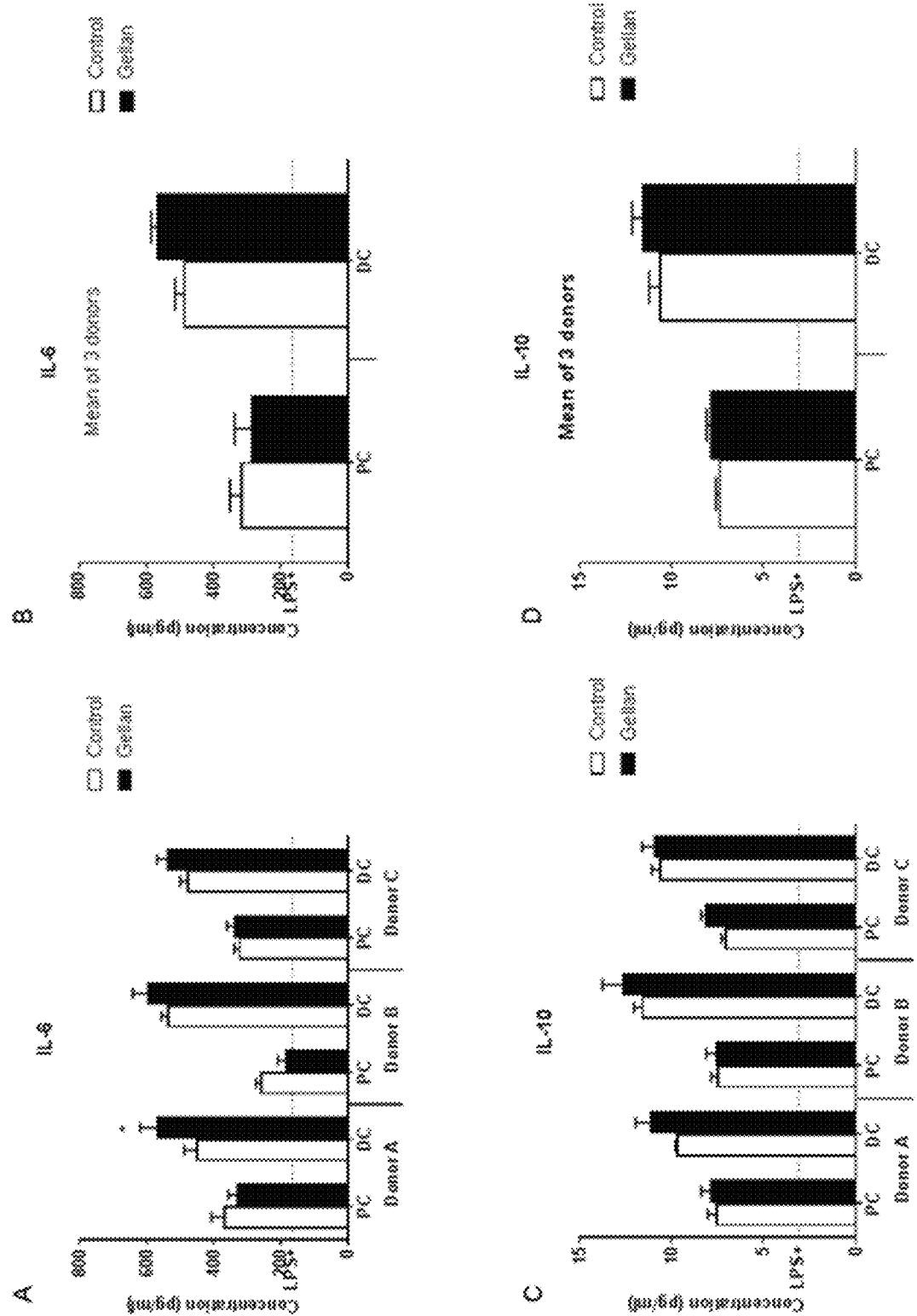
FIG. 23. Effect of SHIME samples on secretion of IL-6 (A and B) and IL-10 (C and D). Results are shown for the three different donors separately (A and C) and as the mean of the three donors (B and D). Cytokine levels were measured 6 h after LPS treatment on the basolateral side of the Caco-2/THP-1-Blue™ co-cultures after pretreatment of the apical side for 24 h with SHIME samples. The dotted line corresponds to the experimental control LPS+. Data are plotted as mean±SEM. (*) represents statistically significant differences compared to the control. (*)=p<0.05. PC: proximal colon samples; DC: distal colon samples.

Similar to the results obtained for the NF-κB activity, all SHIME samples increased the LPS-induced IL-6 and IL-10 levels, compared to the LPS+ control (FIG. 23). Although not significant, a slight increase in IL-6 and IL-10 levels, compared to the control, was consistently observed for all donors in the distal colon samples. This was only statistically significantly different for IL-6 levels in Donor A. This increase in IL-6 and IL-10 levels was also seen when the mean of the three donors was analyzed. Interestingly, when applying a paired t-test over all samples of proximal and distal colon, significantly increased IL-10 levels ($p<0.05$) were observed over the three donors tested.

Figure 24:
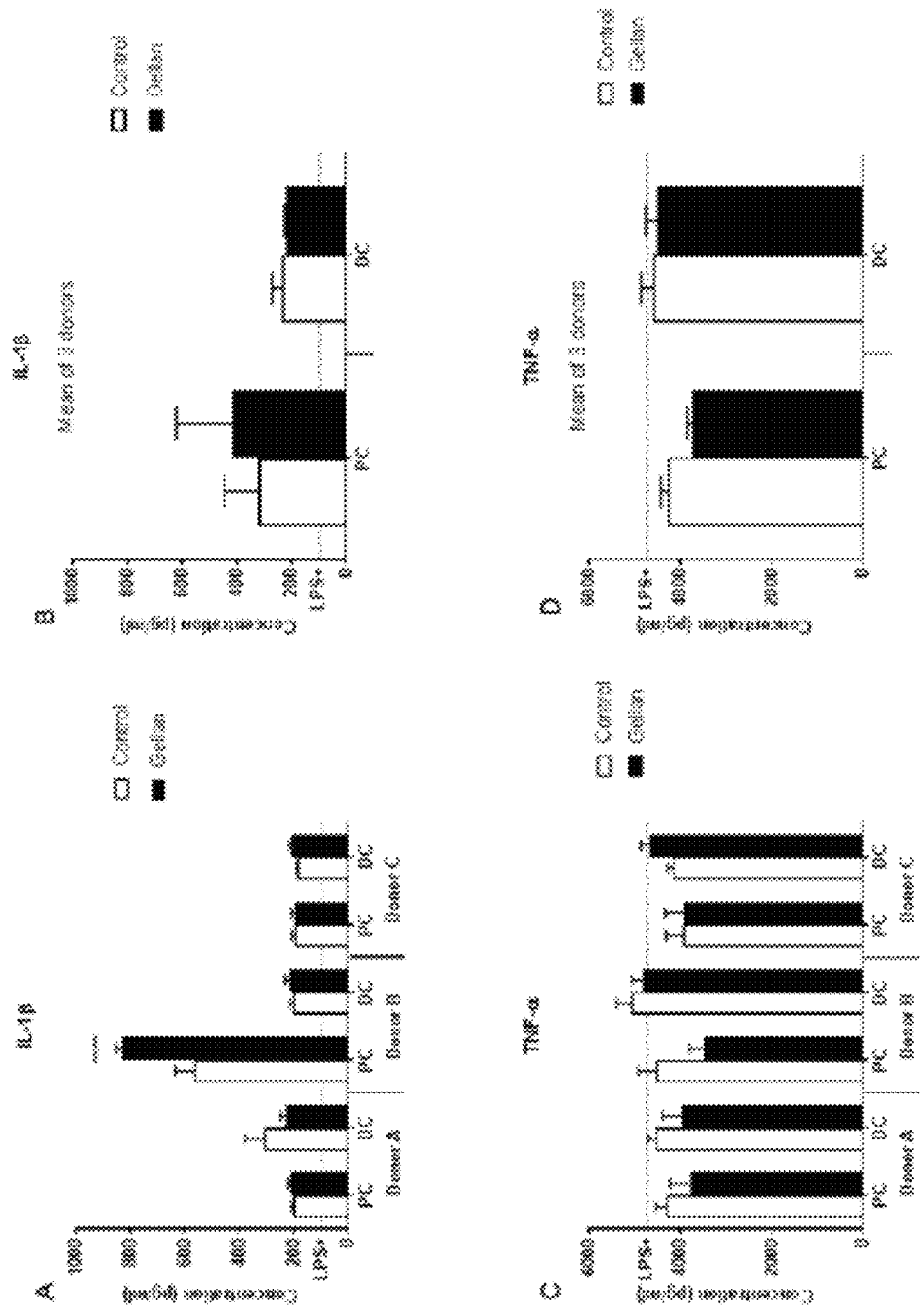
FIG. 24. Effect of SHIME samples on secretion of IL-1β (A+B) and TNF-α (C+D). Results are shown for the three different donors separately (A-C) and as the mean of the three donors (B-D). Cytokine levels were measured 6 h after LPS treatment on the basolateral side of the Caco-2/THP-1-Blue™ co-cultures after pretreatment of the apical side for 24 h with SHIME samples. The dotted line corresponds to the experiment control LPS+. Data are plotted as mean±SEM. (*) represents statistically significant differences compared to the control. (****)=p<0.0001 PC: proximal colon samples; DC: distal colon samples.

The results obtained for IL-1β and TNF-α are shown in FIG. 24. All SHIME samples clearly increased IL-1β secretion compared to the LPS+ control (red dotted line), however, there were no differences observed in IL-1β levels between control and treatment, except for Donor B, where a significant increase of IL-1β levels was observed after treatment for the proximal colon reactor. No significant differences in IL-1β secretion were seen between control and treatment when analyzing the mean of the three donors.

Compared to their controls, LPS-induced TNF-α levels were decreased in the proximal and distal colon samples for Donor A and Donor B, but not for Donor C. When observing the mean of the three donors, a slight decrease in TNF-α secretion was seen in the proximal colon samples compared to the controls, but no statically significant differences were observed.

Figure 25:
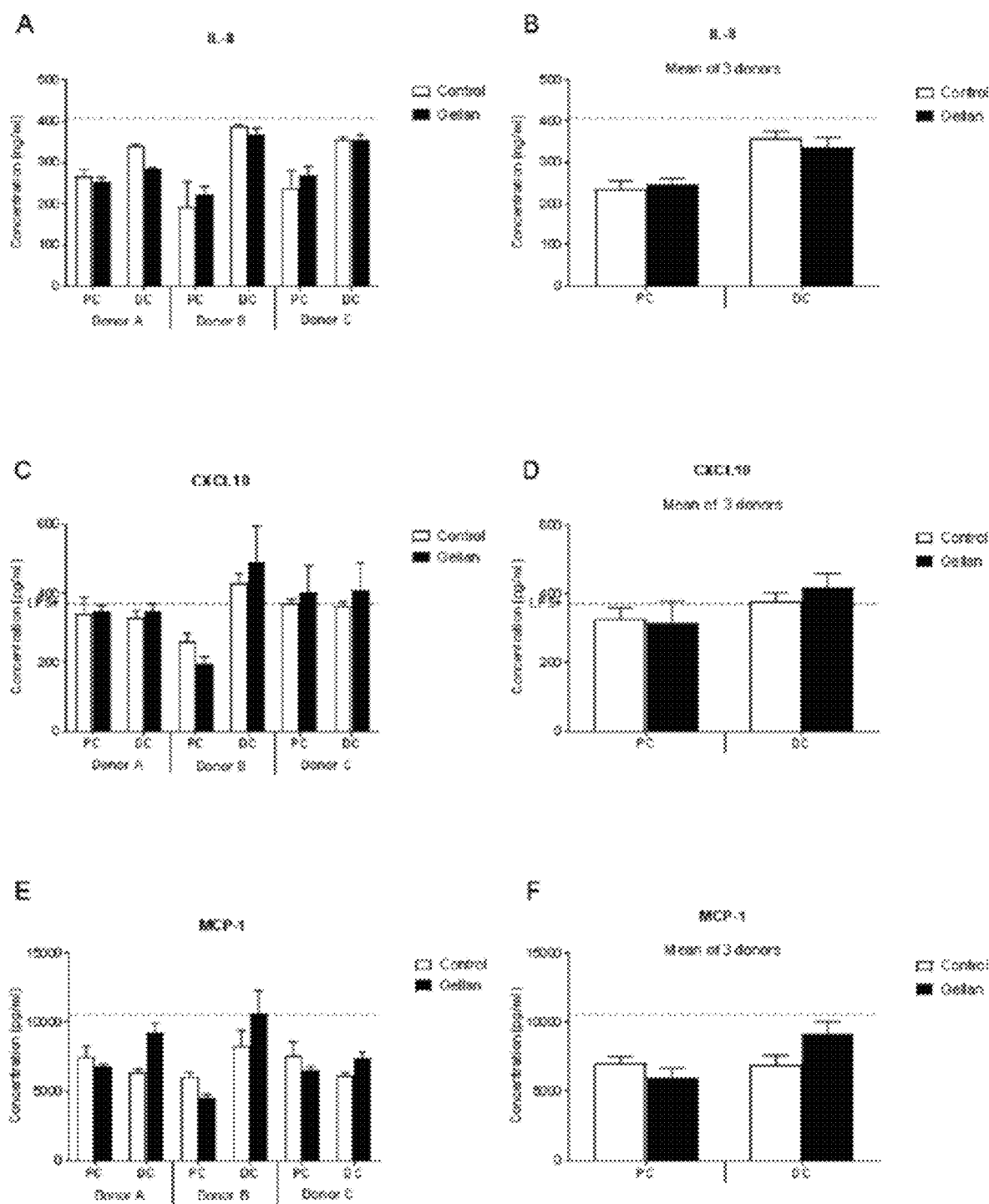
FIG. 25. Effect of SHIME samples on secretion of IL-8 (A+B), CXCL10 (C+D) and MCP-1 (E+F). Results are shown for the three different donors separately (A-C-E) and as the mean of the three donors (B-D-F). Cytokine levels were measured 6 h after LPS treatment on the basolateral side of the Caco-2/THP-1-Blue™ co-cultures after pretreatment of the apical side for 24 h with SHIME samples. The dotted line corresponds to the experiment control LPS+. Data are plotted as mean±SEM. No significant differences were found between the control and treatment of the three different donors. PC: proximal colon samples; DC: distal colon samples.

As seen in FIG. 25, IL-8 secretion tended to decrease upon Gellan Gum addition, compared to the control, for the distal colon samples for two of the three donors. However, this difference was not significant.

LPS-induced CXCL10 levels tended to slightly increase for the distal colon samples for all donors after treatment with Gellan Gum. In the proximal colon samples, only one donor showed a minor decrease in CXCL10 expression upon treatment. MCP-1 levels tended to slightly decrease after treatment for the proximal colon. In contrast, a clear increase was observed for the distal colon reactors of all donors. However, no significance was obtained.

To conclude, while Gellan Gum had a minor effect on the intestinal epithelial barrier function, it tended to increase the expression of the anti-inflammatory cytokines IL-6 and IL-10. Some conditions tended to decrease pro-inflammatory cytokine and chemokine production. However, only some statistically significant differences could be seen between the treatment and the control.

In order to have an overview of the changes induced by the treatment samples compared to the controls, the mean of the SHIME treatment samples of the three donors were normalized for the proximal and distal colon reactors to the mean of the SHIME control samples and plotted in Table 16.

TABLE 16

Cell experiment results from the mean of the SHIME treatment samples of the three donors normalized to the mean of the SHIME control samples.

| Colon | TEER | NF-κB | IL-6 | IL-10 | IL-1β | TNF-α | IL-8 | CXCL10 | MCP-1 |
|---|---|---|---|---|---|---|---|---|---|
| Proximal | 1.00 | 1.01 | 0.90 | 1.06 | 1.28 | 0.88 | 1.06 | 0.97 | 0.85 |
| Distal | 1.04 | 0.99 | 1.16 | 1.09 | 0.93 | 0.98 | 0.93 | 1.12 | 1.31 |

In general, it is reasonable to say that changes in immune markers in the treatment samples compared to the controls are rather mild. As seen in Table 16, Gellan Gum seems to enhance IL-10 secretion and to reduce TNF-α secretion in both colon reactors. IL-8 secretion is slightly reduced, while IL-6 is increased only for the distal colon samples. IL-1β secretion seems to be increased for the proximal colon samples, but these results are influenced by a significant increase of IL-1β in only one donor. MCP-1 secretion is decreased by Gellan Gum treatment for the proximal colon samples but is increased for the distal colon samples.

K. Summary of Example IV Results

The aim of this part of the study was to investigate the potential positive effects of Gellan Gum and its metabolites, on gut wall functions in terms of modulation of a leaky gut condition. This was done by evaluating intestinal epithelial permeability and specific immune markers in vitro.

Upon fermentation in the colon, Gellan Gum tended to improve the gut barrier integrity in terms of TEER. Although the increases were not significant, consistent increases were observed for all three donors when exposing distal colon samples to the in vitro model. Further, the product tended to have immunosuppressing properties, resulting in a tendency to lower levels of several immune mediators, including the pro-inflammatory cytokine TNF-α and chemoattractant protein IL-8, known to play a role in neutrophil recruitment. MCP-1, which promotes the clearance of neutrophils, tended to increase for the distal colon reactors after Gellan Gum treatment. On the other hand, IL-10, a bona fide anti-inflammatory cytokine, tended to increase, as well as IL-6, a cytokine involved in wound repair. All these reported changes were mostly observed in the distal colon reactors, thus suggesting a more pronounced effect of the fermentation products of Gellan Gum on the host immune cells in the distal regions of the colon.

CITATION LISTING OF NON-PATENT PUBLICATIONS

Anderson et al., Food Addit. Contam. (1990) 7(5): 583-590 ("Anderson (1990)").
Anderson et al., The dietary effects of gellan gum in humans, Food Addit. Contam. (1988) 5(3): 237-249 ("Anderson (1988)").
Bielecka et al., Food Research International (2002) 35: 125-131 ("Bielecka (2002)").
Cummings et al., Amer. J. Clin. Nutrit. (1987) 45: 1243-1255 ("Cummings (1987)").
Daguet et al., J. Funct. Foods (2016) 20: 369-379 ("Daguet (2016)").
Dann et al., J. Immunol. (2008) 180(10): 6816-6826 ("Dann (2008)").
Demigne et al., Brit. J. Nutrit. (1995) 74: 209-219 ("Demigne (1995)").
Diltz et al., Location of O-acetyl groups in S-657 using the reductive cleavage method, Carbohydr. Res. (2001) 331 (3): 265-270 ("Diltz (2001)").
Dumrese et al., FEBS Letters (2009) 583: 1637-1643 ("Dumrese (2009)").
Edwards et al., Caecal and faecal shortchain fatty acids and stool output in rats fed on diets containing nonstarch polysaccharides, Brit. J. Nutr. (1995) 73: 773-781 ("Edwards (1995)").
Esquivel-Elizondo et al., mSystems. (2017) 2(4): e00051-17 ("Esquivel-Elizondo (2017)").
Fallourd et al., Ingredient Selection for Stabilisation and Texture Optimisation of Functional Beverages and the Inclusion of Dietary Fibre, Functional and Specialty Beverage Technology (2009) Pt. 1, Sect. 1, 3-38, at 20 ("Fallourd (2009)").
Fasano, A., Physiol. Rev. (2011) 91: 151-175 ("Fasano (2011)").
FDA Guidance for Industry: Estimating the Maximum Safe Starting Dose in Initial Clinical Trials for Therapeutics in Adult Healthy Volunteers, July 2005 ("FDA Guidance (2005)").
Fehlbaum et al., In Vitro Fermentation of Selected Prebiotics and Their Effects on the Composition and Activity of the Adult Gut Microbiota, Int. J. Mol. Sci. (2018) 19: 3097 ("Fehlbaum (2018)").
Gibson et al., Nature Revs. Gastro. Hepatol. (2017) 14: 491-502 ("Gibson (2017)")
Glozak et al., Gene (2005) 363: 15-23 ("Glozak (2005)").
Groschwitz et al., J. Allergy Clin. Immunol. (2009) 124(1): 3-20 ("Groschwitz (2009)").
Guimaraes et al., Food Hydrocolloids (2018) 77: 787-795 ("Guimaraes (2018)").
Ha et al., W.J. Gastroenterol. (2014) 20(44):16498-16517 ("Ha (2014)").
Hashimoto et al., Arch. Biochem. Biophys. (1998) 354(1): 31-39 ("Hashimoto").
Jansson, et al., Structural Studies of a Polysaccharide (S-194) Elaborated by Alcaligenes ATCC 31961, Carbohydr. Res. (1986) 156: 157-163 ("Jansson (1986)").
Karlton-Senaye et al., Agro Food Ind. Hi Tech. (2013) 24(4): 10-14 ("Karlton-Senaye (2013)").
Kennedy et al. Microbiology (1994) 140: 3007-3013 ("Kennedy (1994)").
Kuo et al., Identification and Location of L-Glycerate, an Unusual Acyl Substituent in Gellan Gum, Carbohydr. Res. (1986) 156: 173-187 ("Kuo (1986)").
Li et al, Bioengineered (2019) 10(1): 240-249 ("Li (2019)").
Lyer et al., Crit. Rev. Immunol. (2012) 32(1): 23-63 ("Lyer (2012)").
Martinez et al., PLOS One (2010) 5(11): e15-46, ("Martinez (2010)").
Molly et al., Appl. Microbiol. Biotech. (1993) 39(2): 254-258 ("Molly (1993)").
Narushima et al., Gut Microbes (2014) 5(3): 333-339 ("Narushima (2014)").
Noor et al., BMC Gastroenterol. (2010) 10: 134 ("Noor (2010)").
Patel et al., Adv. Dairy Res. (2013) 1(2): 1-7 ("Patel (2013)").

Peng et al., Pediatric Res. (2007) 61: 37-41 ("Peng (2007)").
Possemiers et al., J. Agric. Food Chem. (2013) 61: 9380-9939 ("Possemiers (2013)").
Possemiers et al., FEMS Microbiol Ecol. (2004) 49(3): 495-507 ("Possemiers (2004)").
Saavedra et al., Brit. J. Nutrit. (2002) 87: s241-s246 ("Saavedra (2002)").
Sambuy et al., Cell Biology and Toxicology (2005) 21: 1-26 ("Sambuy (2005)").
Satsu et al., Exp. Cell Res. (2006) 312: 3909-3939 ("Satsu (2006)").
Scheller et al., Biochimica et Biophysica Acta (2011) 1813: 878-888 ("Scheller (2011)").
Stankowski et al., Location of the O-Acetyl Group in Welan by the Reductive-Cleavage Method, Carbohydr. Res. (1992) 224: 337-341 ("Stankowski (1992)").
Segata et al., Genome Biol. (2012) 13(6): R42, ("Segata (2012)").
Steer et al., Nutrit. Res. Revs. (2000) 13: 229-254 ("Steer (2000)").
Sworn G., Gellan Gum, Chapter 9 (pp. 204-227) in Handbook of Hydrocolloids (2nd. Ed.), (2009) Woodhead Publishing Series in Food Science, Technology and Nutrition ("Sworn (2009)").
Tetsuguchi et al, J. Nutr. Sci. Vitaminol. (1997) 43(5): 515-527 ("Tetsuguchi (1997").
Tuohy et al., Brit. J. Nutrit., (2001) 86: 341-348 ("Tuohy (2001)").
Tuohy et al., Microb. Ecol. Health Dis. (2002) 14: 165-173 ("Tuohy (2002)").
Van de Wiele et al., The Simulator of the Human Intestinal Microbial Ecosystem (SHIME®), Chapt. 27 (pp. 305-318) in The Impact of Food Bioactives on Health (Verhoeckx et al. Eds.) 2013: Springer, New York ("Van de Wiele (2013)").
Van den Abbeele et al., ISME J. (2013) 6(4):335-340 ("Van den Abbeele (2013)").
Van den Abbeele et al. Environ. Microbiol. (2011) 13(10): 2667-2680 ("Van den Abbeele (2011)").
Van den Abbeele et al., Microb Biotechnol. (2012) 5(1):106-115 ("Van den Abbeele (2012)").
Vinolo et al., Nutrients (2011) 3: 858-876 ("Vinolo (2011)").
Wong et al., J. Clin. Gastro. (2006) 40: 235-243 ("Wong (2006)").
Wright et al., Exp. Biol. Med. (1990) 195: 26-29 ("Wright (1990)").
Zeuner et al. Enzyme Microb. Technol. (January 2016) 82: 42-50 ("Zeuner (2016)").
Zitomersky et al., PLoS One (2013) 8(6): e63686, ("Zitomersky (2013)").
Zoetendal et al. App. Environ. Microbiol. (1998) 64: 3854-3859 ("Zoentendal (1998)").

Alternative embodiments, examples, and modifications which would still be encompassed by the disclosure may be made by those skilled in the art, particularly in light of the foregoing teachings. Further, it should be understood that the terminology used to describe the disclosure is intended to be in the nature of words of description rather than of limitation.

The subject matter of U.S. Provisional Application Nos. 62/794,452 and 62/869,248 is hereby incorporated by reference in its entirety. Additionally, the references described herein are incorporated by reference in their entirety to the extent necessary. In the event that there is a difference in meaning between the incorporated terms and the terms disclosed herein, the meaning of the terms disclosed herein will control.

Those skilled in the art will also appreciate that various adaptations and modifications of the preferred and alternative embodiments described above can be configured without departing from the scope and spirit of the disclosure. Therefore, it is to be understood that, within the scope of the appended claims, the disclosure may be practiced other than as specifically described herein.

The invention claimed is:

1. A method for promoting beneficial bacterial growth in the colon of a human, comprising
ingesting on an effective schedule a composition comprising a beneficial bacterial growth effective amount of a gellan oligosaccharide and an ingestible medium, wherein said ingesting increases a colonic *Faecalibacterium* level from about 10-fold to about 190-fold during treatment compared to an untreated control,
wherein the effective schedule comprises ingesting the composition daily, weekly, or monthly, and
wherein the amount of the gellan oligosaccharide ranges from about 10 mg/kg to about 150 mg/kg of the human ingesting the composition.

2. The method of claim 1, wherein the amount of the gellan oligosaccharide ranges from about 10 mg/kg to about 80 mg/kg of the human ingesting the composition.

3. The method of claim 1, wherein the gellan oligosaccharide comprises a high acyl gellan oligosaccharide, an intermediate acyl gellan oligosaccharide, a low acyl gellan oligosaccharide, or a combination thereof.

4. The method of claim 1, wherein the gellan oligosaccharide is obtained from a high acyl gellan polysaccharide, a low acyl gellan polysaccharide, or a combination thereof.

5. The method of claim 1, wherein the gellan oligosaccharide comprises a high acyl gellan oligosaccharide, an intermediate acyl gellan oligosaccharide, a low acyl gellan oligosaccharide, or a combination thereof.

6. The method of claim 1, wherein the gellan oligosaccharide comprises a high, intermediate, or low acyl gellan oligosaccharide, or a combination thereof obtained by a process, which comprises:
preparing a first composition comprising a high/intermediate/low acyl gellan or a high/intermediate/low acyl gellan polysaccharide and a liquid medium;
hydrolyzing a glycosidic bond of the high/intermediate/low acyl gellan or the high/intermediate/low acyl gellan polysaccharide to obtain a second composition;
subjecting the second composition to ultrafiltration, size-exclusion chromatography, precipitation, centrifugation, or a combination thereof to obtain a third composition comprising the gellan oligosaccharide; and
optionally, isolating or recovering the third composition.

7. The method of claim 1, wherein the gellan oligosaccharide comprises a high/intermediate/low acyl gellan oligosaccharide selected from
(i) a composition comprising Glc,GlcA, Glc,GlcA,Glyc, Glc,GlcA,Rha, Glc,GlcA,Rha,Glyc, Glc,GlcA,Rha,–H2O, Glc,Rha, Glc,Rha+28, Glc2,GlcA, Glc2,GlcA, Rha, Glc2,GlcA,Rha,+28, Glc2,GlcA,Rha,Ac, Glc2, GlcA,Rha,Glyc, Glc2,GlcA,Rha,Glyc,+28, Glc2,GlcA, Rha,Glyc.–H2O, Glc2,GlcA,Rha,–H2O, Glc2,GlcA, Rha2,Glyc, Glc2,GlcA2,Rha, Glc2,GlcA2,Rha2,Ac2, Glyc2,–H2O, Glc2,Rha, Glc3,GlcA,Rha, Glc3,GlcA, Rha2, Glc3,GlcA,Rha2, Glc3,GlcA,Rha2, Glc3,GlcA, Rha2,Glyc, Glc3,GlcA2,Rha, Glc3,GlcA2,Rha,Glyc, Glc3,GlcA2,Rha2,Glyc, Glc3,GlcA3,Rha2, Glc3, GlcA3,Rha2, Glc4,GlcA,Rha2,+43, Glc4,GlcA,Rha2, Ac, Glyc, Glc4,GlcA2,Rha, Glc4,GlcA2,Rha,Ac, Glyc,–H2O, Glc4,GlcA2,Rha,Ac,Glyc2, Glc4,GlcA2, Rha2,Ac,Glyc, Glc4,GlcA2,Rha2,Glyc, Glc4,GlcA3, Rha2, Glc4,GlcA2,Rha3,Ac, Glc4,GlcA3,Rha2/Glc4, GlcA2,Rha2,Glyc2, Glc5,GlcA2,Rha2, Glc5,GlcA2, Rha2, Glc5,GlcA2,Rha2,Ac, Glc5,GlcA4,Rha2, Glc6, GlcA3,Rha3, Glc(Ac/Glyc)x,GlcAx,Glcx,Rhax (where x is 4 to about 25), Glcx,GlcAx,Glcx,Rhax (where x is 4 to about 25), or a combination thereof;

(ii) a composition comprising a tetramer (Glc,GlcA,Glc, Rha), a tetramer (Glc,GlcA,Glc,Rha) with acetate and/ or glycerate, an octamer (Glc,GlcA,Glc,Rha,Glc,GlcA, Glc,Rha), an octamer (Glc,GlcA,Glc,Rha,Glc,GlcA, Glc,Rha) with acetate and/or glycerate, Glc,GlcA,Glc, Rha,Glc,GlcA, Glc,Rha;

(iii) a composition comprising a tetramer (Glc,GlcA,Glc, Rha), an octamer (Glc,GlcA,Glc,Rha,Glc,GlcA,Glc, Rha), a pentamer (Glc,GlcA,Glc,Rha,Glc), GlcA,Glc, Rha, Glc,GlcA,Glc, Glc,GlcA;

(iv) a composition comprising Glc(Glc-Glc),GlcA, Glc (Glc-Glc), GlcA,Glc, Glc,Glc;

(v) a composition comprising a tetramer (Glc,GlcA,Glc, Rha), GlcA,Glc,(Rha-Rha), Glc,(Rha-Rha),Rha, GlcA, Glc,Rha, Glc,GlcA,Glc, Rha,Glc, GlcA,Glc;

(vi) a composition comprising Glc,GlcA, Glc,GlcA,Glyc, Glc,GlcA,Rha, Glc,GlcA,Rha,Glyc, Glc,Rha, Glc, Rha+28, Glc2,GlcA, Glc2,GlcA,Rha, Glc2,GlcA, Rha,+28, Glc2,GlcA,Rha,Ac, Glc2,GlcA,Rha,Glyc, Glc2,GlcA,Rha,Glyc,+28, Glc3,GlcA,Rha, Glc3,GlcA, Rha2, Glc3,GlcA,Rha2, Glc3,GlcA,Rha2, Glc3,GlcA, Rha2,Glyc, Glc3,GlcA2,Rha,Glyc, Glc3,GlcA2,Rha2, Glyc, Glc3,GlcA3,Rha2, Glc4,GlcA,Rha2,Ac, Glyc, Glc4,GlcA2,Rha2,Ac,Glyc, Glc4,GlcA2,Rha2,Glyc, Glc4,GlcA2,Rha3,Ac, Glc4,GlcA3,Rha2/Glc4,GlcA2, Rha2,Glyc2, Glc5,GlcA2,Rha2, Glc5,GlcA2,Rha2,Ac, Glc(Ac/Glyc)x,GlcAx,Glcx,Rhax (where x is 4 to about 25), or a combination thereof;

(vii) a composition comprising Glc,GlcA, Glc,GlcA,Rha, Glc,Rha, Glc,Rha+28, Glc2,GlcA,Rha, Glc2,GlcA, Rha,+28, Glc2,GlcA2,Rha, Glc3,GlcA,Rha, Glc3, GlcA,Rha2, Glc3,GlcA2,Rha, Glc3,GlcA3,Rha2, Glc3,GlcA3,Rha2, Glc4,GlcA,Rha2,+43, Glc4,GlcA2, Rha, Glc4,GlcA3,Rha2, Glc5,GlcA2,Rha2, Glc5, GlcA2,Rha2, Glc5,GlcA4,Rha2, Glc6,GlcA3,Rha3, Glc(Ac/Glyc)x,GlcAx,Glcx,Rhax (where x is 4 to about 25), or a combination thereof;

(viii) a composition comprising Glc,GlcA,Rha,–H2O, Glc,Rha, Glc2,GlcA,Rha,–H2O, Glc2,Rha;

(ix) a composition comprising Glc,GlcA, Glc,GlcA,Glyc, Glc,GlcA,Rhaa, Glc,GlcA,Rha,Glyc, Glc,Rha, Glc, Rha+28, Glc2,GlcA, Glc2,GlcA,Rha, Glc2,GlcA, Rha,+28, Glc2,GlcA,Rha,Ac, Glc2,GlcA,Rha,Glyc, Glc2,GlcA,Rha,Glyc,+28, Glc2,GlcA,Rha,Glyc.– H2O, Glc2,GlcA,Rha2,Glyc, Glc2,GlcA2,Rha2,Ac2, Glyc2,–H2O, Glc3,GlcA,Rha, Glc3,GlcA,Rha2, Glc3, GlcA,Rha2,Glyc, Glc3,GlcA2,Rha,Glyc, Glc3,GlcA2, Rha2,Glyc, Glc3,GlcA3,Rha2, Glc4,GlcA,Rha2,+43, Glc4,GlcA,Rha2,Ac, Glyc, Glc4,GlcA2,Rha,Ac, Glyc,–H2O, Glc4,GlcA2,Rha,Ac,Glyc2, Glc4,GlcA2, Rha2,Ac,Glyc, Glc4,GlcA2,Rha2,Glyc, Glc4,GlcA3, Rha2, Glc4,GlcA2,Rha3,Ac, Glc4,GlcA3,Rha2/Glc4, GlcA2,Rha2,Glyc2, Glc5,GlcA2,Rha2, Glc5,GlcA2, Rha2,Ac, Glc(Ac/Glyc)x,GlcAx,Glcx,Rhax (where x is 4 to about 25), or a combination thereof;

or a combination of any one of (i) to (ix).

8. The method of claim 1, wherein the gellan oligosaccharide comprises a gellan oligosaccharide obtained from a gellan gum.

9. The method of claim 1, wherein the gellan oligosaccharide comprises a high/low acyl gellan oligosaccharide and wherein said ingesting increases colonic levels of *Blautia, Parabacteroides, Clostridium* XVIII, or a combination thereof.

10. The method of claim 9, wherein one or more of the following occurs:
    (a) the *Blautia* levels increase up to at least about 5-fold compared to untreated control,
    (b) the *Parabacteroides* levels increase from about 2-fold to about 40-fold compared to untreated control,
    (c) the *Faecalibacterium* levels increase from about 40-fold to about 190-fold during treatment compared to untreated control, and
    (d) the *Clostridium* XVIII levels increase from about 12-fold to about 60-fold compared to untreated control.

11. The method of claim 1, wherein the amount of gellan oligosaccharide is selected from about 1 g to about 10 g, about 1 g to about 9 g, about 1 g to about 8 g, about 1 g to about 7 g, about 1 g to about 6 g, about 1 g to about 5 g, about 1 g to about 4 g, about 1 g to about 3 g, or about 2 g.

12. The method of claim 1, wherein the amount of the gellan oligosaccharide is sufficient to achieve an effective gellan oligosaccharide concentration in the colon of the human, where said gellan oligosaccharide colon concentration ranges from about 1 mg/mL to about 10 mg/mL.

13. The method of claim 1, wherein the amount of the gellan oligosaccharide is sufficient to achieve an effective gellan oligosaccharide concentration in the colon of the human, where said gellan oligosaccharide colon concentration ranges from about 4 mg/mL to about 10 mg/mL.

14. The method of claim 1, wherein the amount of gellan oligosaccharide ranges from about 10 mg/kg to about 100 mg/kg of the human ingesting the composition.

15. The method of claim 1, wherein the gellan oligosaccharide has a molecular weight of from about 0.3 kDa to about 12 kDa.

16. The method of claim 1, wherein the composition further comprises a probiotic.

17. The method of claim 1, wherein the method further comprises ingesting a probiotic, an additional prebiotic, or a combination thereof.

18. The method of claim 1, wherein the composition is in an ingestible form selected from liquid, semi-solid, solid, cereal, snack bar, juice, smoothie, milk, ice cream, yoghurt, and beverage.

19. The method of claim 1, wherein the composition is in a powdered form in a sealed container or package.

20. The method of claim 1, wherein the composition is in a form of a tablet or a capsule.

* * * * *